(12) United States Patent
Yaosaka et al.

(10) Patent No.: US 9,751,821 B1
(45) Date of Patent: *Sep. 5, 2017

(54) METHOD FOR PRODUCTION OF 3-HYDROXYPROPAN-1-ONE COMPOUND, METHOD FOR PRODUCTION OF 2-PROPEN-1-ONE COMPOUND AND METHOD FOR PRODUCTION OF ISOXAZOLINE COMPOUND

(71) Applicant: NISSAN CHEMICAL INDUSTRIES, LTD., Tokyo (JP)

(72) Inventors: Manabu Yaosaka, Funabashi (JP); Tomohisa Utsunomiya, Funabashi (JP); Yuji Moriyama, Funabashi (JP); Tomohiro Matsumoto, Funabashi (JP); Kazutaka Matoba, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/586,913

(22) Filed: May 4, 2017

Related U.S. Application Data

(62) Division of application No. 14/584,642, filed on Dec. 29, 2014, now Pat. No. 9,676,692, which is a division of application No. 12/452,347, filed as application No. PCT/JP2008/061771 on Jun. 27, 2008, now Pat. No. 8,952,175.

(30) Foreign Application Priority Data

| Jun. 27, 2007 | (JP) | ................. | 2007-169151 |
| Aug. 31, 2007 | (JP) | ................. | 2007-225992 |
| Nov. 12, 2007 | (JP) | ................. | 2007-293175 |

(51) Int. Cl.

| C07C 45/72 | (2006.01) |
| C07D 413/14 | (2006.01) |
| C07C 51/367 | (2006.01) |
| C07C 231/12 | (2006.01) |
| C07D 213/04 | (2006.01) |
| C07C 67/343 | (2006.01) |
| C07D 249/08 | (2006.01) |
| C07D 233/60 | (2006.01) |
| C07D 401/04 | (2006.01) |
| C07D 413/12 | (2006.01) |

(52) U.S. Cl.
CPC ............ *C07C 45/72* (2013.01); *C07C 51/367* (2013.01); *C07C 67/343* (2013.01); *C07C 231/12* (2013.01); *C07D 213/04* (2013.01); *C07D 233/60* (2013.01); *C07D 249/08* (2013.01); *C07D 401/04* (2013.01); *C07D 413/12* (2013.01); *C07D 413/14* (2013.01)

(58) Field of Classification Search
CPC .................................................. C07C 45/72
See application file for complete search history.

(56) References Cited

U.S. PATENT DOCUMENTS

| 4,215,076 A | 7/1980 | Stueben et al. |
| 5,300,689 A | 4/1994 | Krbechek et al. |
| 5,939,360 A | 8/1999 | Adachi et al. |
| 6,541,642 B1 | 4/2003 | Yagihara et al. |
| 7,662,972 B2 | 2/2010 | Mita et al. |
| 2009/0023923 A1 | 1/2009 | Mizukoshi et al. |

FOREIGN PATENT DOCUMENTS

| JP | 2007/106756 A | 4/2007 |
| JP | 2008/260691 A | 10/2008 |
| WO | 2005/085216 A1 | 9/2005 |
| WO | 2007/070606 A2 | 6/2007 |
| WO | 2007/074789 A1 | 7/2007 |
| WO | 2009/025983 A2 | 2/2009 |
| WO | 2009/126668 A2 | 10/2009 |

OTHER PUBLICATIONS

Nevar et al., "One Step Preparation of 1,4-Diketones from Methyl Ketones and a-Bromomethyl Ketones in the Presence of ZnC12-t-BuOH-Et2NR as a Condensation Agent," Synthesis, 2000, vol. 9, pp. 1259-1262.
Tanabe et al., "Direct, practical, and powerful crossed aldol additions between ketones and ketones or aldehydes utilizing environmentally benign TiCl4-Bu3N reagent," Tetrahedron, vol. 58, 2002, pp. 8269-8280.
Chai, "Aldol-Type Self Condensation of a-Halo-a,a-difluoromethyl-ketones by Using the Bimetal Redox System [Cr(III)/Fe]," Bulletin Korean Chemistry Society, 1999, vol. 20, No. 1, pp. 101-102.
Li et al., "Zinc-Mediated C-C Bond Sigmatropic Rearrangement: A New and Efficient Methodology for the Synthesis of b-Diketones," J. Org. Chem., 2007, vol. 72, pp. 8131-8134.
Sosnovskikh et al., "Ketone-Ketone Condensation with the Participation of Polyhaloalkyl Phenyl Ketones," Zhurnal Organicheskoi Khimi, vol. 28, No. 3, pp. 518-526, Mar. 1992.
Desenko, S. et al., "Cyclocondensation of 6-Acetyl-4,7-dihydro-5-methyl-7-phenyl[1,2,4]triazolo[1,5-α]pyrimidine with Hydroxylamine and Hydrazine," Journal of Heterocyclic Chemistry, Jul.-Aug. 1998, pp. 989-990, vol. 35.
Kidwai, M. et al., "Ring Closure Reactions of Chalcones Using Microwave Technology," Synthetic Communications, 1999, pp. 3237-3250, vol. 29, No. 18, published by Marcel Dekker, Inc.

(Continued)

*Primary Examiner* — Robert Havlin
(74) *Attorney, Agent, or Firm* — Oliff PLC

(57) ABSTRACT

There is provided a novel intermediate for producing pesticides. A method for producing the compound of Formula (3) comprises reacting an aromatic ketone compound of Formula (4) and a substituted acetophenone compound of Formula (5) as starting raw materials in an organic solvent or water in the presence or absence of an additive in the presence of a base in a suspended state. A method may comprise dehydrating the compound of Formula (3). A method for producing compound (2) in one step comprises reacting compound (4) and compound (5) to obtain compound (3). Further, a method for producing an isoxazoline compound of Formula (1) comprises reacting compound (2) and a hydroxylamine in an aliphatic or an aromatic hydrocarbon solvent which is optionally substituted by a halogen atom by adding an additive selected from a phase-transfer catalyst, a $C_1$-$C_6$ alcohol and an aprotic polar solvent in the presence of a base and water.

11 Claims, No Drawings

(56) References Cited

OTHER PUBLICATIONS

Barten J. et al., "Simple access to novel β-hydroxy-β-trifluoromethyl imines," Journal of Fluorine Chemistry, 2002, pp. 105-109, vol. 113, published by Elsevier Science B.V.
Tokuda, O. et al.,"A Practical Synthese of (S)-2-Cyclohexyl-2-phenylglycolic Acid via Organocatalytic Asymmetric Construction of a Tetrasubstituted Carbon Center," Organic Letters, Sep. 2005, pp. 5103-5105, vol. 7, No. 22, published by American Chemical Society, USA.
Suri, J. et al., "Dihydroxyacetone Variants in the Organocatalytic Construction of Carbohydrates: Mimicking Tagatose and Fuculose Aldolases," Journal of Organic Chemistry, Apr. 2006, pp. 3822-3828, vol. 71, No. 10, published by American Chemical Society, USA.
Qiu, I. et al., "Proline Catalyzed Asymmetric Aldol Reaction between Methyl Ketones and 1-Aryl-2,2,2-trifluoroethanones," Chinese Journal of Chemistry, 2005, pp. 584-588, vol. 23.
Moiseev, A. et al., "Stereoselective Synthesis of 3,5-Diakyl-3,5-dihdro-3,5-diphenyl-4H-pyrazol-4-ones," Synthesis, Aug. 2005, pp. 2901-2905, No. 17, published by Georg Thieme Verlag Stuttgart, New York, USA.
Yoshida, Y. et al., "TiC14/Bu3N/(catalytic TMSOTf): Efficient Agent for Direct Aldol Addition and Claisen condensation," Tetrahedron Letters, 1997, pp. 8727-8730, vol. 38, No. 50, published by Elsevier Science Ltd.
Mori, Y. et al., "Use of boron enolates in water. The first boron enolate-mediated diastereoselective aldol reactions using catalytic boron sources," Tetrahedron, 2002, pp. 8263-8268, vol. 58, published by Elsevier Science Ltd.
Wang, G. et al., "Environmentally Friendly and Efficient Process for the Preparation of β-Hydroxyl Ketones," Organic Process Research and Development, Nov. 2003, pp. 18-21, vol. 8, No. 1, published by American Chemical Society, USA.
Concellon, J. et al., "Preparation of (Z)-α,β-unsaturated ketones with total or high diastereoselectivity," Tetrahedron, 2002, pp. 7775-7780, vol. 58, No. 39, published by Elsevier Science Ltd.
Roy, A. et al., "Enantiospecific synthesis of 5',5',5'-trifluoro-5'-deoxyneplanocin A," Tetrahedron Letters, 2005, pp. 3913-8515, vol. 46, published by Elsevier Ltd.
Konno, T. et al., "Palladium-Catalyzed Regio-and Stereoselective Formate Reduction of Fluorine-Containing Allylic Mesylates, A New Entry for the Construction of a Tertiary Carbon Attached with a Fluoroalkyl Group," Journal of Organic Chemistry, 2006, pp. 3545-3550, vol. 71, No. 9, published by American Chemical Society, USA.
Shen, Y. et al., "Stille cross-coupling reaction of polyfluorovinylstannanes Sterospecific synthesis of polyfluoroalkenes and -α,β-unsaturated ketones," Journal of Fluorine Chemistry, 2003, pp. 91-94, vol. 125, No. 1, published by Elsevier B.V.
Venkatesan, C. et al., "Condensation of acetophenone to α,β-unsaturated ketone (dypnome) over solid acid aatalysts," Journal of Molecular Catalysis A: Chemical, 2002, pp. 179-187, vol. 181, published by Elsevier Science B.V.
Venturella, P. et al., "Sintesi Di Indolilcalconi E Indolilcromonoli," II Farmaco-Edizione Scientifica, 1971, pp. 591-596, vol. 26, No. 7.
Zoorob, H. et al., "Study of the Reactivity of 2-Cinnamoylbenzimidazole towards Thiourea, Urea, Hydrazines and Hydroxylamine Hydrochloride," Zeitschrift Für Naturforschung, Teil b: Anorganische Chemie, Organische Chemie, 1977; pp. 443-446.

Sinisterra, J.V. et al., "Ba(OH)2 as the Catalyst in Organic Reactions-Part X-Reaction of Chalcone with Hydroxylamine," Bulletin des Societes Chimiques Beiges, 1987, pp. 293-302, vol. 96, No. 4.
Eissa, A. et al., "Synthesis and Antimicrobial Activity of Novel Tetrahydrobenzothienopyrimidines," Archives of Pharmacal Reasearch, 2004, pp. 885-892, vol. 27, No. 9.
Moskalev, N. et al., "Synthesis of Functionally Substituted Alcohols Containing a CF3 Group by the Condensation of Aryl and Heteroaryl Trifluoromethyl Ketones With CH Acids," pp. 1902-1904, translated from: Zhumal Organicheskoi Khimii, 1990, pp. 2205-2208, vol. 26, No. 10.
Agrawal, N. et al., "Synthesis of Pyrazolinie and Isoxazoline in Triethanolamine Medium," Indian Journal of Chemistry, Dec. 2004, pp. 2700-2701, vol. 43B, No. 12, published by the National Institute of Science Communication and Information Resources, New Delhi, India.
Chen, Y. et al, "Solid-Phase Synthesis of Pyrazolines and Isoxazolines with Sodium Benzenesulfinate as a Traceless Linker," Organic Letters, 2003, pp. 1067-1069, vol. 5, No. 7, published by the American Chemical Society, USA.
Song, J. et al., "N-Heterocyclic Carbene-Catalyzed Mukaiyama Aldol Reactions," Organic Letters, 2007, pp. 1013-1016, vol. 9, No. 6, published by the American Chemical Society, USA.
Kel'in, A. et al., "A New Simple Synthesis of Aryl-Substituted 1,4-Diketones," Synthesis, 1996, pp. 330-332.
Ishihara, T. et al., "Regiospecific α-Hexafluoroisopropylidenation of Ketones Using Hexafluoroacetone," Journal of Fluorine Chemistry, 1983, pp. 1-19, vol. 22, No. 1.
Newbound, T. et al., "'Half-Open Cobaltocene' Chemistry:Diene Replacement vs. Hydride Abstraction by the Triphenylmethyl Cation," Journal of Organomettalic Chemistry, 1986, pp. 213-220, vol. 316, Nos. 1-2.
Tordeux, M. et al., "Preparation of the 4-Carboethoxy-3-Trifluoromethylcyclohex-2-Enone," Synthetic Communication, 1991, pp. 1242-1245, vol. 21, Nos. 10-11.
Noguchi, T. et al., "Indoline Derivatives I: Synthesis and Factor Xa (FXa) Inhibitory Activities," Chemical and Pharmacetical Bulletin, Feb. 2006, pp. 163-174, vol. 54, No. 2, Published by the Pharmaceutical Society of Japan, Japan.
Gillmore, A. et al., "A Route to the Structure Proposed for Puetuberosanol and Approaches to the Natural Products Marshrin and Phebalosin," Tetrahedron, 2003, pp. 4363-4375, vol. 59, No. 24, published by Elsevier Science Ltd.
Eistert, B. et al., "Reaktionen von monosubstituierten Benzaldehyden mit Diazomethan," Chemische Berichte, 1976, pp. 640-649, vol. 109, No. 2.
International Search Report issued in International Application No. PCT/JP2008/061771 dated Sep. 2, 2008.
Yu et al.; "Asymmetric zinc-Reformatsky reaction of Evans chiral imide with acetophenones and its application to the stereoselective synthesis of triazole antifungal agents," Tetrahedron: Asymmetry, 2007; pp. 942-962, vol. 18, No. 8.
Kohler et al.; "The Reaction between Organic Magnesium Compounds and Alpha Bromo Ketones II;" Journal of American Chemical Society; Jan. 1935; pp. 217-224; vol. 57.
Extended European Search Report dated Nov. 16, 2010 for European Patent Application No. 08777683.7.
Powers et al., (Tetrahedron, 54 (1998), p. 4085-96).
Grunanger et al., (Chapter 2—Isoxazolines in "Chemistry of Heterocyclic Compounds: Isoxazoles, Part 1, vol. 49," (1991), pp. 417-485 provided).
March's Advanced Organic Chemistry, 5th Ed., (2001), Ch. 16 provided.

METHOD FOR PRODUCTION OF 3-HYDROXYPROPAN-1-ONE COMPOUND, METHOD FOR PRODUCTION OF 2-PROPEN-1-ONE COMPOUND AND METHOD FOR PRODUCTION OF ISOXAZOLINE COMPOUND

This is a Division of application Ser. No. 14/584,642 filed on Dec. 29, 2014, which in turn is a Division of application Ser. No. 12/452,347 filed Dec. 28, 2009, which in turn is a National Phase application of PCT/JP2008/061771 filed on Jun. 27, 2008. The disclosures of the prior applications are hereby incorporated by reference herein in their entirety.

TECHNICAL FIELD

The present invention relates to a method for producing a 3-hydroxypropan-1-one compound, a 2-propen-1-one compound and an isoxazoline compound which are useful for functional materials such as medical drugs, agricultural chemicals or electronic materials or production intermediates thereof.

BACKGROUND ART

Methods for producing an isoxazoline compound from a 1,3-bis(substituted phenyl)-3-substituted-2-propen-1-one compound and hydroxylamine as raw materials have been known in, for example, Non-patent Documents 1 to 6.

Several methods for producing a 1,3-bis(substituted phenyl)-3-substituted-3-hydroxypropan-1-one compound from an aromatic ketone compound and a substituted acetophenone compound as starting raw materials have been known (for example, Patent Document 1 and Non-patent Documents 7 to 15).

Moreover, methods for producing a 1,3-bis(substituted phenyl)-3-substituted-2-propen-1-one compound from a 1,3-bis(substituted phenyl)-3-substituted-3-hydroxypropan-1-one compound as a raw material have been known in, for example, Non-patent Documents 10 and 11.

Furthermore, methods for producing a 1,3-bis(substituted phenyl)-3-substituted-2-propen-1-one compound from an aromatic ketone compound and a substituted acetophenone compound as starting raw materials in one step have been known in, for example, Non-patent Documents 18 to 20.
[Patent Document 1]
WO 2007/074789 pamphlet
[Non-patent Document 1]
Farmaco, Edizione Scientifica (1971), 591-596
[Non-patent Document 2]
Zeitschrift fuer Naturforschung, Teil B: Anorganische Chemie, Organische Chemie (1977), 443-446
[Non-patent Document 3]
Bulletin des Societes Chimiques Beiges (1987), 293-302
[Non-patent Document 4]
Journal of Heterocyclic Chemistry (1998), 989-990
[Non-patent Document 5]
Synthetic Communication (1999), 3237-3250
[Non-patent Document 6]
Archives of Pharmacal Research (2004), 885-892
[Non-patent Document 7]
Zhurnal Organicheskoi Khimii, vol. 26, No. 10, 2205-2208 (1990)
[Non-patent Document 8]
Journal of Fluorine Chemistry, vol. 113, 105-109 (2002)
[Non-patent Document 9]
Organic Letters vol. 7, No. 22, 5103-5105 (2005)
[Non-patent Document 10]
Journal of Organic Chemistry, vol. 71, 3822-3828 (2006)
[Non-patent Document 11]
Chinese Journal of Chemistry, vol. 23, 584-588 (2005)
[Non-patent Document 12]
Synthesis, No. 17, 2901-2905 (2005)
[Non-patent Document 13]
Tetrahedron Letters, vol. 38, 8727-8730 (1997)
[Non-patent Document 14]
Tetrahedron, vol. 58, 8263-8268 (2002)
[Non-patent Document 15]
Organic Process Research and Development, vol. 8, 18-21 (2004)
[Non-patent Document 16]
Tetrahedron, Vol. 58, No. 39, 7775-7780 (2002)
[Non-patent Document 17]
Tetrahedron Letters, vol. 46, 8913-8915 (2005)
[Non-patent Document 18]
Journal of Organic Chemistry, Vol. 71, No. 9, 3545-3555 (2006)
[Non-patent Document 19]
Journal of Fluorine Chemistry, Vol. 125 No. 1, 91-94 (2004)
[Non-patent Document 20]
Journal of Molecular Catalysis A: Chemical, Vol. 181, 179-187 (2002)

DISCLOSURE OF THE INVENTION

Problems to be Solved by the Invention

The reaction conditions described in Non-patent Documents 1 to 4 and 6 are the reactions in which alcoholic solvents such as ethanol are used to react basic compounds such as sodium hydroxide, potassium hydroxide, barium hydroxide and pyridine. In recent synthetic examples, methods of reacting the basic compound in an alcoholic solvent are common methods used for producing an isoxazoline compound from a 1,3-bis(substituted phenyl)-3-substituted-2-propen-1-one compound and hydroxylamine as raw materials, as far as the present inventors have known. However, yields are moderate in many cases of these reaction examples. In addition, although these methods require a liquid separation operation in order to remove overused hydroxylamine, these methods do not provide industrial satisfaction due to the difficulty in recovery, the increase in environmental load and the increase in cost when alcoholic solvents are used. Non-patent Document 5 describes the method of using pyridine as a solvent and a base. However, this method provides low yield of around 50%, and pyridine also has difficulty in recovery similar to alcohol. Moreover, Non-patent Document 5 describes the reaction example in which methylene chloride is used as a solvent. However, this reaction example has limitation of equipment and the like in industrial production, because microwave irradiation is required.

As described above, in related art methods, there is no method of producing an isoxazoline compound in low-polarity solvents as represented by toluene which are recovered easily from a 1,3-bis(substituted phenyl)-3-substituted-2-propen-1-one compound and hydroxylamine as raw materials, so that there is room for improvement.

In the reaction condition described in Non-patent Document 7, since n-butyl lithium which is expensive and requires careful handling is used as a base, this reaction is not satisfactory in industrial processes. In the reaction condition described in Non-patent Document 8, an aromatic ketone compound is required to be converted into imine once and then is made to react. After the reaction, the imine part is required to be reconverted. Therefore, this reaction leads to an increase in production cost and waste materials, and is not satisfactory as an industrial production method. In the reaction conditions described in Non-patent Documents 9 to 11, proline is used as a catalyst. The yields in these descriptions are comparatively high. However, since solvents which have difficulty in recovery or halogen-based solvents are required, the reaction is not satisfactory in an industrial production method. In the reaction conditions described in Non-patent Documents 12 and 13, the reaction leads to an increase in production cost and waste materials because titanium tetrachloride is used stoichiometrically, and has a problem of equipment and the like in industrial production because the reaction requires ultra cold temperature of −78° C. In the reaction conditions described in Non-patent Document 14, the reaction is conducted in water by adding a surfactant. This reaction is required to be effected after an aromatic ketone compound is converted into a silyl ether. This leads to an increase in production cost and waste materials, and the reaction is not satisfactory as an industrial production method. In the reaction conditions described in Non-patent Document 15, the reaction is also conducted in water. However, the amount of water to be used is very large, and this reaction is not satisfactory for industrial production in volume efficiency.

In the reaction conditions described in Non-patent Document 16, a dehydration agent and a base are used in a solvent amount. In the reaction conditions described in Non-patent Document 17, solvents are used in some cases, but the solvents used are halogen-based organic solvents. These reactions are not satisfactory in industry, because the reactions described in both documents have large environmental loads and increased costs.

In the reaction conditions described in Non-patent Document 18, one of the starting raw materials is converted into a phosphorus ylide, and this ylide is reacted with another starting raw material. Therefore, this reaction is not satisfactory in production cost. In the reaction conditions described in Non-patent Document 19, raw materials are reacted with each other using a transition metal catalyst. However, this reaction is difficult to use in industry, because a tin compound which has anxiety of toxicity is required to be used. In the reaction conditions described in Non-patent Document 20, a solid catalyst which can be recovered and reused is used. However, the reaction is not satisfactory in industry, because the conversion ratio is low.

As described above, in related art methods, there is no method for producing a 1,3-bis(substituted phenyl)-3-substituted-3-hydroxypropan-1-one compound from an aromatic ketone compound and a substituted acetophenone compound as raw materials with water which is harmless for the environment and creatures as a solvent without using expensive reagents and with good volume efficiency. In addition, a method for production characterized in that a reaction is conducted in the presence of a base in a low-polarity solvent as represented by toluene which is recovered easily and the equilibrium reaction is distributed to the target product side by generating slurry has not been known, so that there is room for improvement.

In addition, there is no method for producing a 1,3-bis (substituted phenyl)-3-substituted-2-propen-1-one compound from a 1,3-bis(substituted phenyl)-3-substituted-3-hydroxypropan-1-one compound as a raw material in a low-polarity solvent as represented by toluene which is recovered easily by using a dehydration agent and a base, and a method for producing a 1,3-bis(substituted phenyl)-3-substituted-2-propen-1-one compound from an aromatic ketone compound and a substituted acetophenone compound as starting raw materials in one step has also not been known, so that there is room for improvement.

Means for Solving the Problems

As a result of an intensive investigation for achieving the above-described objects, the present inventors have discovered a method for producing a 1,3-bis(substituted phenyl)-3-substituted-3-hydroxypropan-1-one compound from an aromatic ketone compound and a substituted acetophenone compound as raw materials by conducting the reaction in the presence of a base in water which is harmless or in a low-polarity solvent as represented by toluene which is recovered easily and distributing the equilibrium reaction to the target product side by generating slurry, and have accomplished the present invention.

In addition, the present inventors also have discovered a method for producing a 1,3-bis(substituted phenyl)-3-substituted-2-propen-1-one compound from a 1,3-bis(substituted phenyl)-3-substituted-3-hydroxypropan-1-one compound as a raw material in a low-polarity solvent as represented by toluene which is recovered easily by using a dehydration agent and a base, and moreover a method for producing a 1,3-bis(substituted phenyl)-3-substituted-2-propen-1-one compound from an aromatic ketone compound and a substituted acetophenone compound as starting raw materials in one step, and have accomplished the present invention.

Furthermore, the present inventors also have discovered a method for producing an isoxazoline compound from 1,3-bis(substituted phenyl)-3-substituted-2-propen-1-one compound and hydroxylamine as raw materials in low-polarity solvents as represented by toluene which are recovered easily, and have accomplished the present invention.

Namely, the present invention is:
[1] a method for producing an isoxazoline compound represented by Formula (1):

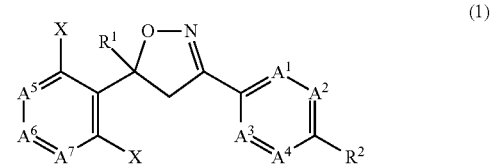

(where $R^1$, $R^2$, X, $A^1$, $A^2$, $A^3$, $A^4$, $A^5$, $A^6$ and $A^7$ represent the same meaning as described below), includes reacting a 1,3-bis(substituted phenyl)-3-substituted-2-propen-1-one compound represented by Formula (2):

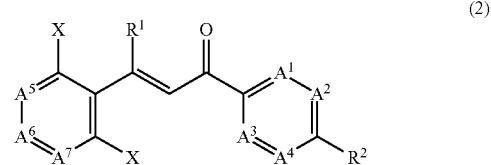

(where $R^1$ represents a $C_1$-$C_6$ haloalkyl or $C_3$-$C_8$ halocycloalkyl;
each of $A^1$, $A^2$, $A^3$ and $A^4$ independently represents N or C—Y;

each of $A^5$, $A^6$ and $A^7$ independently represents N or C—X;

X represents a hydrogen atom, a halogen atom, cyano, nitro, —$SF_5$, $C_1$-$C_6$ alkyl, $C_1$-$C_6$ haloalkyl, hydroxy ($C_1$-$C_6$) haloalkyl, $C_1$-$C_6$ alkoxy ($C_1$-$C_6$) haloalkyl, $C_1$-$C_6$ haloalkoxy ($C_1$-$C_6$) haloalkyl, $C_3$-$C_8$ halocycloalkyl, —$OR^3$, —$OSO_2R^3$ or —$S(O)_rR^3$; and each X may be the same as or different from each other;

$R^3$ represents a $C_1$-$C_6$ alkyl, $C_1$-$C_4$ alkoxy ($C_1$-$C_4$) alkyl, $C_1$-$C_6$ haloalkyl or $C_1$-$C_3$ haloalkoxy ($C_1$-$C_3$) haloalkyl;

$R^2$ represents a $C_1$-$C_6$ alkyl, a halogen atom, cyano, nitro, —$NH_2$, —$N(R^5)R^4$, —OH, —$OR^3$, benzyloxy, —$OSO_2R^3$, phenylsulfonyloxy, phenylsulfonyloxy substituted by $(Z)_{p1}$, —C(O)OH, —C(O)$OR^3$, —C(O)$NH_2$, —C(O)N($R^{1b}$)$R^{1a}$, —C(S)N($R^{1b}$)$R^{1a}$, -L-Q, -L-N($R^{1c}$)$R^{1d}$, —$S(O)_r$-$L^2$-$Q^2$ and a substituent selected from D-1 to D-50;

Y represents a hydrogen atom, a halogen atom, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_6$ alkylthio, $C_1$-$C_6$ haloalkylthio, $C_1$-$C_6$ alkylsulfonyl, $C_1$-$C_6$ haloalkylsulfonyl, —$NH_2$, or —$N(R^5)R^4$, and each Y may be the same as or different from each other;

two adjacent Ys may form $A^8$=$A^9$–$A^{10}$=$A^{11}$ together;

each of $A^8$, $A^9$, $A^{10}$ and $A^{11}$ independently represents N or C—$Y^1$;

$Y^1$ represents a hydrogen atom, a halogen atom, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_6$ alkylthio, $C_1$-$C_6$ haloalkylthio, $C_1$-$C_6$ alkylsulfonyl, $C_1$-$C_6$ haloalkylsulfonyl, —$NH_2$, or —$N(R^5)R^4$, and each $Y^1$ may be the same as or different from each other;

$R^4$ represents a $C_1$-$C_6$ alkyl, —CHO, $C_1$-$C_6$ alkylcarbonyl, $C_1$-$C_6$ haloalkylcarbonyl, $C_1$-$C_6$ alkoxycarbonyl, $C_1$-$C_6$ alkylthiocarbonyl, $C_1$-$C_6$ alkoxythiocarbonyl, $C_1$-$C_6$ alkyldithiocarbonyl, $C_1$-$C_6$ alkylsulfonyl or $C_1$-$C_6$ haloalkylsulfonyl;

$R^5$ represents a hydrogen atom or $C_1$-$C_6$ alkyl;

$R^{1a}$ represents a $C_1$-$C_6$ alkyl, $C_1$-$C_6$ alkyl optionally substituted by $R^8$, $C_3$-$C_6$ cycloalkyl which may be ring-condensed by benzene ring, $C_3$-$C_6$ alkenyl, $C_3$-$C_6$ haloalkenyl, $C_3$-$C_6$ alkynyl, —N($R^{11}$)$R^{10}$, —C(O)$OR^9$, —C(O)$NH_2$, —C(O)$NHR^9$, —C($R^7$)=$NOR^6$, phenyl, phenyl substituted by $(Z)_{p1}$, D-5, D-7, D-10, D-11, D-12, D-14, D-15, D-18, D-31, D-32, D-42, D-43, D-45, D-46, D-48, E-1, E-2, E-3, E-4 or E-7;

$R^{1b}$ represents a hydrogen atom, $C_1$-$C_6$ alkyl, $C_1$-$C_4$ alkoxy ($C_1$-$C_4$) alkyl, cyano ($C_1$-$C_6$) alkyl, $C_3$-$C_6$ alkynyl, —C(O)$R^9$ or —C(O)$OR^9$, or represents that $R^{1b}$ may form a 3-7 membered ring with a nitrogen atom to be bonded, by forming a $C_2$-$C_6$ alkylene chain together with $R^{1a}$, and this alkylene chain may contain one oxygen atom, sulfur atom or nitrogen atom in this case;

L represents —C($R^{2a}$)($R^{2b}$)—, —C($R^{2a}$)($R^{2b}$)$CH_2$—, —$CH_2$C($R^{2a}$)($R^{2b}$)— or —N($R^{2c}$)—;

Q represents a hydrogen atom, a halogen atom, cyano or nitro;

$R^{1c}$ represents a hydrogen atom, —C(O)$R^{3a}$, —C(O)$OR^{3a}$, —C(O)$SR^{3a}$, —C(O)N($R^{3b}$)$R^{3a}$, —C(S)N($R^{3b}$)$R^{3a}$ or —$S(O)_2R^{3a}$;

$R^{1d}$ represents a hydrogen atom, $C_1$-$C_6$ alkyl, $C_1$-$C_6$ haloalkyl, $C_1$-$C_4$ alkoxy ($C_1$-$C_4$) alkyl, $C_1$-$C_4$ haloalkoxy ($C_1$-$C_4$) alkyl, $C_1$-$C_4$ alkylthio ($C_1$-$C_4$) alkyl, $C_1$-$C_4$ alkylsulfonyl ($C_1$-$C_4$) alkyl, cyano ($C_1$-$C_6$) alkyl, $C_3$-$C_6$ cycloalkyl, $C_3$-$C_6$ cycloalkyl ($C_1$-$C_4$) alkyl, $C_3$-$C_6$ alkenyl, $C_3$-$C_6$ alkynyl, —C(O)$R^{3c}$, —C(O)$OR^{3c}$, —C(O)$SR^{3c}$, $C_1$-$C_6$ haloalkylthio or $C_1$-$C_6$ alkylsulfonyl, or represents that $R^{1c}$ may form a 5-7 membered ring with a nitrogen atom to be bonded, by forming a $C_4$-$C_6$ alkylene chain together with $R^{1d}$, and this alkylene chain may contain one oxygen atom, sulfur atom or nitrogen atom in this case and may be optionally substituted by a $C_1$-$C_6$ alkyl group, —CHO group, $C_1$-$C_6$ alkylcarbonyl group, $C_1$-$C_6$ haloalkylcarbonyl group, $C_1$-$C_6$ alkoxycarbonyl group, $C_1$-$C_6$ haloalkoxycarbonyl group, $C_1$-$C_6$ alkylaminocarbonyl group, $C_1$-$C_6$ haloalkylaminocarbonyl group, oxo group or thioxo group;

$R^{2a}$ represents a hydrogen atom, cyano, $C_1$-$C_6$ alkyl, $C_1$-$C_6$ haloalkyl, $C_1$-$C_6$ alkoxycarbonyl, —C(O)$NH_2$ or —C(S)$NH_2$;

$R^{2b}$ represents a hydrogen atom or $C_1$-$C_6$ alkyl, or represents that $R^{2b}$ may form a 3-6 membered ring with a carbon atom to be bonded, by forming a $C_2$-$C_5$ alkylene chain together with $R^{2a}$, and this alkylene chain may contain one to three oxygen atom(s), sulfur atom(s) or nitrogen atom(s) in this case;

$R^{2c}$ represents a hydrogen atom, $C_1$-$C_6$ alkyl, $C_1$-$C_6$ haloalkyl, $C_1$-$C_6$ alkylcarbonyl, $C_1$-$C_6$ haloalkylcarbonyl or $C_1$-$C_6$ alkoxycarbonyl;

$R^{3a}$ represents a $C_1$-$C_6$ alkyl, $C_1$-$C_6$ haloalkyl, ($C_1$-$C_4$) alkyl optionally substituted by $R^{4a}$, $C_3$-$C_6$ cycloalkyl, $C_3$-$C_6$ halocycloalkyl, E-1, E-2, E-4, $C_2$-$C_6$ alkenyl, $C_2$-$C_6$ haloalkenyl, $C_2$-$C_6$ alkynyl, phenyl, phenyl substituted by $(V)_{p1}$, D-3, D-4, D-12 to D-14, D-42 or D-43;

$R^{3b}$ represents a hydrogen atom or $C_1$-$C_6$ alkyl;

$R^{3c}$ represents a hydrogen atom, $C_1$-$C_4$ alkyl, $C_1$-$C_4$ haloalkyl, $C_3$-$C_6$ cycloalkyl ($C_1$-$C_4$) alkyl, $C_3$-$C_6$ cycloalkyl, $C_3$-$C_6$ alkenyl or $C_3$-$C_6$ alkynyl, or represents that $R^{3c}$ may form a 5-7 membered ring with a nitrogen atom, carbon atom, oxygen atom or sulfur atom to be bonded, by forming an ethylene chain or benzene ring bonded at an ortho-position together with $R^{3a}$;

$R^{4a}$ represents a halogen atom, cyano, nitro, $C_3$-$C_6$ cycloalkyl, $C_1$-$C_4$ alkoxy, $C_1$-$C_6$ alkoxycarbonyl, $S(O)_rR^{5a}$, D-42 or D-43;

$R^{5a}$ represents a $C_1$-$C_4$ alkyl;

V represents a halogen atom, cyano, nitro, $C_1$-$C_6$ alkyl, $C_1$-$C_6$ haloalkyl, —OH, $C_1$-$C_6$ alkoxy, $C_1$-$C_6$ haloalkoxy, $C_1$-$C_6$ alkylsulfonyloxy, $C_1$-$C_6$ haloalkylsulfonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —$NH_2$, $C_1$-$C_6$ alkylamino, di($C_1$-$C_6$ alkyl) amino, $C_1$-$C_6$ alkoxycarbonyl, —C(O)$NH_2$, $C_1$-$C_6$ alkylaminocarbonyl, $C_1$-$C_6$ haloalkylaminocarbonyl, di($C_1$-$C_6$ alkyl) aminocarbonyl, —C(S)$NH_2$, —$S(O)_2NH_2$, $C_1$-$C_6$ alkylaminosulfonyl or di($C_1$-$C_6$ alkyl) aminosulfonyl, and each V may be the same as or different from each other when p1 represents an integer of 2 or more;

moreover, when two Vs are adjacent, the two adjacent Vs may form a 5-membered ring or a 6-membered ring with carbon atoms bonding to each of the two Vs by forming —$OCH_2O$— or —$OCH_2CH_2O$—, and hydrogen atoms bonding to each carbon atom forming the ring may be optionally substituted by halogen atoms in this case;

$R^6$ represents a $C_1$-$C_6$ alkyl or $C_1$-$C_6$ haloalkyl;

$R^7$ represents a hydrogen atom or $C_1$-$C_6$ alkyl;

$R^8$ represents a halogen atom, cyano, amino, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)$R^{14}$, —C(O)$OR^{14}$, —C(O)$NH_2$, —C(O)N($R^{15}$)$R^{14}$, —C(S)$NH_2$, —C(S)N($R^{15}$)$R^{14}$, —C($R^7$)=NOH, —C($R^7$)=$NOR^6$, phenyl, phenyl substituted by $(Z)_{p1}$, D-1 to D-50 or E-1 to E-8;

D-1 to D-50 represent aromatic heterocyclic rings represented by the following structural formulae:
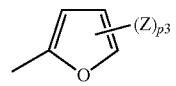 D-1
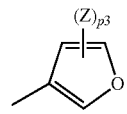 D-2
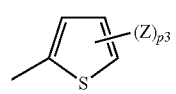 D-3
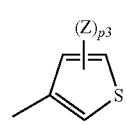 D-4
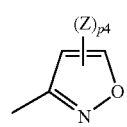 D-5
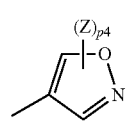 D-6
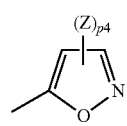 D-7
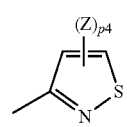 D-8
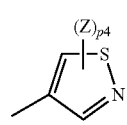 D-9
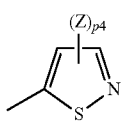 D-10
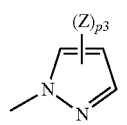 D-11
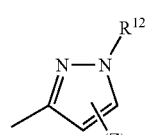 D-12
-continued
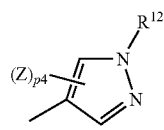 D-13
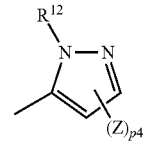 D-14
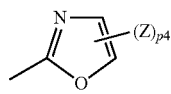 D-15
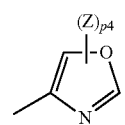 D-16
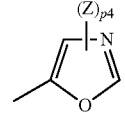 D-17
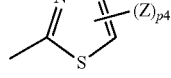 D-18
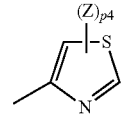 D-19
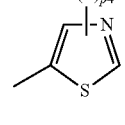 D-20
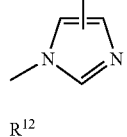 D-21
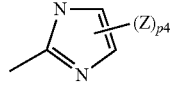 D-22
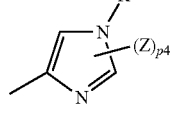 D-23
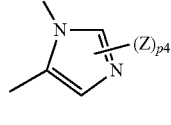 D-24

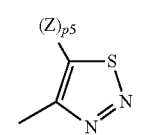 D-25
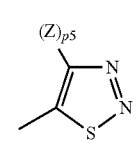 D-26
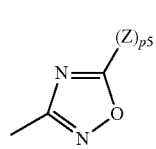 D-27
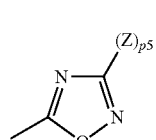 D-28
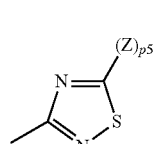 D-29
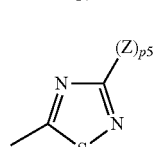 D-30
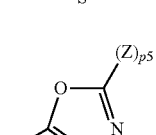 D-31
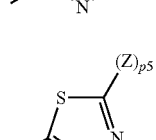 D-32
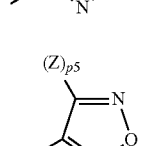 D-33
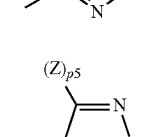 D-34
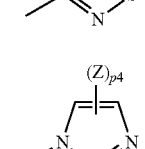 D-35
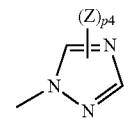 D-36
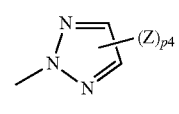 D-37
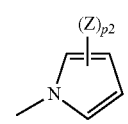 D-38
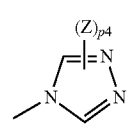 D-39
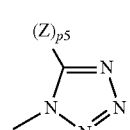 D-40
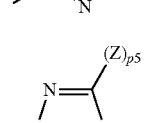 D-41
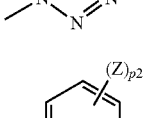 D-42
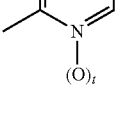 D-43
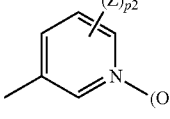 D-44
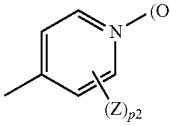 D-45
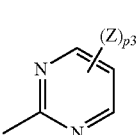 D-46
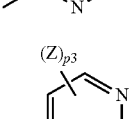 D-47
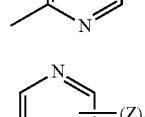

-continued

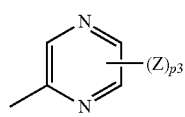
D-48

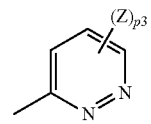
D-49

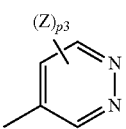
D-50

Z represents a halogen atom, cyano, nitro, amino, $C_1$-$C_6$ alkyl, ($C_1$-$C_6$) alkyl optionally substituted by $R^{16}$, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, —C(O)NH$_2$, —C(S)NH$_2$, —S(O)$_2$NH$_2$, —C(O)N(R$^{18}$)R$^{17}$, —C(S)N(R$^{18}$)R$^{17}$, $C_1$-$C_6$ alkylaminosulfonyl or di($C_1$-$C_6$ alkyl) aminosulfonyl, and each Z may be the same as or different from each other when p1, p2, p3 or p4 represents an integer of 2 or more;

E-1 to E-8 represent saturated heterocycles represented by the following structural formulae:

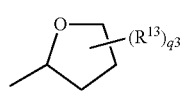
E-1

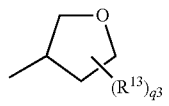
E-2

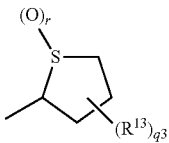
E-3

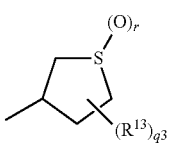
E-4

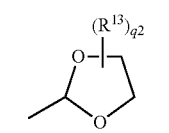
E-5

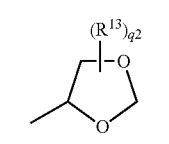
E-6

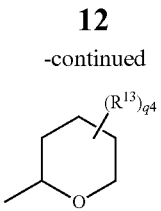
E-7

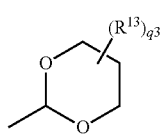
E-8

$R^9$ represents a $C_1$-$C_6$ alkyl, $C_1$-$C_6$ haloalkyl, $C_1$-$C_6$ alkoxy ($C_1$-$C_4$) alkyl, $C_1$-$C_6$ alkylthio ($C_1$-$C_4$) alkyl, $C_3$-$C_8$ cycloalkyl, $C_3$-$C_6$ alkenyl or $C_3$-$C_6$ alkynyl;

$R^{10}$ represents a $C_1$-$C_6$ haloalkyl, —C(O)R$^{14}$, —C(O)OR$^{14}$, phenyl, phenyl substituted by (Z)$_{p1}$, D-3, D-4, D-18, D-42, D-45, D-46, D-48 or D-49;

$R^{11}$ represents a hydrogen atom, $C_1$-$C_6$ alkyl or $C_3$-$C_6$ alkynyl;

$R^{12}$ represents a $C_1$-$C_6$ alkyl, phenyl or phenyl substituted by (Z)$_{p1}$;

$R^{13}$ represents a $C_1$-$C_4$ alkyl, and each $R^{13}$ may be the same as or different from each other when q1, q2, q3 or q4 represents an integer of 2 or more, and moreover represents that two $R^{13}$s may form oxo together when the two $R^{13}$s are bonded to the same carbon atom;

$R^{14}$ represents a $C_1$-$C_6$ alkyl, $C_1$-$C_6$ haloalkyl, $C_3$-$C_6$ cycloalkyl ($C_1$-$C_4$) alkyl, $C_3$-$C_6$ cycloalkyl, $C_3$-$C_6$ alkenyl or $C_3$-$C_6$ alkynyl;

$R^{15}$ represents a hydrogen atom or $C_1$-$C_6$ alkyl;

$R^{16}$ represents a —OH, $C_1$-$C_4$ alkoxy or $C_1$-$C_4$ alkylthio;

$R^{17}$ represents a hydrogen atom, $C_1$-$C_6$ alkyl, $C_3$-$C_6$ cycloalkyl, $C_3$-$C_6$ alkenyl, $C_3$-$C_6$ haloalkenyl, $C_3$-$C_6$ alkynyl, —C(R$^5$)=NOR$^{19}$, —C(O)OR$^{19}$, —C(O)NH$_2$, —C(O)N(R$^5$)R$^{19}$, —C(O)NHC(O)R$^{19}$, —C(O)N(R$^5$)C(O)OR$^{19}$, —N(R$^{21}$)R$^{20}$, phenyl substituted by (Z)$_{p1}$, D9 to D11, D18 to D20, D42 to D47 or D48;

$R^{18}$ represents a hydrogen atom, $C_1$-$C_6$ alkyl, $C_3$-$C_6$ alkynyl, —C(O)R$^{19a}$, —C(O)OR$^{19a}$ or $C_1$-$C_6$ haloalkylthio;

$R^{19}$ represents a $C_1$-$C_6$ alkyl, $C_1$-$C_6$ haloalkyl or $C_2$-$C_6$ alkenyl;

$R^{19a}$ represents a $C_1$-$C_6$ alkyl, $C_1$-$C_6$ haloalkyl, $C_1$-$C_4$ alkoxy ($C_1$-$C_4$) alkyl, $C_1$-$C_4$ alkylthio ($C_1$-$C_4$) alkyl, $C_1$-$C_4$ alkylsulfinyl ($C_1$-$C_4$) alkyl, $C_1$-$C_4$ alkylsulfonyl ($C_1$-$C_4$) alkyl, $C_3$-$C_6$ cycloalkyl, $C_2$-$C_6$ alkenyl, $C_1$-$C_6$ alkoxycarbonyl, phenyl, phenyl substituted by (Z)$_{p1}$, D42, D43 or D44;

$R^{20}$ represents a $C_1$-$C_6$ haloalkyl, $C_1$-$C_6$ alkoxycarbonyl, phenyl, phenyl substituted by (Z)$_{p1}$, D42 to D46 or D47;

$R^{21}$ represents a hydrogen atom, $C_1$-$C_6$ alkyl, $C_3$-$C_6$ alkenyl or $C_3$-$C_6$ alkynyl;

$L^2$ represents a single bond or $C_1$-$C_6$ alkylene chain;

$Q^2$ represents a hydrogen atom, $C_1$-$C_6$ haloalkyl, $C_2$-$C_6$ alkynyl, —N(R$^{23}$)R$^{22}$, —C(O)N(R$^{23}$)R$^{22}$, phenyl, phenyl substituted by (Z)$_{p1}$, D18 to D20, D42 to D46 or D47;

$R^{22}$ represents a $C_1$-$C_6$ alkyl, $C_1$-$C_6$ haloalkyl, $C_3$-$C_6$ cycloalkyl, $C_3$-$C_6$ alkenyl, $C_3$-$C_6$ alkynyl, phenyl or phenyl substituted by (Z)$_{p1}$;

$R^{23}$ represents a hydrogen atom or $C_1$-$C_6$ alkyl;

p1 represents an integer of 1 to 5;
p2 represents an integer of 0 to 4;
p3 represents an integer of 0 to 3;
p4 represents an integer of 0 to 2;
p5 represents an integer of 0 or 1;
q2 represents an integer of 0 to 5;

q3 represents an integer of 0 to 7;
q4 represents an integer of 0 to 9;
r represents an integer of 0 to 2;
t represents an integer of 0 or 1) and hydroxylamine in an aliphatic or an aromatic hydrocarbon solvent which may be substituted by a halogen atom by adding an additive selected from a phase-transfer catalyst, a $C_1$-$C_6$ alcohol and an aprotic polar solvent in the presence of a base and water.

[2] The method for producing according to [1], the additive is a phase-transfer catalyst.

[3] The method for producing according to [1], the additive is a $C_1$-$C_6$ alcohol.

[4] The method for producing according to [1], the additive is an aprotic polar solvent.

[5] The method for producing according to [1] to [4], the 1,3-bis(substituted phenyl)-3-substituted-2-propen-1-one compound represented by Formula (2) and produced by reacting, in the presence of a dehydration agent and a base, 1,3-bis(substituted phenyl)-3-substituted-3-hydroxypropan-1-one compound represented by Formula (3):

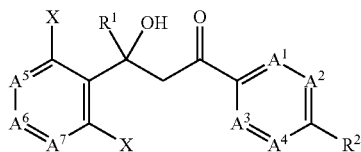

(where $R^1$, $R^2$, X, $A^1$, $A^2$, $A^3$, $A^4$, $A^5$, $A^6$ and $A^7$ represent the same meaning as described above) is used.

[6] A method for producing a 1,3-bis(substituted phenyl)-3-substituted-2-propen-1-one compound represented by Formula (2) includes reacting a 1,3-bis(substituted phenyl)-3-substituted-3-hydroxypropan-1-one compound represented by Formula (3) in the presence of a dehydration agent and a base.

[7] The method for producing according to [5] or [6], the 1,3-bis(substituted phenyl)-3-substituted-3-hydroxypropan-1-one compound is used that is represented by Formula (3) and produced by reacting an aromatic ketone compound represented by Formula (4):

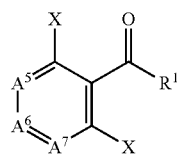

(where $R^1$, X, $A^5$, $A^6$ and $A^7$ represent the same meaning as described above) and a substituted acetophenone compound represented by Formula (5):

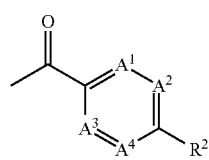

(where $R^2$, $A^1$, $A^2$, $A^3$ and $A^4$ represent the same meaning as described above) in a suspended state in the presence or absence of an additive and in the presence of a base in a solvent.

[8] A method for producing a 1,3-bis(substituted phenyl)-3-substituted-3-hydroxypropan-1-one compound represented by Formula (3) is characterized by reacting an aromatic ketone compound represented by Formula (4) and a substituted acetophenone compound represented by Formula (5) in a suspended state in the presence or absence of an additive and in the presence of a base in a solvent.

[9] The method for producing according to [8] is characterized in that the solvent is an organic solvent and the reaction is conducted in the absence of the additive.

[10] The method for producing according to [8] is characterized in that the solvent is water and the reaction is conducted in the presence of a water-soluble organic solvent as the additive.

[11] The method for producing according to [8] is characterized in that the solvent is water and the reaction is conducted in the presence of a surfactant as the additive.

[12] A method for producing a 1,3-bis(substituted phenyl)-3-substituted-2-propen-1-one compound represented by Formula (2) in one step includes reacting an aromatic ketone compound represented by Formula (4) and a substituted acetophenone compound represented by Formula (5) in an organic solvent, in the presence of a base, at a temperature of over 80° C.

[13] A compound represented by Formula (2), wherein $R^1$, X, $A^1$, $A^2$, $A^3$, $A^4$, $A^5$, $A^6$ and $A^7$ represent the same meaning as described above, and $R^2$ represents a substituent selected from the —S(O)$_r$-L$^2$-Q$^2$ and D-1 to D-50.

[14] A compound represented by Formula (3), wherein $R^1$, X, $A^1$, $A^2$, $A^3$, $A^4$, $A^5$, $A^6$ and $A^7$ represent the same meaning as described above, and $R^2$ represents a substituent selected from the —S(O)$_r$-L$^2$-Q$^2$ and D-1 to D-50.

[15] A compound represented by Formula (2), wherein $R^1$, X, $A^5$, $A^6$ and $A^7$ represent the same meaning as described above, and at least one of $A^1$, $A^2$, $A^3$ and $A^4$ is N, and $R^2$ is a halogen atom.

[16] A compound represented by Formula (3), wherein $R^1$, X, $A^5$, $A^6$ and $A^7$ represent the same meaning as described above, and at least one of $A^1$, $A^2$, $A^3$ and $A^4$ is N, and $R^2$ is a halogen atom.

Effects of the Invention

By the method for production according to the present invention, a 1,3-bis(substituted phenyl)-3-substituted-3-hydroxypropan-1-one compound and a 1,3-bis(substituted phenyl)-3-substituted-2-propen-1-one compound which are useful for synthesizing a production intermediate of functional materials of medical drugs, agricultural chemicals, electronic materials or the like can be produced in high yield and high selectivity, in a solvent such as water and toluene which is easy to use in industry, by utilizing an aromatic ketone compound and a substituted acetophenone compound as starting raw materials by adequately selecting a surfactant, a dehydration agent and a base. Therefore the present invention can provide methods useful for industrial production.

Moreover, the present invention can provide methods for producing agricultural chemicals, particularly an isoxazoline compound described in WO 05/085216 pamphlet which has excellent insecticidal-miticidal activity to harmful insects for agriculture, spider mites, external or internal parasitic insects of mammals and birds and its production intermediate.

BEST MODES FOR CARRYING OUT THE INVENTION

The compound described in the present specification has E-form and Z-form geometric isomers depending on their substituents. However, the present invention includes these E-form, Z-form or E-form, and Z-form in any ratio. Moreover, the compound described in the present specification has an optically active substance generated by the presence of one or more asymmetric carbon atom(s), and the compound described in the present specification includes every optically active substance or racemic substance.

Among the compounds described in the present specification, examples of compounds which can produce acid addition salts by common methods include salts of hydrohalic acids such as hydrofluoric acid, hydrochloric acid, hydrobromic acid and hydroiodic acid; salts of inorganic acids such as nitric acid, sulfuric acid, phosphoric acid, chloric acid and perchloric acid; salts of sulfonic acids such as methanesulfonic acid, ethanesulfonic acid, trifluoromethanesulfonic acid, benzenesulfonic acid and p-toluenesulfonic acid; salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid; or salts of amino acids such as glutamic acid and asparaginic acid.

Among the compounds described in the present specification, examples of compounds which can produce metal salts by common methods include salts of alkali metals such as lithium, sodium and potassium; salts of alkaline earth metals such as calcium, barium and magnesium; or salts of aluminum.

Among the compounds described in the present specification, examples of compounds which can produce amine salts by common methods include salts of ammonia, methylamine, ethylamine, propylamine, butylamine, pentylamine, benzylamine, aniline, dimethylamine, diethylamine, dipropylamine, dibutylamine, dipentylamine, pyrrolidine, piperidine, piperazine, morpholine, dibenzylamine, trimethylamine, triethylamine, tripropylamine, tributylamine, tripentylamine and tribenzylamine.

Next, specific examples of each substituent described in the present specification will be described below. Here, n-, i-, s- and t-mean normal, iso, secondary and tertiary, respectively, and ph means phenyl.

Halogen atoms in the compounds described in the present specification include a fluorine atom, a chlorine atom, a bromine atom and an iodine atom. Here, the expression "halo" in the present specification also represents these halogen atoms.

The expression $C_a$-$C_b$ alkyl in the present specification represents hydrocarbon groups of linier chains or branched chains having a to b pieces of carbon atoms. Specific examples include a methyl group, ethyl group, n-propyl group, i-propyl group, n-butyl group, i-butyl group, s-butyl group, t-butyl group, n-pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group, n-hexyl group, 1-methylpentyl group, 2-methylpentyl group, 1,1-dimethylbutyl group, 1,3-dimethylbutyl group, heptyl group, octyl group, nonyl group, decyl group, undecyl group and dodecyl group. Each of the groups is selected within the range of each specified number of carbon atoms.

Specific examples of the expression of aromatic heterocyclic groups in the present specification include a 2-thienyl group, 3-thienyl group, 2-furyl group, 3-furyl group, 2-pyranyl group, 3-pyranyl group, 4-pyranyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzothienyl group, 3-benzothienyl group, 4-benzothienyl group, 5-benzothienyl group, 6-benzothienyl group, 7-benzothienyl group, 1-isobenzothienyl group, 4-isobenzothienyl group, 5-isobenzothienyl group, 2-chromenyl group, 3-chromenyl group, 4-chromenyl group, 5-chromenyl group, 6-chromenyl group, 7-chromenyl group, 8-chromenyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 2-thiazolyl group, 4-thiazolyl group, 5-thiazolyl group, 3-isothiazolyl group, 4-isothiazolyl group, 5-isothiazolyl group, 2-oxazolyl group, 4-oxazolyl group, 5-oxazolyl group, 3-isoxazolyl group, 4-isoxazolyl group, 5-isoxazolyl group, 2-pyridyl group, 3-pyridyl group, 4-pyridyl group, 2-pyrazinyl group, 2-pyrimidinyl group, 4-pyrimidinyl group, 5-pyrimidinyl group, 3-pyridazinyl group, 4-pyridazinyl group, 1-indolizinyl group, 2-indolizinyl group, 3-indolizinyl group, 5-indolizinyl group, 6-indolizinyl group, 7-indolizinyl group, 8-indolizinyl group, 1-isoindolyl group, 4-isoindolyl group, 5-isoindolyl group, 1-indolyl group, 2-indolyl group, 3-indolyl group, 4-indolyl group, 5-indolyl group, 6-indolyl group, 7-indolyl group, 1-indazolyl group, 2-indazolyl group, 3-indazolyl group, 4-indazolyl group, 5-indazolyl group, 6-indazolyl group, 7-indazolyl group, 1-purinyl group, 2-purinyl group, 3-purinyl group, 6-purinyl group, 7-purinyl group, 8-purinyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 1-phthalazinyl group, 5-phthalazinyl group, 6-phthalazinyl group, 2-naphthyridinyl group, 3-naphthyridinyl group, 4-naphthyridinyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group, 3-cinnolinyl group, 4-cinnolinyl group, 5-cinnolinyl group, 6-cinnolinyl group, 7-cinnolinyl group, 8-cinnolinyl group, 2-pteridinyl group, 4-pteridinyl group, 6-pteridinyl group and 7-pteridinyl group and 3-furazanyl group.

Specific examples of the expression of aryl groups in the present specification include a phenyl group, naphthyl group, anthryl and the above-described aromatic heterocyclic groups.

Examples of heterocyclic groups in the present specification include a 2-tetrahydrofuranyl group, 3-tetrahydrofuranyl group, 2-tetrahydropyranyl group, 3-tetrahydropyranyl group, 4-tetrahydropyranyl group, 1-pyrrolidinyl group, 2-pyrrolidinyl group, 3-pyrrolidinyl group, 1-pyrrolinyl group, 2-pyrrolinyl group, 3-pyrrolinyl group, 4-pyrrolinyl group, 5-pyrrolinyl group, 1-imidazolidinyl group, 2-imidazolidinyl group, 4-imidazolidinyl group, 1-imidazolinyl group, 2-imidazolinyl group, 4-imidazolinyl group, 1-pyrazolidinyl group, 3-pyrazolidinyl group, 4-pyrazolidinyl group, 1-pyrazolinyl group, 2-pyrazolinyl group, 3-pyrazolinyl group, 4-pyrazolinyl group, 5-pyrazolinyl group, 1-piperidyl group, 2-piperidyl group, 3-piperidyl group, 4-piperidyl group, 1-piperazinyl group, 2-piperazinyl group, 3-piperazinyl group, 1-indolinyl group, 2-indolinyl group, 3-indolinyl group, 4-indolinyl group, 5-indolinyl group, 6-indolinyl group, 7-indolinyl group, 1-isoindolinyl group, 2-isoindolinyl group, 4-isoindolinyl group, 5-isoindolinyl group, 2-quinuclidinyl group, 3-quinuclidinyl group, 4-quinuclidinyl group, 2-morpholinyl group, 3-morpholinyl group, 4-morpholinyl group, 1-azetidinyl group, 2-azetidinyl group, 3-azetidinyl group, 1-azetidinonyl group, 3-azetidinonyl group and 4-azetidinonyl group, other than the above-described aromatic heterocyclic groups.

The expression $C_a$-$C_b$ haloalkyl in the present specification represents hydrocarbon groups of linier chains or branched chains having a to b pieces of carbon atoms in which hydrogen atom(s) bonding to carbon atom(s) is optionally substituted by halogen atom(s). In this case, these halogen atoms may be the same as or different from each other, when the alkyl group is substituted by 2 or more halogen atoms. Specific examples include a fluoromethyl group, chloromethyl group, bromomethyl group, iodomethyl group, difluoromethyl group, chlorofluoromethyl, dichloromethyl group, bromofluoromethyl group, trifluoromethyl group, chlorodifluoromethyl group, dichlorofluoromethyl group, trichloromethyl group, bromodifluoromethyl group, bromochlorofluoromethyl group, dibromofluoromethyl group, 2-fluoroethyl group, 2-chloroethyl group, 2-bromoethyl group, 2,2-difluoroethyl group, 2-chloro-2-fluoroethyl group, 2,2-dichloroethyl group, 2-bromo-2-fluoroethyl group, 2,2,2-trifluoroethyl group, 2-chloro-2,2-difluoroethyl group, 2,2-dichloro-2-fluoroethyl group, 2,2,2-trichloroethyl group, 2-bromo-2,2-difluoroethyl group, 2-bromo-2-chloro-2-fluoroethyl group, 2-bromo-2,2-dichloroethyl group, 1,1,2,2-tetrafluoroethyl group, pentafluoroethyl group, 1-chloro-1,2,2,2-tetrafluoroethyl group, 2-chloro-1,1,2,2-tetrafluoroethyl group, 1,2-dichloro-1,2,2-trifluoroethyl group, 2-bromo-1,1,2,2-tetrafluoroethyl group, 2-fluoropropyl group, 2-chloropropyl group, 2-bromopropyl group, 2-chloro-2-fluoropropyl group, 2,3-dichloropropyl group, 2-bromo-3-fluoropropyl group, 3-bromo-2-chloropropyl group, 2,3-dibromopropyl group, 3,3,3-trifluoropropyl group, 3-bromo-3,3-difluoropropyl group, 2,2,3,3-tetrafluoropropyl group, 2-chloro-3,3,3-trifluoropropyl group, 2,2,3,3,3-pentafluoropropyl group, 1,1,2,3,3,3-hexafluoropropyl group, heptafluoropropyl group, 2,3-dichloro-1,1,2,3,3-pentafluoropropyl group, 2-fluoro-1-methylethyl group, 2-chloro-1-methylethyl group, 2-bromo-1-methylethyl group, 2,2,2-trifluoro-1-(trifluoromethyl)ethyl group, 1,2,2,2-tetrafluoro-1-(trifluoromethyl)ethyl group, 2-fluorobutyl group, 2-chlorobutyl group, 2,2,3,3,4,4-hexafluorobutyl group, 2,2,3,4,4,4-hexafluorobutyl group, 2,2,3,3,4,4-hexafluorobutyl group, 2,2,3,3,4,4,4-heptafluorobutyl group, 1,1,2,2,3,3,4,4-octafluorobutyl group, nonafluorobutyl group, 4-chloro-1,1,2,2,3,3,4,4-octafluorobutyl group, 2-fluoro-2-methylpropyl group, 1,2,2,3,3,3-hexafluoro-1-(trifluoromethyl)propyl group, 2-chloro-1,1-dimethylethyl group, 2-bromo-1,1-dimethylethyl group, 5-chloro-2,2,3,4,4,5,5-heptafluoropentyl group, and tridecafluorohexyl group. Each of the groups is selected within the range of each specified number of carbon atoms.

The expression cyano ($C_a$-$C_b$) alkyl in the present specification represents alkyl groups of linier chains or branched chains having a to b pieces of carbon atoms in which hydrogen atom(s) bonding to carbon atom(s) is optionally substituted by a cyano group. Specific examples include, a cyanomethyl group, 1-cyanoethyl group, 2-cyanoethyl group, 2-cyanopropyl group, 3-cyanopropyl group and 2-cyanobutyl group. Each of the groups is selected within the range of each specified number of carbon atoms.

The expression $C_a$-$C_b$ cycloalkyl in the present specification represents cyclic hydrocarbon groups having a to b pieces of carbon atoms, and can form a 3-membered ring to a 6-membered ring of monocyclic or composite ring structures. In addition, each ring may be optionally substituted by an alkyl group within a range of each specified number of carbon atoms. Specific examples include a cyclopropyl group, 1-methylcyclopropyl group, 2-methylcyclopropyl group, 2,2-dimethylcyclopropyl group, 2,2,3,3-tetramethylcyclopropyl group, cyclobutyl group, cyclopentyl group, 2-methylcyclopentyl group, 3-methylcyclopentyl group, cyclohexyl group, 2-methylcyclohexyl group, 3-methylcyclohexyl group, 4-methylcyclohexyl group and bicyclo(2.2.1)heptane-2-yl group. Each of the groups is selected with the range of each specified number of carbon atoms.

The expression $C_a$-$C_b$ halocycloalkyl in the present specification represents cyclic hydrocarbon groups having a to b pieces of carbon atoms in which hydrogen atom(s) bonding to carbon atom(s) is optionally substituted by halogen atom(s), and can form a 3-membered ring to a 6-membered ring of monocyclic or composite ring structures. In addition, each ring may be optionally substituted by an alkyl group within a range of each specified number of carbon atoms, and a ring structure part, a side chain part or both of them may be substituted by halogen atom(s). Moreover, these halogen atoms may be the same as or different from each other, when the cycloalkyl group is substituted by 2 or more halogen atoms. Specific examples include a 2,2-difluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 2,2,3,3-tetrafluorocyclobutyl group, 2-(trifluoromethyl)cyclohexyl group, 3-(trifluoromethyl)cyclohexyl group and 4-(trifluoromethyl)cyclohexyl group. Each of the groups is selected within the range of each specified number of carbon atoms.

The expression $C_a$-$C_b$ alkenyl in the present specification represents unsaturated hydrocarbon groups of linier chains or branched chains having a to b pieces of carbon atoms and having one or more double bond(s) in the molecule. Specific examples include a vinyl group, 1-propenyl group, 2-propenyl group, 1-methylethenyl group, 2-butenyl group, 1-methyl-2-propenyl group, 2-methyl-2-propenyl group, 2-pentenyl group, 2-methyl-2-butenyl group, 3-methyl-2-butenyl group, 2-ethyl-2-propenyl group, 1,1-dimethyl-2-propenyl group, 2-hexenyl group, 2-methyl-2-pentenyl group, 2,4-dimethyl-2,6-heptadienyl group and 3,7-dimethyl-2,6-octadienyl group. Each of the groups is selected within the range of each specified number of carbon atoms.

The expression $C_a$-$C_b$ haloalkenyl in the present specification represents unsaturated hydrocarbon groups of linier chains or branched chains having a to b pieces of carbon atoms in which hydrogen atom(s) bonding to carbon atom(s) is optionally substituted by halogen atom(s) and having one or more double bond(s) in the molecule. In this case, these halogen atoms may be the same as or different from each other, when the alkenyl group is substituted by 2 or more halogen atoms. Specific examples include a 2,2-dichlorovinyl group, 2-fluoro-2-propenyl group, 2-chloro-2-propenyl group, 3-chloro-2-propenyl group, 2-bromo-2-propenyl group, 3-bromo-2-propenyl group, 3,3-difluoro-2-propenyl group, 2,3-dichloro-2-propenyl group, 3,3-dichloro-2-propenyl group, 2,3-dibromo-2-propenyl group, 2,3,3-trifluoro-2-propenyl group, 2,3,3-trichloro-2-propenyl group, 1-(trifluoromethyl) ethenyl group, 3-chloro-2-butenyl group, 3-bromo-2-butenyl group, 4,4-difluoro-3-butenyl group, 3,4,4-trifluoro-3-butenyl group, 3-chloro-4,4,4-trifluoro-2-butenyl group and 3-bromo-2-methyl-2-propenyl group. Each of the groups is selected within the range of each specified number of carbon atoms.

The expression $C_a$-$C_b$ alkynyl in the present specification represents unsaturated hydrocarbon groups of linier chains or branched chains having a to b pieces of carbon atoms and having one or more triple bond(s) in the molecule. Specific examples include an ethynyl group, 1-propynyl group, 2-propynyl group, 2-butynyl group, 1-methyl-2-propynyl group, 2-pentynyl group, 1-methyl-2-butynyl group, 1,1-dimethyl-2-propynyl group and 2-hexynyl group. Each of the groups is selected within the range of each specified number of carbon atoms.

The expression $C_a$-$C_b$ alkoxy in the present specification represents alkyl-O— groups, in which the alkyl has a to b pieces of carbon atoms as defined above. Specific examples include a methoxy group, ethoxy group, n-propyloxy group, i-propyloxy group, n-butyloxy group, i-butyloxy group, s-butyloxy group, t-butyloxy group, n-pentyloxy group and n-hexyloxy group. Each of the groups is selected within the range of each specified number of carbon atoms.

The expression $C_a$-$C_b$ haloalkoxy in the present specification represents haloalkyl-O-groups, in which the haloalkyl has a to b pieces of carbon atoms as defined above. Specific examples include a difluoromethoxy group, trifluoromethoxy group, chlorodifluoromethoxy group, bromodifluoromethoxy group, 2-fluoroethoxy group, 2-chloroethoxy group, 2,2,2-trifluoroethoxy group, 1,1,2,2-tetrafluoroethoxy group, 2-chloro-1,1,2-trifluoroethoxy group, 2-bromo-1,2,2-trifluoroethoxy group, pentafluoroethoxy group, 2,2-dichloro-1,1,2-trifluoroethoxy group, 2,2,2-trichloro-1,1-difluoroethoxy group, 2-bromo-1,1,2,2-tetrafluoroethoxy group, 2,2,3,3-tetrafluoropropyloxy group, 1,1,2,3,3,3-hexafluoropropyloxy group, 2,2,2-trifluoro-1-(trifluoromethyl)ethoxy group, heptafluoropropyloxy group and 2-bromo-1,1,2,3,3,3-hexafluoropropyloxy group. Each of the groups is selected within the range of each specified number of carbon atoms.

The expression $C_a$-$C_b$ alkylthio in the present specification represents alkyl-S— groups, in which the alkyl has a to b pieces of carbon atoms as defined above. Specific examples include a methylthio group, ethylthio group, n-propylthio group, i propylthio group, n-butylthio group, i-butylthio group, s-butylthio group, t-butylthio group, n-pentylthio group and n-hexylthio group. Each of the groups is selected within the range of each specified number of carbon atoms.

The expression $C_a$-$C_b$ haloalkylthio in the present specification represents haloalkyl-S-groups, in which the haloalkyl has a to b pieces of carbon atoms as defined above. Specific examples include a difluoromethylthio group, trifluoromethylthio group, chlorodifluoromethylthio group, bromodifluoromethylthio group, 2,2,2-trifluoroethylthio group, 1,1,2,2-tetrafluoroethylthio group, 2-chloro-1,1,2-trifluoroethylthio group, pentafluoroethylthio group, 2-bromo-1,1,2,2-tetrafluoroethylthio group, 1,1,2,3,3,3-hexafluoropropylthio group, heptafluoropropylthio group, 1,2,2,2-tetrafluoro-1-(trifluoromethyl)ethylthio group and nonafluorobutylthio group. Each of the groups is selected within the range of each specified number of carbon atoms.

The expression $C_a$-$C_b$ alkylsulfinyl in the present specification represents alkyl-S(O)-groups, in which the alkyl has a to b pieces of carbon atoms as defined above. Specific examples include a methylsulfinyl group, ethylsulfinyl group, n-propylsulfinyl group, i-propylsulfinyl group, n-butylsulfinyl group, i-butylsulfinyl group, s-butylsulfinyl group and t-butylsulfinyl group. Each of the groups is selected within the range of each specified number of carbon atoms.

The expression $C_a$-$C_b$ haloalkylsulfinyl in the present specification represents haloalkyl-S(O)-groups, in which the haloalkyl has a to b pieces of carbon atoms as defined above. Specific examples include a difluoromethylsulfinyl group, trifluoromethylsulfinyl group, chlorodifluoromethylsulfinyl group, bromodifluoromethylsulfinyl group, 2,2,2-trifluoroethylsulfinyl group, 2-bromo-1,1,2,2-tetrafluoroethylsulfinyl group, 1,2,2,2-tetrafluoro-1-(trifluoromethyl)ethylsulfinyl group and nonafluorobutylsulfinyl group. Each of the groups is selected within the range of each specified number of carbon atoms.

The expression $C_a$-$C_b$ alkylsulfonyl in the present specification represents alkyl-$SO_2$-groups, in which the alkyl has a to b pieces of carbon atoms as defined above. Specific examples include a methylsulfonyl group, ethylsulfonyl group, n-propylsulfonyl group, i-propylsulfonyl group, n-butylsulfonyl group, i-butylsulfonyl group, s-butylsulfonyl group, t-butylsulfonyl group, n-pentylsulfonyl group and n-hexylsulfonyl group. Each of the groups is selected within the range of each specified number of carbon atoms.

The expression $C_a$-$C_b$ haloalkylsulfonyl in the present specification represents haloalkyl-$SO_2$-groups, in which the haloalkyl has a to b pieces of carbon atoms as defined above. Specific examples include a difluoromethylsulfonyl group, trifluoromethylsulfonyl group, chlorodifluoromethylsulfonyl group, bromodifluoromethylsulfonyl group, 2,2,2-trifluoroethylsulfonyl group, 1,1,2,2-tetrafluoroethylsulfonyl group, 2-chloro-1,2,2-trifluoroethylsulfonyl group and 2-bromo-1,1,2,2-tetrafluoroethylsulfonyl group. Each of the groups is selected within the range of each specified number of carbon atoms.

The expression $C_a$-$C_b$ alkylcarbonyl in the present specification represents alkyl-C(O)-groups, in which the alkyl has a to b pieces of carbon atoms as defined above. Specific examples include an acetyl group, propionyl group, butyryl group, isobutyryl group, valeryl group, isovaleryl group, 2-methylbutanoyl group, pivaloyl group, hexanoyl group and heptanoyl group. Each of the groups is selected within the range of each specified number of carbon atoms.

The expression $C_a$-$C_b$ haloalkylcarbonyl in the present specification represents haloalkyl-C(O)-groups, in which the haloalkyl has a to b pieces of carbon atoms as defined above. Specific examples include a fluoroacetyl group, chloroacetyl group, difluoroacetyl group, dichloroacetyl group, trifluoroacetyl group, chlorodifluoroacetyl group, bromodifluoroacetyl group, trichloroacetyl group, pentafluoropropionyl group, heptafluorobutanoyl group and 3-chloro-2,2-dimethylpropanoyl group. Each of the groups is selected within the range of each specified number of carbon atoms.

The expression $C_a$-$C_b$ alkoxycarbonyl in the present specification represents alkyl-O—C(O)-groups, in which the alkyl has a to b pieces of carbon atoms as defined above. Specific examples include a methoxycarbonyl group, ethoxycarbonyl group, n-propyloxycarbonyl group, i-propyloxycarbonyl group, n-butoxycarbonyl group, i-butoxycarbonyl group and t-butoxycarbonyl group. Each of the groups is selected within the range of each specified number of carbon atoms.

The expression $C_a$-$C_b$ alkylthiocarbonyl in the present specification represents alkyl-S—C(O)-groups, in which the alkyl has a to b pieces of carbon atoms as defined above. Specific examples include a methylthio-C—(O)— group, ethylthio-C—(O)— group, n-propylthio-C—(O)— group, i-propylthio-C—(O)— group, n-butylthio-C—(O)— group, i-butylthio-C—(O)— group and t-butylthio-C—(O)— group. Each of the groups is selected within the range of each specified number of carbon atoms.

The expression $C_a$-$C_b$ alkoxythiocarbonyl in the present specification represents alkyl-O—C(S)-groups, in which the alkyl has a to b pieces of carbon atoms as defined above. Specific examples include a methoxy-C(S)— group, ethoxy-C(S)— group, n-propyloxy-C(S)— group and i-propyloxy-C(S)— group. Each of the groups is selected within the range of each specified number of carbon atoms.

The expression $C_a$-$C_b$ alkyldithiocarbonyl in the present specification represents alkyl-S—C(S)-groups, in which the alkyl has a to b pieces of carbon atoms as defined above. Specific examples include a methylthio-C(S)— group, ethylthio-C(S)— group, n-propylthio-C(S)— group and i-propylthio-C(S)— group. Each of the groups is selected within the range of each specified number of carbon atoms.

The expression $C_a$-$C_b$ alkylaminocarbonyl in the present specification represents carbamoyl groups whose one hydrogen atom is substituted by an alkyl group, in which the alkyl has a to b pieces of carbon atoms as defined above. Specific examples include a methylcarbamoyl group, ethylcarbamoyl group, n-propylcarbamoyl group, i-propylcarbamoyl group, n-butylcarbamoyl group, i-butylcarbamoyl group, s-butylcarbamoyl group, and t-butylcarbamoyl group. Each of the groups is selected within the range of each specified number of carbon atoms.

The expression di($C_a$-$C_b$ alkyl) aminocarbonyl in the present specification represents carbamoyl groups whose both hydrogen atoms are substituted by alkyl groups which may be the same as or different from each other and have a to b pieces of carbon atoms as defined above. Specific examples include an N,N-dimethylcarbamoyl group, N-ethyl-N-methylcarbamoyl group, N,N-diethylcarbamoyl group, N,N-di-n-propylcarbamoyl group and N,N-di-n-butylcarbamoyl group. Each of the groups is selected within the range of each specified number of carbon atoms.

The expression $C_a$-$C_b$ alkylaminosulfonyl in the present specification represents sulfamoyl group whose one hydrogen atom is substituted by an alkyl group which has a to b pieces of carbon atoms as defined above. Specific examples include a methylsulfamoyl group, ethylsulfamoyl group, n-propylsulfamoyl group, i-propylsulfamoyl group, n-butylsulfamoyl group, i-butylsulfamoyl group, s-butylsulfamoyl group and t-butylsulfamoyl group. Each of the groups is selected within the range of each specified number of carbon atoms.

The expression di($C_a$-$C_b$ alkyl) aminosulfonyl in the present specification represents sulfamoyl groups whose both hydrogen atoms are substituted by alkyl groups which may be the same as or different from each other and have a to b pieces of carbon atoms as defined above. Specific examples include an N,N-dimethylsulfamoyl group, N-ethyl-N-methylsulfamoyl group, N,N-diethylsulfamoyl group, N,N-di-n-propylsulfamoyl group and N,N-di-n-butylsulfamoyl group. Each of the groups is selected within the range of each specified number of carbon atoms.

The expression $C_a$-$C_b$ cycloalkyl($C_d$-$C_e$) alkyl, $C_a$-$C_b$ alkoxy($C_d$-$C_e$) alkyl or $C_a$-$C_b$ alkylthio($C_d$-$C_e$) alkyl in the present specification represents a hydrocarbon group of liner chains or branched chains whose hydrogen atoms bonding to carbon atoms are optionally substituted by a $C_a$-$C_b$ cycloalkyl group, $C_a$-$C_b$ alkoxy group or $C_a$-$C_b$ alkylthio group as defined above, and whose number of substituted carbon atoms is d-e. Each of the groups is selected within the range of each specified number of carbon atoms.

The expression ($C_a$-$C_b$) alkyl optionally substituted by $R^8$ in the present specification represents hydrocarbon groups of linier chains or branched chains, whose hydrogen atoms bonding to carbon atom(s) is optionally substituted by any $R^8$, and whose number of substituted carbon atoms is a-b. Each of the groups is selected within the range of each specified number of carbon atoms. In this case, these $R^8$s may be the same as or different from each other, when the substituent $R^8$ on each ($C_a$-$C_b$) alkyl groups are 2 or more.

The expression hydroxy ($C_d$-$C_e$) haloalkyl, $C_a$-$C_b$ alkoxy ($C_d$-$C_e$) haloalkyl or $C_a$-$C_b$ haloalkoxy ($C_d$-$C_e$) haloalkyl in the present specification represents haloalkyl groups whose hydrogen atoms or halogen atoms bonding to carbon atoms are optionally substituted by any $C_a$-$C_b$ alkoxy group, $C_a$-$C_b$ haloalkoxy group or hydroxy group as defined above, and whose number of substituted carbon atoms is d-e. Specific examples include a 2,2,2-trifluoro-1-hydroxy-1-(trifluoromethyl)ethyl group, difluoro(methoxy)methyl group, 2,2,2-trifluoro-1-methoxy-1-(trifluoromethyl)ethyl group, difluoro(2,2,2-trifluoroethoxy)methyl group, 2,2,2-trifluoro-1-(2,2,2-trifluoroethoxy)-1-(trifluoromethyl)ethyl group, and 3-(1,2-dichloro-1,2,2-trifluoroethoxy)-1,1,2,2,3,3-hexafluoropropyl group. Each of the groups is selected within the range of each specified number of carbon atoms.

In the compounds described in the present specification, examples of a substituent represented by X preferably include a halogen atom and $C_1$-$C_4$ haloalkyl, and more preferably include a chlorine atom, bromine atom, iodine atom and trifluoromethyl. In this case, each X may be the same as or different from each other, when m which represents the number of substituents represented by X represents an integer of 2 or more.

In the compounds described in the present specification, m which represents the number of substituents represented by X is preferably 1, 2, and 3.

In the compounds described in the present specification, a position of a substituent represented by X is preferably the meta position or para position to the bonding position of a carbon to which $R^1$ is bonded.

In the compounds described in the present specification, examples of a substituent represented by Y preferably include a halogen atom, nitro, $C_1$-$C_4$ alkyl and $C_1$-$C_4$ haloalkyl, and more preferably include a fluorine atom, chlorine atom, bromine atom, iodine atom, nitro, methyl, ethyl and trifluoromethyl. In this case, each Y may be the same as or different from each other, when n represents an integer of 2.

In the compounds described in the present specification, n which represents the number of substituents represented by Y is preferably 0 and 1.

In the compounds described in the present specification, a position of substituent represented by Y is more preferably the ortho position to the bonding position of $R^2$.

In the compounds described in the present specification, examples of a substituent represented by $R^1$ preferably include a $C_1$-$C_4$ haloalkyl, more preferably include a difluoromethyl, chlorodifluoromethyl, bromodifluoromethyl and trifluoromethyl, and extremely preferably include a chlorodifluoromethyl and trifluoromethyl.

In the compounds described in the present specification, examples of a substituent represented by $R^2$ preferably include a methyl, a halogen atom, cyano, nitro, —$NH_2$, —$NHR^4$, —OH, —$OR^3$, benzyloxy, —$OSO_2R^3$, phenylsulfonyloxy, p-toluenesulfonyloxy, —C(O)OH, —C(O)$OR^3$, —C(O)$NH_2$, —C(O)N($R^{1b}$)$R^{1a}$, -L-Q, -L-N($R^{1c}$)$R^{1d}$, D-1 to D-50 or —S(O)$_r$-$L^2$-$Q^2$, and more preferably include a methyl, chlorine atom, bromine atom, iodine atom, cyano, nitro, amino, —NHR$^4$, hydroxy, methoxy, methoxymethyloxy, acetyloxy, benzyloxy, methanesulfonyloxy, trifluoromethanesulfonyloxy, p-toluenesulfonyloxy, —C(O)OH, methoxycarbonyl, ethoxycarbonyl, —C(O)NH$^2$, —C(O)N(R$^{1b}$)R$^{1a}$, -L-Q, -L-N(R$^{1c}$)R$^{1d}$, G or —S(O)$_r$-L$^2$-Q$^2$, In the compounds described in the present specification, examples of a substituent represented by R$^3$ preferably include a C$_1$-C$_4$ alkyl, C$_1$-C$_4$ alkoxy (C$_1$-C$_4$) alkyl and C$_1$-C$_4$ haloalkyl, and more preferably include a methyl, ethyl, methoxymethyl, methoxyethyl, ethoxymethyl and trifluoromethyl.

In the compounds described in the present specification, examples of a substituent represented by R$^4$ preferably include a —CHO, C$_1$-C$_4$ alkylcarbonyl and C$_1$-C$_4$ alkoxycarbonyl, and more preferably include a formyl, acetyl, propionyl, methoxycarbonyl and ethoxycarbonyl.

In the compounds described in the present specification, an example of a substituent represented by R$^5$ preferably includes a hydrogen atom.

In the compounds described in the present specification, examples of a substituent represented by R$^{1a}$ preferably include a C$_1$-C$_4$ alkyl optionally substituted by R$^8$, —N(R$^{11}$)R$^{10}$, —C(O)OR$^9$, —C(O)NH$_2$, —C(O)NHR$^9$, —C(R$^7$)=NOR$^6$, phenyl, phenyl substituted by (Z)$_{p1}$, D-5, D-7, D-10, D-11, D-12, D-14, D-15, D-31, D-32, D-42, D-43, D-45, D-46, D-48, E-1 or E-7.

In the compounds described in the present specification, examples of a substituent represented by R$^{1b}$ preferably include a hydrogen atom, C$_1$-C$_6$ alkyl, C$_1$-C$_4$ alkoxy (C$_1$-C$_4$) alkyl, cyano (C$_1$-C$_4$) alkyl, C$_3$-C$_6$ alkynyl, —C(O)R$^9$ and —C(O)OR$^9$, and more preferably include a hydrogen atom, methyl, ethyl, methoxymethyl, cyanomethyl, propargyl, acetyl, propionyl, butyryl, pivaloyl, methoxycarbonyl and ethoxycarbonyl.

In the compounds described in the present specification, examples of a substituent represented by R$^8$ preferably include a halogen atom, cyano, C$_3$-C$_6$ cycloalkyl, C$_1$-C$_4$ alkoxy, C$_1$-C$_4$ haloalkoxy, —C(O)N(R$^{15}$)R$^{14}$, —C(R$^7$)=NOR$^6$, phenyl, phenyl substituted by (Z)$_{p1}$, D-11 to D-14, D-18, D-19, D-25, D-26, D-31, D-32, D-36, D42, D-45, D-48, D-49, E-1, E-2 or E-5, and more preferably include a fluorine atom, chlorine atom, bromine atom, cyano, cyclopropyl, methoxy, ethoxy, 2,2,2-trifluoroethoxy, —C(O)N(R$^{15}$)R$^{14}$, —CH=NOCH$_3$, phenyl, phenyl substituted by (Z)$_{p1}$, D-14, D-19, D-31, D-32, D-36, D-42 and E-5.

In the compounds described in the present specification, examples of a substituent represented by Z preferably include a halogen atom, cyano, nitro, C$_1$-C$_4$ alkyl, C$_1$-C$_4$ haloalkyl and C$_1$-C$_4$ haloalkoxy, and more preferably include a fluorine atom, chlorine atom, bromine atom, cyano, nitro, methyl, trifluoromethyl and trifluoromethoxy. In this case, each Z may be the same as or different from each other, when p1, p2, p3 or p4 which represents the number of substituents represented by Z represents an integer of 2 or more.

In the compounds described in the present specification, p1 which represents the number of substituents represented by Z preferably includes 1 and 2.

In the compounds described in the present specification, p2 which represents the number of substituents represented by Z preferably includes 0 and 1.

In the compounds described in the present specification, p3 which represents the number of substituents represented by Z preferably includes 0 and 1.

In the compounds described in the present specification, p4 which represents the number of substituents represented by Z preferably includes 0 and 1.

In the compounds described in the present specification, p5 which represents the number of substituents represented by Z preferably includes 0 and 1.

In the compounds described in the present specification, examples of a substituent represented by R$^6$ preferably include a C$_1$-C$_4$ alkyl, and more preferably include a methyl and ethyl.

In the compounds described in the present specification, examples of a substituent represented by R$^7$ preferably include a hydrogen atom and C$_1$-C$_4$ alkyl, and more preferably include a hydrogen atom and methyl.

In the compounds described in the present specification, examples of a substituent represented by R$^9$ preferably include a C$_1$-C$_4$ alkyl, C$_1$-C$_4$ haloalkyl, C$_1$-C$_4$ alkoxy (C$_1$-C$_4$) alkyl, C$_1$-C$_4$ alkylthio (C$_1$-C$_4$) alkyl, C$_3$-C$_8$ cycloalkyl, C$_3$-C$_6$ alkenyl and C$_3$-C$_6$ alkynyl, more preferably include a methyl, ethyl, n-propyl, i-propyl, n-butyl, i-butyl, s-butyl, t-butyl, trifluoromethyl, chloroethyl, 2,2,2-trifluoroethyl, methoxymethyl, ethoxymethyl, methoxyethyl, methylthiomethyl, cyclopropyl, allyl and propargyl.

In the compounds described in the present specification, examples of a substituent represented by R$^{10}$ preferably include a C$_1$-C$_4$ haloalkyl, —C(O)R$^{14}$, —C(O)OR$^{14}$, phenyl, phenyl substituted by (Z)$_{p1}$, D-3, D-4, D18, D-42, D-45, D-46, D-48 or D-49, and more preferably include a 2,2,2-trifluoroethyl, —C(O)R$^{14}$, —C(O)OR$^{14}$, phenyl, phenyl substituted by (Z)$_{p1}$, D-18, D-42 and D-45.

In the compounds described in the present specification, examples of a substituent represented by R$^{11}$ preferably include a hydrogen atom, C$_1$-C$_6$ alkyl and C$_3$-C$_6$ alkynyl, and more preferably include a hydrogen atom, methyl, ethyl and propargyl.

In the compounds described in the present specification, examples of a substituent represented by R$^{12}$ preferably include a C$_1$-C$_4$ alkyl, and more preferably include methyl and ethyl.

In the compounds described in the present specification, examples of a substituent represented by R$^{13}$ preferably include a C$_1$-C$_4$ alkyl, and more preferably include a methyl. In this case, each R$^{13}$ may be the same as or different from each other, when p1, p2, p3 or p4 which represents the number of substituents represented by R$^{13}$ represents an integer of 2 or more. In addition, two R$^{13}$s may together form oxo, when the two R$^{13}$s are substituted on the same carbon atom.

In the compounds described in the present specification, q2 which represents the number of substituents represented by R$^{13}$ preferably includes 1 and 2.

In the compounds described in the present specification, q3 which represents the number of substituents represented by R$^{13}$ preferably includes 0, 1 and 2.

In the compounds described in the present specification, q4 which represents the number of substituents represented by R$^{13}$ preferably includes 0, 1 and 2.

In the compounds described in the present specification, examples of a substituent represented by R$^{14}$ preferably include a C$_1$-C$_4$ alkyl, C$_1$-C$_4$ haloalkyl, C$_3$-C$_6$ cycloalkyl (C$_1$-C$_4$) alkyl, C$_3$-C$_6$ cycloalkyl, C$_3$-C$_6$ alkenyl and C$_3$-C$_6$ alkynyl, and more preferably include a methyl, ethyl, 2-fluoroethyl, 2-chloroethyl, 2-bromoethyl, 2,2,2-trifluoroethyl, cyclopropylmethyl, cyclopropyl, allyl and propargyl.

In the compounds described in the present specification, examples of a substituent represented by R$^{15}$ preferably include a hydrogen atom and C$_1$-C$_4$ alkyl, and more preferably include a hydrogen, methyl and ethyl.

In the compounds described in the present specification, r which represents the number of oxygen on a sulfur atom includes 0, 1 and 2.

In the compounds described in the present specification, t which represents the number of oxygen on a nitrogen atom in a pyridine ring includes 0 and 1.

In the compounds described in the present specification, examples of L preferably include a —$CH_2$—, —CH($CH_3$)—, —CH(CN)—, —CH($R^{2a}$)$CH_2$— (where $R^{2a}$ represents a hydrogen atom, cyano or $C_1$-$C_6$ alkyl), —N($R^{2c}$)— and —CH($R^{2a}$)N($R^{2c}$)— (where $R^{2a}$ represents a hydrogen atom, cyano or $C_1$-$C_6$ alkyl and $R^{2c}$ represents a hydrogen atom, $C_1$-$C_6$ alkyl, $C_1$-$C_6$ alkylcarbonyl, $C_1$-$C_6$ haloalkylcarbonyl or $C_3$-$C_6$ cycloalkyl carbonyl), and particularly preferably include a —$CH_2$—, —CH($CH_3$)— and —CH(CN)—.

In the compounds described in the present specification, examples of $R^{1c}$ include a hydrogen atom, —C(O)$R^{3a}$, —C(O)O$R^{3a}$, —C(O)S$R^{3a}$, —C(O)N($R^{3b}$)$R^{3a}$, —C(S)N($R^{3b}$)$R^{3a}$ or —S(O)$_2$$R^{3a}$, and particularly preferably include a —C(O)$R^{3a}$, —C(O)O$R^{3a}$ and —C(O)N($R^{3b}$)$R^{3a}$.

In the compounds described in the present specification, examples of $R^{1d}$ preferably include a hydrogen atom, $C_1$-$C_6$ alkyl, $C_1$-$C_6$ haloalkyl, $C_1$-$C_4$ alkoxy ($C_1$-$C_4$) alkyl, $C_1$-$C_4$ haloalkoxy ($C_1$-$C_4$) alkyl, $C_1$-$C_4$ alkylthio ($C_1$-$C_4$) alkyl, $C_1$-$C_4$ alkylsulfonyl ($C_1$-$C_4$) alkyl, cyano ($C_1$-$C_6$) alkyl, $C_3$-$C_6$ cycloalkyl, $C_3$-$C_6$ cycloalkyl ($C_1$-$C_4$) alkyl, $C_3$-$C_6$ alkenyl, $C_3$-$C_6$ alkynyl, —C(O)$R^{3c}$, —C(O)O$R^{3c}$, —C(O)S$R^{3c}$, $C_1$-$C_6$ haloalkylthio or $C_1$-$C_6$ alkylsulfonyl, and particularly preferably include a hydrogen atom, $C_1$-$C_6$ alkyl, $C_1$-$C_6$ haloalkyl, $C_1$-$C_4$ alkoxy ($C_1$-$C_4$) alkyl, $C_1$-$C_4$ haloalkoxy ($C_1$-$C_4$) alkyl, $C_3$-$C_6$ cycloalkyl ($C_1$-$C_4$) alkyl and —C(O)$R^{3c}$.

Examples of $R^{3a}$ include a $C_1$-$C_6$ alkyl, $C_1$-$C_6$ haloalkyl, ($C_1$-$C_4$) alkyl optionally substituted by $R^{4a}$, $C_3$-$C_6$ cycloalkyl, $C_3$-$C_6$ halocycloalkyl, E-1, E-2, E-4, $C_2$-$C_6$ alkenyl, $C_2$-$C_6$ haloalkenyl, $C_2$-$C_6$ alkynyl, phenyl, phenyl substituted by (V)$_{p1}$, D-3, D-4, D-12 to D-14, D-42 or D-43, and particularly preferably include a $C_1$-$C_6$ alkyl, $C_1$-$C_6$ haloalkyl, ($C_1$-$C_4$) alkyl optionally substituted by $R^{4a}$, $C_3$-$C_6$ cycloalkyl, $C_3$-$C_6$ halocycloalkyl, phenyl and phenyl substituted by (V)$_{p1}$.

Examples of $R^{3b}$ include a hydrogen atom and $C_1$-$C_6$ alkyl.

Examples of $R^{3c}$ include a hydrogen atom $C_1$-$C_4$ alkyl, $C_1$-$C_4$ haloalkyl, $C_3$-$C_6$ cycloalkyl ($C_1$-$C_4$) alkyl, $C_3$-$C_6$ cycloalkyl, $C_3$-$C_6$ alkenyl or $C_3$-$C_6$ alkynyl, or include the case that $R^{3c}$ forms a 5-7 membered ring with a nitrogen atom, carbon atom, oxygen atom or sulfur atom to be bonded, by forming an ethylene chain or benzene ring bonded at ortho-position together with $R^{3a}$.

Examples of $R^{4a}$ include a halogen atom, cyano, nitro, $C_3$-$C_6$ cycloalkyl, $C_1$-$C_4$ alkoxy, $C_1$-$C_6$ alkoxycarbonyl, S(O)$_r$$R^{5a}$, D-42 or D-43.

Examples of $R^{5a}$ include $C_1$-$C_4$ alkyl.

Examples of V include a halogen atom, cyano, nitro, $C_1$-$C_6$ alkyl, $C_1$-$C_6$ haloalkyl, —OH, $C_1$-$C_6$ alkoxy, $C_1$-$C_6$ haloalkoxy, $C_1$-$C_6$ alkylsulfonyloxy, $C_1$-$C_6$ haloalkylsulfonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —$NH_2$, $C_1$-$C_6$ alkylamino, di($C_1$-$C_6$ alkyl) amino, $C_1$-$C_6$ alkoxycarbonyl, —C(O)$NH_2$, $C_1$-$C_6$ alkylaminocarbonyl, $C_1$-$C_6$ haloalkylaminocarbonyl, di($C_1$-$C_6$ alkyl) aminocarbonyl, —C(S)$NH_2$, —S(O)$_2$$NH_2$, $C_1$-$C_6$ alkylaminosulfonyl or di($C_1$-$C_6$ alkyl) aminosulfonyl, and each V may be the same as or different from each other, when p1 represents an integer of 2 or more, and moreover, when two Vs are adjacent, the two adjacent Vs may form a 5-membered ring or a 6-membered ring with carbon atoms bonding to each of the two Vs by forming —O—$CH_2$O— or —OCH$_2$CH$_2$O—, and hydrogen atoms bonding to each carbon atom forming the ring may be optionally substituted by halogen atoms in this case.

Examples of Z include a halogen atom, cyano, nitro, amino, $C_1$-$C_6$ alkyl, ($C_1$-$C_6$) alkyl optionally substituted by $R^{16}$, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, —C(O)$NH_2$, —C(S)$NH_2$, —S(O)$_2$$NH_2$, —C(O)N($R^{18}$)$R^{17}$, —C(S)N($R^{18}$)$R^{17}$, $C_1$-$C_6$ alkylaminosulfonyl or di ($C_1$-$C_6$ alkyl) aminosulfonyl, and preferably include a halogen atom, $C_1$-$C_6$ alkyl, $C_1$-$C_6$ alkylthio, $C_1$-$C_6$ alkylsulfinyl, $C_1$-$C_6$ haloalkylsulfinyl, $C_1$-$C_6$ alkylsulfonyl and C(O)N($R^{18}$)$R^{17}$.

Examples of $L^2$ preferably include a single bond, methylene, ethylidene, propylidene, 1-methyl-ethyliden, butylidene, 1-methyl-propylidene, 2-methyl-propylidene, pentylidene, 1-methylbutylidene, 2-methylbutylidene, 3-methylbutylidene, hexylidene, ethylene, trimethylene, tetramethylene, pentamethylene and hexamethylene.

Examples of $Q^2$ include a hydrogen atom, $C_1$-$C_6$ haloalkyl, $C_2$-$C_6$ alkynyl, —N($R^{23}$)$R^{22}$, —C(O)N($R^{23}$)$R^{22}$, phenyl, phenyl substituted by (Z)$_{p1}$, D18 to D20 or D-42 to D47, and preferably include a hydrogen atom, $C_1$-$C_6$ haloalkyl, $C_2$-$C_6$ alkynyl, —N($R^{23}$)$R^{22}$, —C(O)N($R^{23}$)$R^{22}$ and D42 to D47.

Specific examples of the expression of ($R^{1b}$ may form a 3-7 membered ring with a nitrogen atom to be bonded, by forming a $C_2$-$C_6$ alkylene chain together with $R^{1a}$, and this alkylene chain may include one oxygen atom, sulfur atom or nitrogen atom in this case) in the present specification include an aziridine, azetidine, pyrrolidine, oxazolidine, thiazolidine, imidazolidine, piperidine, morpholine, thiomorpholine, piperazine, homopiperizine, and heptamethyleneimine, each of which is selected within the range of each specified number of atoms.

Specific examples of the expression of ($R^{1c}$ may form a 5-7 membered ring with a nitrogen atom to be bonded, by forming a $C_4$-$C_6$ alkylene chain together with $R^{1d}$, and this alkylene chain may include one oxygen atom, sulfur atom or nitrogen atom in this case, and may be optionally substituted by an oxo group or thioxo group) in the present specification include an aziridine, azetidine, azetidine-2-one, pyrrolidine, pyrrolidine-2-one, oxazolidine, oxazolidine-2-one, oxazolidine-2-thione, thiazolidine, thiazolidine-2-one, thiazolidine-2-thione, imidazolidine, imidazolidine-2-one, imidazolidine-2-thione, piperidine, piperidine-2-one, piperidine-2-thione, 2H-3,4,5,6-tetrahydro-1,3-oxazin-2-one, 2H-3,4,5,6-tetrahydro-1,3-oxazin-2-thione, morpholine, 2H-3,4,5,6-tetrahydro-1,3-thiazine-2-one, 2H-3,4,5,6-tetrahydro-1,3-thiazine-2-thione, thiomorpholine, perhydropyrimidine-2-one, piperazine, homopiperizine, homopiperizine-2-one and heptamethyleneimine, each of which is selected within the range of each specified number of atoms.

Specific examples of the expression of ($R^{2a}$ may form a 3-6 membered ring with a nitrogen atom to be bonded, by forming a $C_2$-$C_5$ alkylene chain together with $R^{2b}$, and this alkylene chain may include one oxygen atom, sulfur atom or nitrogen atom in this case) in the present specification include a cyclopropane ring, cyclobutane ring, cyclopentane ring, tetrahydrofuran ring, tetrahydrothiophene ring, pyrrolidine ring, cyclohexane ring, tetrahydropyran ring, tetrahydrothiopyran ring, piperidine ring, cycloheptane ring, oxepane ring, thiepane ring and azepane ring. Each of the rings is selected within the range of each specified number of atoms.

Examples of solvents capable to be used for the reactions during the production of (2) from (3), the production of (3) from (4) and (5) and the production of (2) from (4) and (5) in one step according to the present invention include aromatic hydrocarbons which may be substituted by halogen atoms such as benzene, toluene, xylene, chlorobenzene, o-dichlorobenzene or mesitylene; or aliphatic hydrocarbons which may be substituted by halogen atoms such as n-pentane, n-hexane, n-heptane, n-octane, cyclopentane, cyclohexane, methylcyclohexane, methylene chloride or 1,2-dichloroethane; ethers such as diethyl ether, diisopropyl ether, cyclopentyl methyl ether, t-butyl methyl ether; nitriles such as acetonitrile and propionitrile; esters such as ethyl acetate and butyl acetate; amines such as triethylamine, tributylamine and pyridine; nitromethane; nitroethane; water and a supercritical fluid, and preferably include toluene, n-hexane, n-heptane, cyclohexane, methylene chloride, 1,2-dichloroethane, chlorobenzene, diisopropyl ether, cyclopentyl methyl ether, t-butyl methyl ether, acetonitrile, propionitrile, ethyl acetate, butyl acetate, triethylamine, tributylamine, pyridine, nitromethane, water or the supercritical carbon dioxide, and particularly preferably include toluene for the production of (2) from (3); water, chlorobenzene, toluene, n-heptane, tributylamine or ethyl acetate for the production of (3) from (4) and (5); and toluene for the production of (2) from (4) and (5) in one step. These solvents may be used singly or in combination.

An amount used of such solvents is not particularly limited. However, the amount is usually 0.01 to 100 parts by weight, preferably 0.05 to 50 parts by weight, and particularly preferably 0.1 to 15 parts by weight per part by weight of the aromatic ketone compound or the substituted acetophenone compound or the 1,3-bis(substituted phenyl)-3-substituted-3-hydroxypropan-1-one compound.

Examples of bases capable to be used for the reaction according to the present invention include sodium hydroxide, potassium hydroxide, barium hydroxide, calcium hydroxide, potassium carbonate, sodium carbonate, barium carbonate, calcium carbonate, potassium bicarbonate, sodium bicarbonate, sodium acetate, potassium acetate, sodium methoxide, potassium-t-butoxide, ammonia, methylamine, ethylamine, n-propylamine, i-propylamine, n-butylamine, i-butylamine, t-butylamine, n-pentylamine, i-pentylamine, benzylamine, aniline, dimethylamine, diethylamine, di-n-propylamine, di-i-propylamine, di-n-butylamine, di-i-butylamine, di-n-pentylamine, di-i-pentylamine, pyrrolidine, piperidine, piperazine, morpholine, dibenzylamine, trimethylamine, triethylamine, tri-n-propylamine, tri-n-butylamine, tripentylamine, tribenzylamine, diisopropylethylamine, N-methylmorpholine, pyridine, 2-methyl-5-ethylpyridine, 4-dimethylaminopyridine, 1,8-diazabicyclo (5,4,0)-7-undecene, triethylenediamine, N,N,N',N'-tetramethylethylenediamine or 1,1,3,3-tetramethylguanidine, and preferably include pyridine, 2-methyl-5-ethylpyridine, tributylamine and 4-dimethylaminopyridine, for the production of (2) from (3); diethylamine, di-i-propylamine, di-n-propylamine, di-n-butylamine, pyrrolidine, triethylamine, tri-n-butylamine for the production of (3) from (4) and (5) performed in an organic solvent; potassium carbonate and sodium carbonate for the production of (3) from (4) and (5) performed in water; potassium carbonate, sodium carbonate tri-n-butylamine, 4-dimethylaminopyridine, 1,8-diazabicyclo (5,4,0)-7-undecene and 1,1,3,3-tetramethylguanidine for the production of (2) from (4) and (5) in one step. These bases may be used singly or in combination.

An amount used of such bases is not particularly limited. However, the amount is usually 0.01 to 100 times by mole, preferably 0.05 to 50 times by mole, particularly preferably 0.05 to 10 times by mole per mol of the 1,3-bis(substituted phenyl)-3-substituted-3-hydroxypropan-1-one compound for the production of (2) from (3), and usually 0.01 to 50 times by mole, preferably 0.05 to 25 times by mole, particularly preferably 0.05 to 5 times by mole per mol of the aromatic ketone compound or the substituted acetophenone compound for the production of (3) from (4) and (5), and the production of (2) from (4) and (5) in one step.

Examples of surfactants or the like capable to be used for the reaction according to the present invention as additives include as follows:

(A) Nonionic Surfactant:

(A-1) Polyethylene glycol type surfactants: Examples of polyethylene glycol type surfactants include polyoxyethylenealkyl ($C_{12-18}$) ether, an ethyleneoxide adduct of alkylnaphthol, polyoxyethylene (mono or di) alkyl ($C_{8-12}$) phenyl ether, formaldehyde condensation products of polyoxyethylene (mono or di) alkyl ($C_{8-12}$) phenyl ether, polyoxyethylene (mono, di, or tri) phenyl phenyl ether, polyoxyethylene (mono, di or tri) benzyl phenyl ether, polyoxypropylene (mono, di, or tri) benzyl phenyl ether, polyoxyethylene (mono, di, or tri) styryl phenyl ether, polyoxypropylene (mono, di or tri) styryl phenyl ether, a polymer of polyoxyethylene (mono, di or tri) styryl phenyl ether, a polyoxyethylene polyoxypropylene block polymer, an alkyl ($C_{12-18}$) polyoxyethylene polyoxypropylene block polymer ether, an alkyl ($C_{8-12}$) phenyl polyoxyethylene polyoxypropylene block polymer ether, polyoxyethylene bisphenyl ether, polyoxyethylene resin acid ester, polyoxyethylene fatty acid ($C_{12-18}$) monoester, polyoxyethylene fatty acid ($C_{12-18}$) diester, polyoxyethylene sorbitan fatty acid ($C_{12-18}$) ester, ethyleneoxide adduct of glycerol fatty acid ester, ethyleneoxide adduct of castor oil, ethyleneoxide adduct of hardened caster oil, ethyleneoxide adduct of alkyl ($C_{12-18}$) amine and ethyleneoxide adduct of fatty acid ($C_{12-18}$) amide.

(A-2) Polyvalent alcohol type surfactants: Examples of polyvalent alcohol type surfactants include glycerol fatty acid ester, polyglycerin fatty acid ester, pentaerythritol fatty acid ester, sorbitol fatty acid ($C_{12-18}$) ester, sorbitan fatty acid ($C_{12-18}$) ester, sucrose fatty acid ester, polyvalent alcohol alkyl ether and fatty acid alkanol amide.

(A-3) Acetylene type surfactants: Examples of acetylene type surfactants include acetylene glycol, acetylene alcohol, ethyleneoxide adduct of acetylene glycol and ethyleneoxide adduct of acetylene alcohol.

(A-4) Other surfactants: Examples of other surfactants include alkylglucoside.

(B) Anionic Surfactants:

(B-1) Carboxylic acid type surfactants: Examples of carboxylic acid type surfactants include polyacrylic acid, polymethacrylic acid, polymaleic acid, a copolymer of maleic acid and olefin (for example, isobutylene and diisobutylene), a copolymer of acrylic acid and itaconic acid, a copolymer of methacrylic acid and itaconic acid, a copolymer of maleic acid and styrene, a copolymer of acrylic acid and methacrylic acid, a copolymer of acrylic acid and methyl acrylate, a copolymer of acrylic acid and vinyl acetate, a copolymer of acrylic acid and maleic acid, N-methyl-fatty acid ($C_{12-18}$) sarcosinate, carboxylic acids such as resin acid and fatty acid ($C_{6-20}$) and the like, and salts of these carboxylic acids.

(B-2) Sulfate ester type surfactants: Examples sulfate ester type surfactants include alkyl ($C_{12-18}$) sulfate ester, polyoxyethylene alkyl ($C_{12-18}$) ether sulfate ester, polyoxyethylene (mono or di) alkyl ($C_{8-12}$) phenyl ether sulfate ester, sulfate ester of a polyoxyethylene (mono or di) alkyl ($C_{12-18}$) phenyl ether polymer, polyoxyethylene (mono, di, or tri) phenyl phenyl ether sulfate ester, polyoxyethylene (mono, di, or tri) benzyl phenyl ether sulfate ester, polyoxyethylene (mono, di, or tri) styryl phenyl ether sulfate ester, sulfate ester of a polyoxyethylene (mono, di, or tri) styryl phenyl ether polymer, sulfate ester of a polyoxyethylene polyoxypropylene block polymer, sulfated oil, sulfated fatty acid ester, sulfated fatty acid and sulfate ester of sulfated olefin and the like, and salts of these sulfate esters.

(B-3) Sulfonic acid type surfactants: Examples of sulfonic acid type surfactants include paraffin ($C_{12-22}$) sulfonic acid, alkyl ($C_{8-12}$) benzene sulfonic acid, formaldehyde condensation products of alkyl ($C_{8-12}$) benzene sulfonic acid, formaldehyde condensation products of cresol sulfonic acid, α-olefin ($C_{14-16}$) sulfonic acid, dialkyl ($C_{8-12}$) sulfosuccinic acid, lignin sulfonic acid, polyoxyethylene (mono or di) alkyl ($C_{8-12}$) phenyl ether sulfonic acid, polyoxyethylenealkyl ($C_{12-18}$) ether sulfosuccinate half ester, naphthalene sulfonic acid, (mono, or di) alkyl ($C_{1-6}$) naphthalene sulfonic acid, formaldehyde condensation products of naphthalene sulfonic acid, formaldehyde condensation products of (mono, or di) alkyl ($C_{1-6}$) naphthalene sulfonic acid, formaldehyde condensation products of creosote oil sulfonic acid, alkyl ($C_{8-12}$) diphenyl ether disulfonic acid, Igepon T (trade name), polystyrene sulfonic acid and sulfonic acids of a styrene sulfonic acid-methacrylic acid copolymer and the like, and salts of these sulfonic acids (B-4) Phosphate ester type surfactants: Examples of phosphate ester type surfactants include alkyl ($C_{12-18}$) phosphate ester, polyoxyethylene alkyl ($C_{12-18}$) ether phosphate ester, polyoxyethylene (mono or di) alkyl ($C_{8-12}$) phenyl ether phosphate ester, phosphate ester of a polyoxyethylene (mono, di, or tri) alkyl ($C_{8-12}$) phenyl ether polymer, polyoxyethylene (mono, di, or tri) phenyl phenyl ether phosphate ester, polyoxyethylene (mono, di, or tri) benzyl phenyl ether phosphate ester, polyoxyethylene (mono, di, or tri) styryl phenyl ether phosphate ester, phosphate ester of a polyoxyethylene (mono, di, or tri) styryl phenyl ether polymer, phosphate ester of a polyoxyethylene polyoxypropylene block polymer, phosphatidylcholine, phosphatidyl ethanolimine and phosphate ester of condensed phosphoric acid (for example, tripolyphosphoric acid) and the like, and salts of these phosphate esters.

Salts of above-mentioned (B-1) to (B-4) include alkaline metals (such as lithium, sodium and potassium), alkaline earth metals (such as calcium and magnesium), ammonium and various types of amines (such as alkyl amines, cycloalkyl amines and alkanol amines).

(C) Cationic Surfactants:

Examples of cationic surfactants include alkyl amine salts and alkyl quaternary ammonium salts.

(D) Amphoteric Surfactants:

Examples of amphoteric surfactants include betaine type surfactants and amino acid type surfactants.

(E) Other Surfactants:

Examples of other surfactants include silicone type surfactant and fluorine type surfactant. Preferable examples include Soprofol (anionic/nonionic surfactant, trade name of Rhodia Nicca, Ltd.), Solpol 3353 (nonionic surfactant, trade name of Toho Chemical Industry Co., Ltd.), Epan (polyoxyethylene polyoxypropylene glycol, trade name of Daiichi Kogyo Seiyaku Co., Ltd.), tetrabutylammonium bromide, cetylpyridinium chloride, dodecyltrimethylammonium chloride, dodecylamine hydrochloride, sodium dodecyl sulfate, sodium dodecanesulfonate, dodecylbenzenesulfonic acid or the salt thereof, p-toluenesulfonic acid or the salt thereof, polyethylene glycol, hexanoic acid or the salt thereof, octanoic acid or the salt thereof, decanoic acid or the salt thereof, lauric acid or the salt thereof, myristic acid or the salt thereof, palmitic acid or the salt thereof, stearic acid or the salt thereof, oleic acid or the salt thereof, proline or the salt thereof and phenylalanine or the salt thereof.

Examples of the salts include alkali metals (lithium, sodium and potassium), alkaline earth metals (calcium and magnesium), ammonium and pyridinium.

Such surfactants are usually 0.0001 to 1 times by mole, preferably 0.001 to 1 times by mole, particularly preferably 0.01 to 0.5 times by mole per mol of the aromatic ketone compound (4) or the substituted acetophenone compound (5).

Examples of water soluble organic solvents capable to be used for the reaction according to the present invention as additives include dimethylsulfoxide, sulfolane, N,N-dimethylformamide, N,N-dimethylacetamide, N-methyl-2-pyrrolidone, N,N'-dimethylethylene urea, hexamethylphosphoric triamide, acetonitrile, propionitrile, methanol, ethanol or nitromethane, and preferably dimethyl sulfoxide, sulfolane, N,N-dimethylformamide, hexamethylphosphoric triamide, acetonitrile, methanol or nitromethane, and particularly preferably N,N-dimethylacetamide, acetonitrile or methanol. These may be used singly or in combination.

An amount used of such water organic soluble solvents is usually 0.01 to 10 parts by weight, preferably 0.05 to 5 parts by weight, and particularly preferably 0.05 to 3 parts by weight per part by weight of the aromatic ketone compound or the substituted acetophenone compound.

Examples of compounds capable to be used for the reaction according to the present invention as dehydration agents include thionyl chloride, sulfuric chloride, methanesulfonyl chloride, p-toluenesulfonyl chloride, benzoyl chloride, acetyl chloride, acetic anhydride, propionic anhydride or benzoic anhydride, and preferably thionyl chloride, sulfuric chloride, methanesulfonyl chloride, benzoyl chloride, acetyl chloride, acetic anhydride or benzoic anhydride.

An amount used of such dehydration agents is usually 0.1 to 100 times by mole, preferably 0.5 to 50 times by mole, particularly preferably 1 to 15 times by mole per mol of the 1,3-bis(substituted phenyl)-3-substituted-3-hydroxypropan-1-one compound.

For performing the production of (2) from (3) according to the present invention, for example, 1,3-bis(substituted phenyl)-3-substituted-3-hydroxypropan-1-one compound represented by Formula (3) or the salt thereof, a solvent as represented by toluene, a base as represented by triethylamine, tri-n-butylamine, pyridine and 4-dimethylaminopyridine, a dehydration agent as represented by thionyl chloride and acetic anhydride are fed into a reactor, and the mixture may be stirred for usually about 10 minutes to 150 hours, and preferably about 1 to 96 hour(s) usually at 0 to 150° C. and preferably at 20 to 120° C.

For performing the production of (3) from (4) and (5) or the production of (2) from (4) and (5) in one step according to the present invention, for example, a predetermined amount of the aromatic ketone compound represented by Formula (4) and the substituted acetophenone compound represented by Formula (5), a solvent as represented by toluene, a base as represented by triethylamine and tri-n-butylamine are fed into a reactor, and the mixture may be stirred for usually about 10 minutes to 150 hours, and preferably about 1 to 96 hour(s) usually at 0 to 150° C. and preferably at 20 to 100° C.

For example, a predetermined amount of the aromatic ketone compound represented by Formula (4) and the substituted acetophenone compound represented by Formula (5), water, a base as represented by potassium carbonate and a water soluble organic solvent are fed into a reactor, and the mixture may be stirred for usually about 10 minutes to 150 hours, and preferably about 1 to 96 hour(s) usually at 0 to 100° C. and preferably at 20 to 100° C.

For example, a predetermined amount of the aromatic ketone compound represented by Formula (4) and the substituted acetophenone compound represented by Formula (5), water, a base as represented by potassium carbonate, a surfactant and the like are fed into a reactor, and the mixture may be stirred for usually about 10 minutes to 150 hours, and preferably about 1 to 96 hour(s) usually at 0 to 100° C. and preferably at 20 to 100° C.

For example, a predetermined amount of the aromatic ketone compound represented by Formula (4) and the substituted acetophenone compound represented by Formula (5), a solvent as represented by toluene and a base as represented by potassium carbonate are fed into a reactor, and the mixture may be stirred for usually about 10 minutes to 150 hours, and preferably about 1 to 120 hour(s) usually at 0 to 150° C. and preferably at 20 to 120° C.

For example, a predetermined amount of the aromatic ketone compound represented by Formula (4) and the substituted acetophenone compound represented by Formula (5), a solvent as represented by toluene, a base as represented by tri-n-butylamine and 4-dimethylaminopyridine, a dehydration agent as represented by benzoic anhydride are fed into a reactor, and the mixture may be stirred for usually about 10 minutes to 150 hours, and preferably about 1 to 120 hour(s) usually at 0 to 150° C. and preferably at 20 to 120° C.

Among them, preferable embodiments include, for example, the case that the solvent is an organic solvent and the reaction is performed without additives; the case that the solvent is water and the reaction is performed with an water soluble organic solvent as the additive; and the case that the solvent is water and the reaction is performed with a surfactant as the additive.

Here, for producing (2) through (3) from (4) and (5) in one pot, it is preferable that an organic solvent is used as the solvent, and the reaction temperature is set to a temperature of over 80° C. In addition, (2) can also be produced in one step by adding a dehydration agent as represented by benzoic anhydride to the reaction solution without isolating (3) produced from (4) and (5).

The compound represented by Formula (4) can be produced, for example, by the following method.

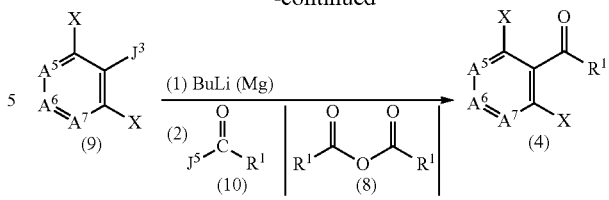

More specifically, a known compound represented by General Formula (6) (where X represents the same meaning as described above, and $A^5$, $A^6$ and $A^7$ independently represent C—X) and a known compound represented by General Formula (7) (where $R^1$ represents the same meaning as described above, and $J^4$ represents a leaving group such as a halogen atom, trifluoromethanesulfonyloxy group and 2-pyridyloxy group) or a known compound represented by General Formula (8) (where $R^1$ represents the same meaning as described above) are reacted by the common aromatic ring acylation reactions described in documents, for example, in accordance with the methods described in "Chemistry Letters (Chem. Lett.)" 783 (1990) and "The Journal of Organic Chemistry (J. Org. Chem.)" vol. 56, 1963 (1991). As a result, a compound represented by General Formula (4) (where X, $R^1$, $A^5$, $A^6$ and $A^7$ represent the same meaning as described above) can be obtained.

The compound represented by General Formula (4) can also be obtained by: the following methods. After a known compound represented by General Formula (9) (where X represents the same meaning as described above; $A^5$, $A^6$ and $A^7$ independently represent C—X or N; and $J^3$ represents a bromine atom or an iodine atom) is treated with a common method described in documents, for example, lithiated, the reactant is made to react with a known compound represented by General Formula (10) (where $R^1$ represents the same meaning as described above; $J^5$ represents a halogen atom, hydroxy group, metal salts (for example, —OLi and —ONa), $C_1$-$C_4$ alkoxy (for example, methoxy group and ethoxy group), di($C_1$-$C_4$ alkyl) amino group (for example diethylamino group), $C_1$-$C_4$ alkoxy ($C_1$-$C_4$ alkyl) amino group (for example, O,N-dimethylhydroxyamino group) or cyclicamino group (for example, piperidin-1-yl group, morpholin-4-yl group and 4-methylpiperazin-1-yl)) or a known compound represented by General Formula (8) in accordance with the methods described in "Journal of the American Chemical Society (J. Am. Chem. Soc)" vol. 77, 3657 (1955), Tetrahedron Letters (Tetrahedron. Lett.) Vol. 21, 2129 (1980) and Vol. 32, 2003 (1991) and U.S. Pat. No. 5,514,816; or after forming a Grignard reagent, the reagent is made to react with the compound represented by General Formula (10) or the compound represented by General Formula (8) in accordance with the methods described in Heterocycles (Heterocycles) Vol. 25, 211 (1987), Synthetic Communications (Synth. Commun.) Vol. 15, 1291 (1985) and German Patent Publication (DE 19,727,042) and the like.

In addition, in General Formula (4), General Formula (3-1), where $R^1$ is trifluoromethyl group, can be synthesized as follows.

Reaction Formula 1

Reaction Formula 2

More specifically, the compound represented by General Formula (4-1) (where X, $A^5$, $A^6$ and $A^7$ represents the same meaning as described above) can also be obtained by reacting a known compound represented by General Formula (11) (where X, $A^5$, $A^6$ and $A^7$ represents the same meaning as described above, and $J^6$ represents a halogen atom or $C_1$-$C_4$ alkoxy group (for example methoxy group)) with a known compound represented by General Formula (12) (where $J^7$ represents tri($C_1$-$C_4$ alkylsilyl group (for example trimethylsilyl group)) by the known methods described in documents, for example, in accordance with the methods described in The Journal of Organic Chemistry (J. Org. Chem.) vol. 64, 2873 (1999), The Journal of Organic Chemistry (J. Org. Chem.) vol. 56, 984 (1991).

In each reaction, each production intermediate which acts as raw material compound can be obtained by performing common treatment after the completion of the reaction.

In addition, each production intermediate produced by these methods can also be used in an untreated state in next steps without isolation and purification.

Examples of the solvents capable to be used in the reaction when (1) is produced from (2) according to the present invention include aromatic hydrocarbons which may be substituted by halogen atoms such as benzene, toluene, xylene, chlorobenzene, o-dichlorobenzene or mesitylene; or aliphatic hydrocarbons which may be substituted by halogen atoms such as n-pentane, n-hexane, n-heptane, n-octane, cyclopentane, cyclohexane, methylene chloride, 1,2-dichloroethane or methylcyclohexane, preferably toluene, n-hexane, n-heptane, cyclohexane, methylene chloride or chlorobenzene, and particularly preferably toluene, n-heptane or methylene chloride. These may be used singly or in combination.

An amount used of such solvents is not particularly limited. However, the amount is usually 0.1 to 100 parts by weight, preferably 1 to 50 parts by weight, and particularly preferably 2 to 15 parts by weight per part by weight of the 1,3-bis(substituted phenyl)-3-substituted-2-propen-1-one compound.

Hydroxylamine may be used in the form of acid-salts such as hydrochloride, sulfate or acetate, or may also be used as an aqueous solution of adequate concentration.

An amount used of such hydroxylamine is usually 0.5 to 100 times by mole, preferably 1 to 10 times by mole, particularly preferably 1 to 2 times by mole per mol of the 1,3-bis(substituted phenyl)-3-substituted-2-propen-1-one compound.

Examples of aprotic polar solvents capable to be used in the reaction according to the present invention as additives include dimethylsulfoxide, sulfolane, ethylene carbonate, propylene carbonate, N,N-dimethylformamide, N,N-dimethylacetamide, N-methyl-2-pyrrolidone, N,N'-dimethylethylene urea, N,N'-dimethylpropylene urea, hexamethylphosphoric triamide, nitromethane, pyridine, 2-methyl-5-ethylpyridine, triethylamine, diisopropylethylamine, tributylamine, 1,8-diazabicyclo (5,4,0)-7-undecene, 1,5-diazabicyclo (4,3,0)-5-nonene, N,N,N',N'-tetramethylethylenediamine or nitrobenzene. These may be used singly or in combination.

An amount used of such aprotic polar solvents is usually 0.1 to 100 parts by weight, preferably 0.5 to 50 parts by weight, and particularly preferably 1 to 15 parts by weight per part by weight of 1,3-bis(substituted phenyl)-3-substituted-2-propen-1-one compound.

Examples of phase-transfer catalysts capable to be used in the reaction according to the present invention as additives include tetrabutylammonium bromide, tetrabutylammonium chloride, tetramethylammonium chloride, tetrapropylammonium hydroxide, tetrabutylammonium hydrogen sulfate, benzyltrimethylammonium chloride, trioctylmethylammonium chloride (ALIQUATR 336), cetylpyridinium chloride, 18-crown-6, dodecyltrimethylammonium chloride, benzyltriphenylphosphonium chloride or ethyltriphenylphosphonium acetate.

Such phase-transfer catalysts are usually 0.0001 to 10 times by mole, and preferably 0.0005 to 1 times by mole per mol of the 1,3-bis(substituted phenyl)-3-substituted-2-propen-1-one compound.

Examples of $C_1$-$C_6$ alcohol capable to be used in the reaction according to the present invention as additives include methanol, ethanol, propanol, isopropanol, butanol or pentanol, and preferably methanol or ethanol, An amount used of such $C_1$-$C_6$ alcohols is usually 0.1 to 100 parts by weight, preferably 0.5 to 50 parts by weight, and particularly preferably 1 to 15 parts by weight per part by weight of the 1,3-bis(substituted phenyl)-3-substituted-2-propen-1-one compound.

Examples of bases capable to be used in the reaction according to the present invention include sodium hydroxide, potassium hydroxide, barium hydroxide, potassium carbonate, potassium bicarbonate, sodium carbonate, sodium bicarbonate, sodium acetate, sodium methoxide, potassium-t-butoxide, pyridine, 2-methyl-5-ethylpyridine, piperidine, triethylamine, di-isopropylethylamine, tributylamine, 4-dimethylaminopyridine, 1,8-diazabicyclo (5,4,0)-7-undecene, 1,5-diazabicyclo (4,3,0)-5-nonene, triethylenediamine, N,N,N',N'-tetramethylethylenediamine, pyrrolidine or 1,1,3,3-tetramethylguanidine.

For performing the reaction according to the present invention, for example, predetermined amounts of a 1,3-bis (substituted phenyl)-3-substituted-2-propen-1-one compound represented by Formula (2) and additives of an aprotic polar solvent, a phase-transfer catalyst and $C_1$-$C_6$ alcohol, and a solvent as represented by toluene are fed into a reactor, and separately, a solution of a mixture of a base, water and hydroxylamine are added in dropwise with stirring to react for about 10 minutes to 120 hours, preferably about 1 to 48 hour(s) usually at −70 to 100° C., preferably −40 to 50° C.

Specific examples of aromatic ketone compounds represented by Formula (4) capable to be used as starting materials according to the present invention are shown in Compound List-1 below. However, the compounds according to the present invention are not limited to these compounds.

Compound List-1

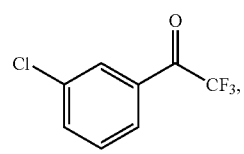

[4]-1

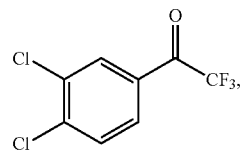

[4]-2

[4]-3 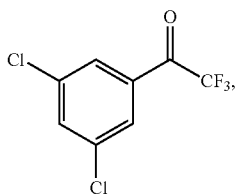

[4]-4 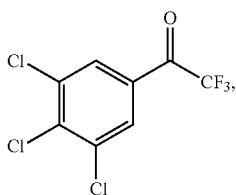

[4]-5 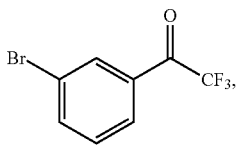

[4]-6 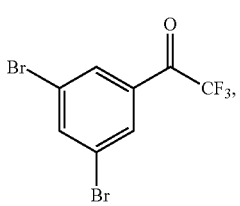

[4]-7 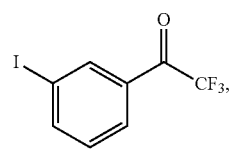

[4]-8 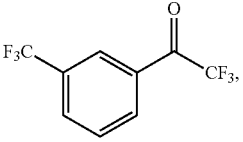

[4]-9 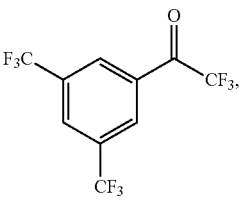

[4]-10 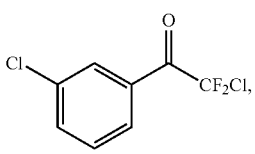

[4]-11 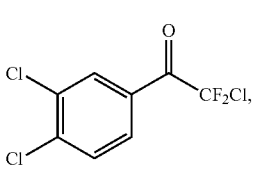

[4]-12 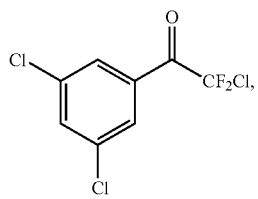

[4]-13 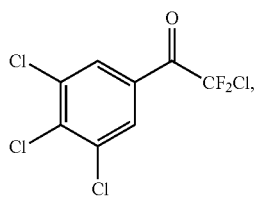

[4]-14 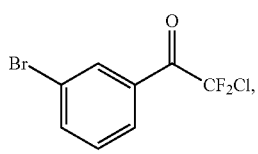

[4]-15 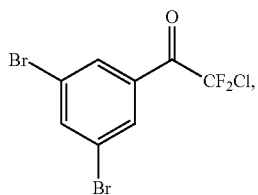

[4]-16 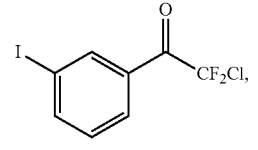

[4]-17 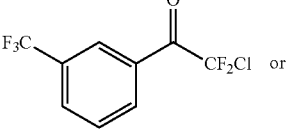 or

[4]-18 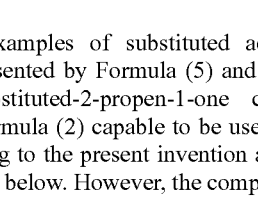

Specific examples of substituted acetophenone compounds represented by Formula (5) and 1,3-bis(substituted phenyl)-3-substituted-2-propen-1-one compounds represented by Formula (2) capable to be used as starting materials according to the present invention are shown in Compounds List-2 below. However, the compounds according to the present invention are not limited to these compounds.

Compound List-2

-continued
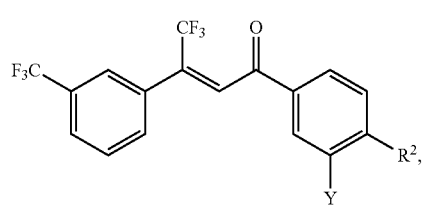
[2]-15
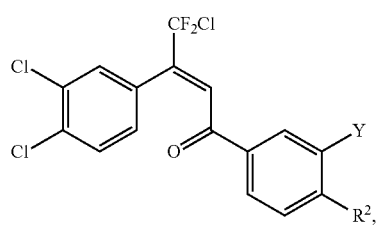
[2]-22
[2]-16
[2]-23
[2]-17
[2]-24
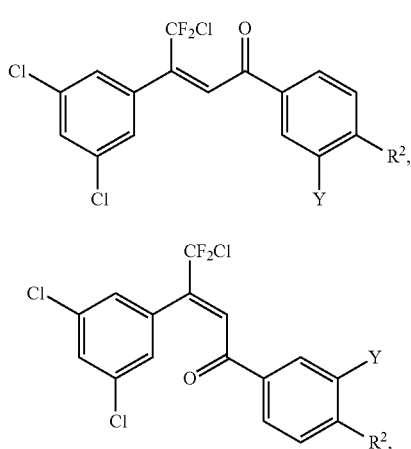
[2]-18
[2]-25
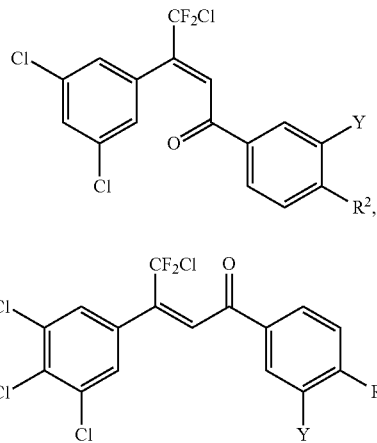
[2]-19
[2]-26
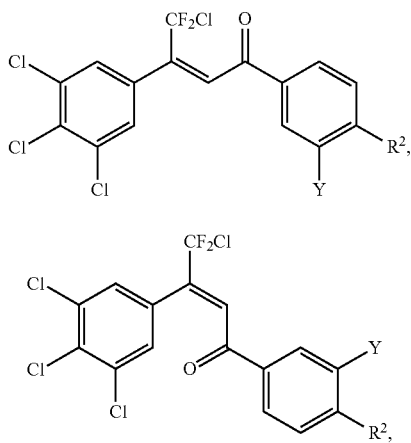
[2]-20
[2]-27
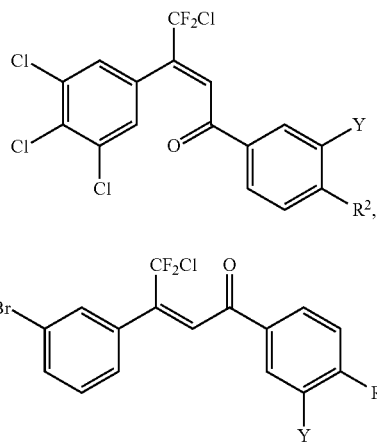
[2]-21
[2]-28
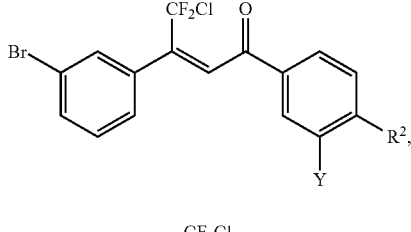
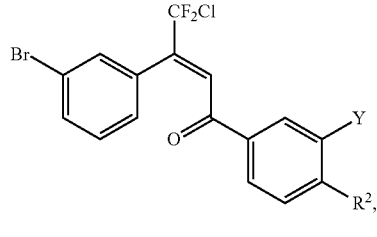

-continued

[2]-29
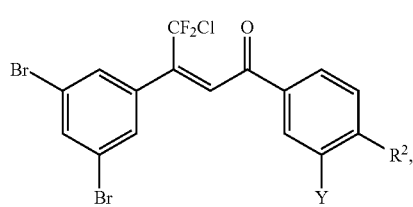

[2]-30
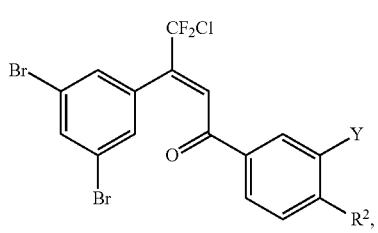

[2]-31
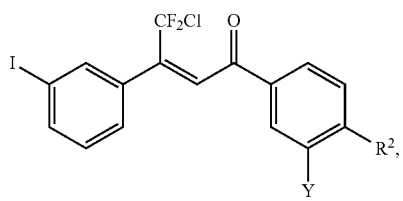

[2]-32
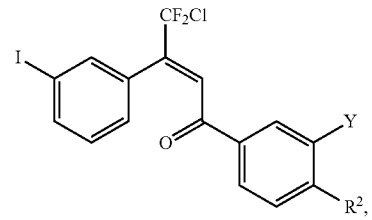

[2]-33
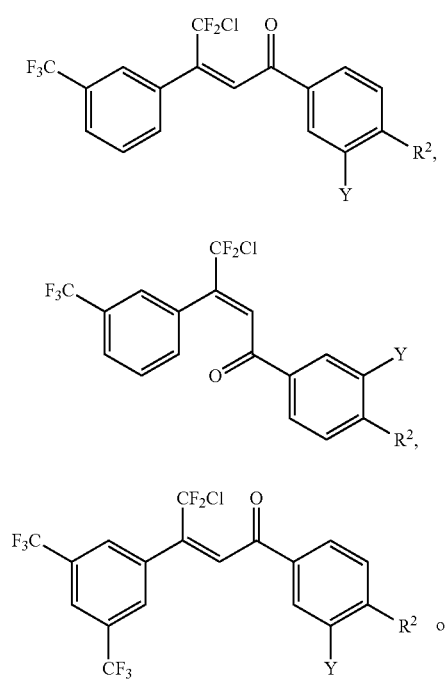

[2]-34

[2]-35
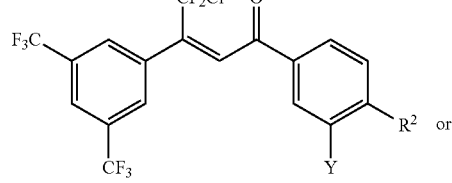

-continued

[2]-36
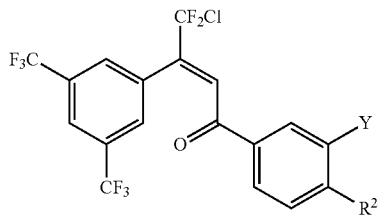

[5]-1
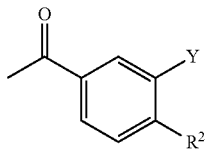

Here, in Compound List-2, the expression Et represents ethyl group, and in the same manner, n-Pr and Pr-n, i-Pr and Pr-i, c-Pr and Pr-c, and Ph represent a normalpropyl group, isopropyl group, cyclopropyl group and phenyl group, respectively.

Specific examples of the substituent Y and $R^2$ in Compound List-2 are shown in Table 1. In Table 1, aromatic heterocyclic groups represented by D-1a to D-50a represent the following structures.

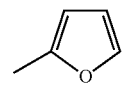 D-1a

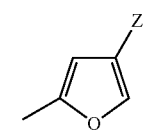 D-1b

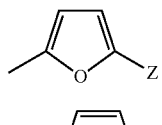 D-1c

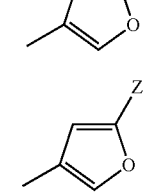 D-2a

D-2b

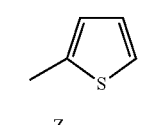 D-3a

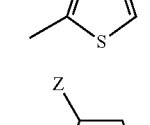 D-3b

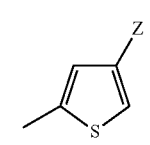 D-3c

-continued
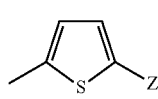 D-3d
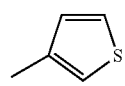 D-4a
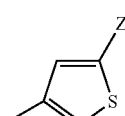 D-4b
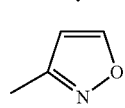 D-5a
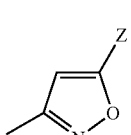 D-5b
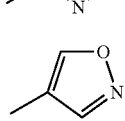 D-6a
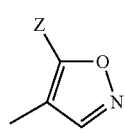 D-6b
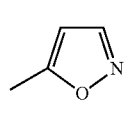 D-7a
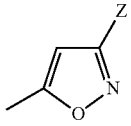 D-7b
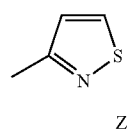 D-8a
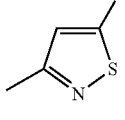 D-8b
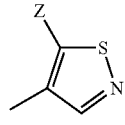 D-9b
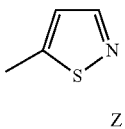 D-10a
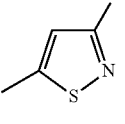 D-10b
-continued
 D-11a
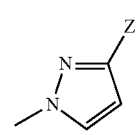 D-11b
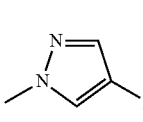 D-11c
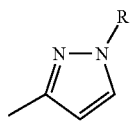 D-12a
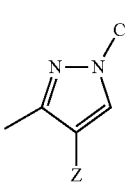 D-12b
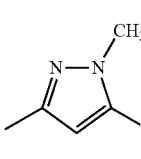 D-12c
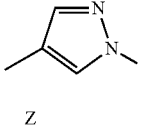 D-13a
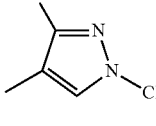 D-13b
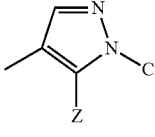 D-13c
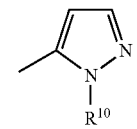 D-14a
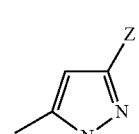 D-14b
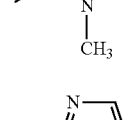 D-15a
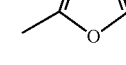

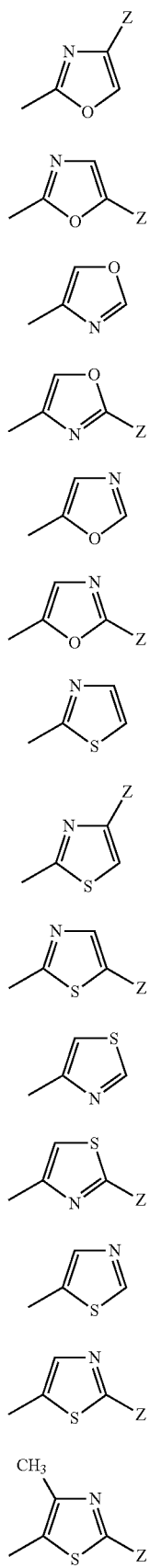
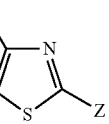
D-15b
D-15c
D-16a
D-16b
D-17a
D-17b
D-18a
D-18b
D-18c
D-19a
D-19b
D-20a
D-20b
D-20c
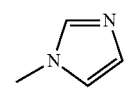 D-21a
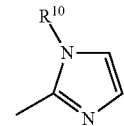 D-22a
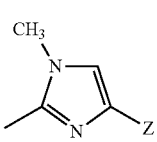 D-22b
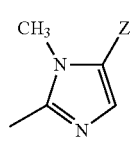 D-22c
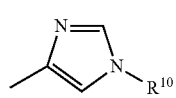 D-23a
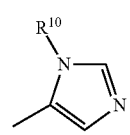 D-24a
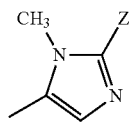 D-24b
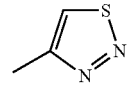 D-25a
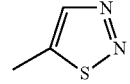 D-26a
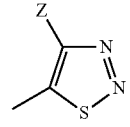 D-26b
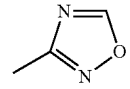 D-27a
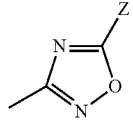 D-27b
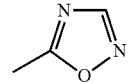 D-28a

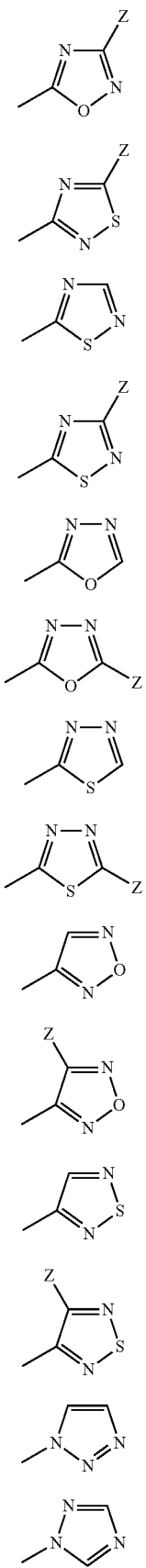
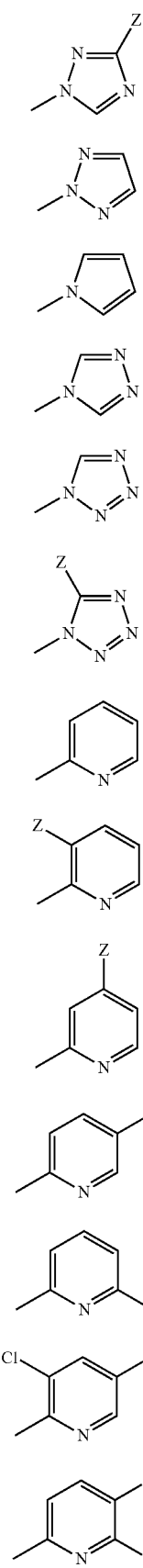
D-28b
D-29a
D-30a
D-30b
D-31a
D-31b
D-32a
D-32b
D-33a
D-33b
D-34a
D-34b
D-35a
D-36a
D-36b
D-37a
D-38a
D-39a
D-40a
D-40b
D-42a
D-42b
D-42c
D-42d
D-42e
D-42f
D-42g

| | | | |
|---|---|---|---|
| D-43a | 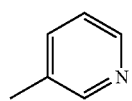 | D-45b | 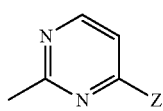 |
| D-43b | 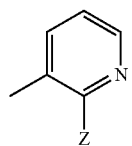 | D-45c | 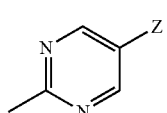 |
| D-43c | 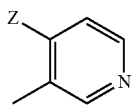 | D-46a | 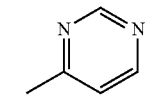 |
| D-43d | 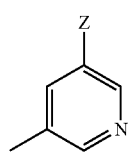 | D-46b | 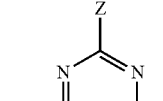 |
| D-43e | 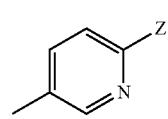 | D-46c | 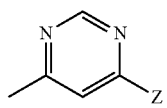 |
| D-43f | 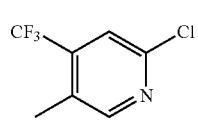 | D-46d | 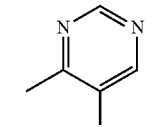 |
| D-43g | 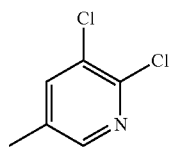 | D-47a | 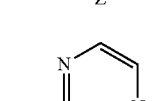 |
| D-44a | 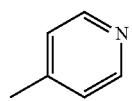 | D-47b | 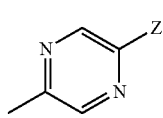 |
| D-44b | 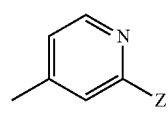 | D-47c | 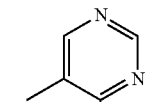 |
| D-44c | 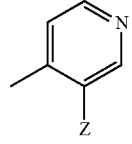 | D-48a | 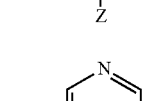 |
| D-44d | 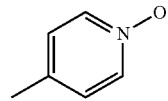 | D-48b | 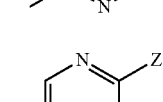 |
| D-45a | 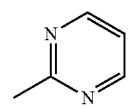 | D-48c | 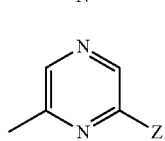 |

-continued

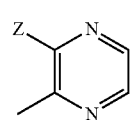 D-48d

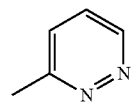 D-49a

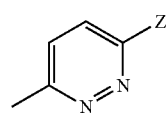 D-49b

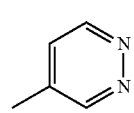 D-50a

For example, the expression (CH$_2$(D-14a)CH$_3$) represents a 1-methylpyrazol-5-ylmethyl group, and (CH$_2$(D-19b)CH$_3$) represents a 2-methylthiazol-5-ylmethyl group.

In addition, heteroaliphatic groups represented by E-1a to E-8b represent the following structures.

E-1a

E-1b

E-2a

E-2b

E-2c

E-3a

E-4a

E-4b

E-4c

-continued

E-4d

E-5a

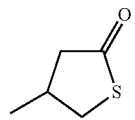 E-5b

E-6a

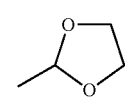 E-6b

E-6c

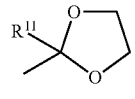 E-7a

E-8a

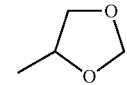 E-8b

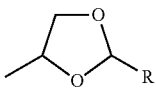

For example, the expression (CH$_2$(E-5b)CH$_3$) represents a 2-methy-1,3-dioxolan-2-ylmethyl group.

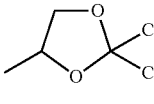 T-1

In Table 1, the expression "-" represents non-substitution.

TABLE 1

| Y | R$^2$ |
|---|---|
| — | CH$_3$ |
| — | F |
| — | Cl |
| — | Br |
| — | I |
| — | CN |
| — | NO$_2$ |

TABLE 1-continued

| Y | R² |
|---|---|
| — | NH₂ |
| — | NHC(O)CH₃ |
| — | NHC(O)OCH₃ |
| — | NHC(O)OEt |
| — | OH |
| — | OC(O)CH₃ |
| — | OCH₂Ph |
| — | OSO₂CH₃ |
| — | OSO₂CF₃ |
| — | OSO₂Ph |
| — | OSO₂(Ph-4-CH₃) |
| — | SCH₃ |
| — | S(O)CH₃ |
| — | SO₂CH₃ |
| — | SEt |
| — | S(O)Et |
| — | SO₂Et |
| — | SCH₂CF₃ |
| — | SPh |
| — | SCH₂(D-42a) |
| — | D-38a |
| — | D-11a |
| — | D-21a |
| — | D-35a |
| — | D-36a-H |
| — | D-36a-Me |
| — | D-36b-Me |
| — | D-39a |
| — | D-40a-H |
| — | D-40a-Me |
| — | C(O)OH |
| — | C(O)OCH₃ |
| — | C(O)OEt |
| — | C(O)NH₂ |
| — | C(O)NHCH₂Pr-c |
| — | C(O)NHCH₂CF₃ |
| — | C(O)N(CH₂OCH₃)CH₂CF₃ |
| — | C(O)N[C(O)CH₃]CH₂CF₃ |
| — | C(O)N[C(O)OCH₃]CH₂CF₃ |
| — | C(O)NHCH₂CH=CH₂ |
| — | C(O)NHCH₂C≡CH |
| — | C(O)NHCH₂CN |
| — | C(O)NHCH₂OCH₂CF₃ |
| — | C(O)NHCH₂CH₂OCH₃ |
| — | C(O)NHCH₂CH₂OEt |
| — | C(O)NHCH=NOCH₃ |
| — | C(O)NHCH=NOEt |
| — | C(O)NHCH₂CH=NOH |
| — | C(O)NHCH₂CH=NOCH₃ |
| — | C(O)NHCH₂C(O)OH |
| — | C(O)NHCH₂C(O)OCH₃ |
| — | C(O)NHCH₂C(O)NH₂ |
| — | C(O)NHCH₂C(O)NHCH₂CH₂Cl |
| — | C(O)NHCH₂C(O)NHCH₂CH₂Br |
| — | C(O)NHCH₂C(O)NHCH₂CF₃ |
| — | C(O)NHCH₂C(O)NHCH₂CH₂OH |
| — | C(O)NHCH(CH₃)C(O)OH |
| — | C(O)NHCH(CH₃)C(O)OCH₃ |
| — | C(O)NHCH(CH₃)C(O)NHCH₂CH₂Cl |
| — | C(O)NHCH(CH₃)C(O)NHCH₂CF₃ |
| — | C(O)NHPh |
| — | C(O)NH(Ph-4-F) |
| — | C(O)NH(Ph-4-CN) |
| — | C(O)NH(D-11a) |
| — | C(O)NH(D-42a) |
| — | C(O)NH(D-42d)Cl |
| — | C(O)NH(D-43e)Cl |
| — | C(O)NH(D-45a) |
| — | C(O)N(CH₃)(D-45a) |
| — | C(O)N[C(O)CH₃](D-45a) |
| — | C(O)N[C(O)OCH₃](D-45a) |
| — | C(O)NH(D-45c)Cl |
| — | C(O)N(CH₃)(D-45c)Cl |
| — | C(O)N[C(O)CH₃](D-45c)Cl |
| — | C(O)N[C(O)OCH₃](D-45c)Cl |
| — | C(O)NH(D-46a) |
| — | C(O)NH(D-48a) |
| — | C(O)NH(E-1a) |
| — | C(O)NHCH₂(D-11a) |
| — | C(O)NHCH₂(D-14a)CH₃ |
| — | C(O)NHCH₂(D-14b)Cl |
| — | C(O)NHCH₂(D-18a) |
| — | C(O)NHCH₂(D-19a) |
| — | C(O)N[C(O)CH₃]CH₂(D-19a) |
| — | C(O)N[C(O)Et]CH₂(D-19a) |
| — | C(O)N[C(O)OCH₃]CH₂(D-19a) |
| — | C(O)NHCH₂(D-25a) |
| — | C(O)NHCH₂(D-27a) |
| — | C(O)NHCH₂(D-28a) |
| — | C(O)NHCH₂(D-31a) |
| — | C(O)NHCH₂(D-34a) |
| — | C(O)NHCH₂(D-36a) |
| — | C(O)NHCH₂(D-42a) |
| — | C(O)N(CH₂CN)CH₂(D-42a) |
| — | C(O)N(CH₂OCH₃)CH₂(D-42a) |
| — | C(O)N[C(O)CH₃]CH₂(D-42a) |
| — | C(O)N[C(O)Et]CH₂(D-42a) |
| — | C(O)N[C(O)OCH₃]CH₂(D-42a) |
| — | C(O)NHCH₂(D-44a) |
| — | C(O)NHCH₂(D-45a) |
| — | C(O)NHCH₂(D-46a) |
| — | C(O)NHCH₂(D-48a) |
| — | C(O)NHCH₂(E-1a) |
| — | C(O)NHC(O)OCH₃ |
| — | C(O)N(CH₃)C(O)OCH₃ |
| — | C(O)N(Et)C(O)OCH₃ |
| — | C(O)N(CH₂CN)C(O)OCH₃ |
| — | C(O)N(CH₂OCH₃)C(O)OCH₃ |
| — | C(O)N[C(O)Et]C(O)OCH₃ |
| — | C(O)N[C(O)Pr-n]C(O)OCH₃ |
| — | C(O)N[C(O)Pr-i]C(O)OCH₃ |
| — | C(O)N[C(O)OCH₃]C(O)OCH₃ |
| — | C(O)NHC(O)OEt |
| — | C(O)N(CH₃)C(O)OEt |
| — | C(O)N(Et)C(O)OEt |
| — | C(O)N(CH₂CN)C(O)OEt |
| — | C(O)N(CH₂OCH₃)C(O)OEt |
| — | C(O)N[C(O)CH₃]C(O)OEt |
| — | C(O)N[C(O)Et]C(O)OEt |
| — | C(O)N[C(O)Pr-n]C(O)OEt |
| — | C(O)N[C(O)Pr-i]C(O)OEt |
| — | C(O)N[C(O)OCH₃]C(O)OEt |
| — | C(O)NHC(O)OPr-i |
| — | C(O)N(CH₃)C(O)OPr-i |
| — | C(O)N(Et)C(O)OPr-i |
| — | C(O)N(CH₂CN)C(O)OPr-i |
| — | C(O)N(CH₂OCH₃)C(O)OPr-i |
| — | C(O)N[C(O)CH₃]C(O)OPr-i |
| — | C(O)N[C(O)Et]C(O)OPr-i |
| — | C(O)N[C(O)Pr-n]C(O)OPr-i |
| — | C(O)N[C(O)Pr-i]C(O)OPr-i |
| — | C(O)N[C(O)OCH₃]C(O)OPr-i |
| — | C(O)N[C(O)OEt]C(O)OPr-i |
| — | C(O)NHC(O)NH₂ |
| — | C(O)NHN(CH₃)Ph |
| — | C(O)N[C(O)CH₃]N(CH₃)Ph |
| — | C(O)N[C(O)OCH₃]N(CH₃)Ph |
| — | C(O)NHN(CH₃)(D-45a) |
| — | C(O)N[C(O)CH₃]N(CH₃)(D-45a) |
| — | C(O)N[C(O)OCH₃]N(CH₃)(D-45a) |
| — | CH₂NH C(O)Pr-i |
| — | CH₂NH C(O)CF₃ |
| — | CH₂NH C(O)OEt |
| — | CH₂NH C(O)(Ph-2-CH₃) |
| — | CH₂NH C(O)NH(Ph-2-F) |
| — | CH₂N(CH₃)C(O)Me |
| — | CH₂N(i-Pr)C(O)Et |
| — | CH(CH₃)NHC(O) CHF₂ |
| — | CH₂(T-1) |
| NO₂ | Cl |
| NO₂ | Br |
| NO₂ | I |
| NO₂ | CN |
| NO₂ | NH₂ |
| NO₂ | NHC(O)CH₃ |
| NO₂ | NHC(O)OCH₃ |

TABLE 1-continued

| Y | R² |
|---|---|
| NO₂ | NHC(O)OEt |
| NO₂ | OH |
| NO₂ | OC(O)CH₃ |
| NO₂ | OCH₂Ph |
| NO₂ | OSO₂CH₃ |
| NO₂ | OSO₂CF₃ |
| NO₂ | OSO₂Ph |
| NO₂ | OSO₂(Ph-4-CH₃) |
| NO₂ | SCH₃ |
| NO₂ | S(O)CH₃ |
| NO₂ | SO₂CH₃ |
| NO₂ | SEt |
| NO₂ | S(O)Et |
| NO₂ | SO₂Et |
| NO₂ | SCH₂CF₃ |
| NO₂ | SPh |
| NO₂ | SCH₂(D-42a) |
| NO₂ | D-38a |
| NO₂ | D-11a |
| NO₂ | D-21a |
| NO₂ | D-35a |
| NO₂ | D-36a-H |
| NO₂ | D-36a-Me |
| NO₂ | D-36b-Me |
| NO₂ | D-39a |
| NO₂ | D-40a-H |
| NO₂ | D-40a-Me |
| NO₂ | C(O)OH |
| NO₂ | C(O)OCH₃ |
| NO₂ | C(O)OEt |
| NO₂ | C(O)NH₂ |
| NO₂ | C(O)NHCH₂Pr-c |
| NO₂ | C(O)NHCH₂CF₃ |
| NO₂ | C(O)N(CH₂OCH₃)CH₂CF₃ |
| NO₂ | C(O)N[C(O)CH₃]CH₂CF₃ |
| NO₂ | C(O)N[C(O)OCH₃]CH₂CF₃ |
| NO₂ | C(O)NHCH₂CH=CH₂ |
| NO₂ | C(O)NHCH₂CH=CH |
| NO₂ | C(O)NHCH₂CN |
| NO₂ | C(O)NHCH₂CH₂CF₃ |
| NO₂ | C(O)NHCH₂CH₂OCH₃ |
| NO₂ | C(O)NHCH₂CH₂OEt |
| NO₂ | C(O)NHCH=NOCH₃ |
| NO₂ | C(O)NHCH=NOEt |
| NO₂ | C(O)NHCH₂CH=NOH |
| NO₂ | C(O)NHCH₂CH=NOCH₃ |
| NO₂ | C(O)NHCH₂C(O)OH |
| NO₂ | C(O)NHCH₂C(O)OCH₃ |
| NO₂ | C(O)NHCH₂C(O)NH₃ |
| NO₂ | C(O)NHCH₂C(O)NHCH₂CH₂Cl |
| NO₂ | C(O)NHCH₂C(O)NHCH₂CH₂Br |
| NO₂ | C(O)NHCH₂C(O)NHCH₂CF₃ |
| NO₂ | C(O)NHCH₂C(O)NHCH₂CH₂OH |
| NO₂ | C(O)NHCH(CH₃)C(O)OH |
| NO₂ | C(O)NHCH(CH₃)C(O)OCH₃ |
| NO₂ | C(O)NHCH(CH₃)C(O)NHCH₂CH₂Cl |
| NO₂ | C(O)NHCH(CH₃)C(O)NHCH₂CF₃ |
| NO₂ | C(O)NHPh |
| NO₂ | C(O)NH(Ph-4-F) |
| NO₂ | C(O)NH(Ph-4-CN) |
| NO₂ | C(O)NH(D-11a) |
| NO₂ | C(O)NH(D-42a) |
| NO₂ | C(O)NH(D-42d)Cl |
| NO₂ | C(O)NH(D-43e)Cl |
| NO₂ | C(O)NH(D-45a) |
| NO₂ | C(O)N(CH₃)(D-45a) |
| NO₂ | C(O)N[C(O)CH₃](D-45a) |
| NO₂ | C(O)N[C(O)OCH₃](D-45a) |
| NO₂ | C(O)NH(D-45c)Cl |
| NO₂ | C(O)N(CH₃)(D-45c)Cl |
| NO₂ | C(O)N[C(O)CH₃](D-45c)Cl |
| NO₂ | C(O)N[C(O)OCH₃](D-45c)Cl |
| NO₂ | C(O)NH(D-46a) |
| NO₂ | C(O)NH(D-48a) |
| NO₂ | C(O)NH(E-1a) |
| NO₂ | C(O)NHCH₂(D-11a) |
| NO₂ | C(O)NHCH₂(D-14a)CH₃ |
| NO₂ | C(O)NHCH₂(D-14b)Cl |
| NO₂ | C(O)NHCH₂(D-18a) |
| NO₂ | C(O)NHCH₂(D-19a) |
| NO₂ | C(O)N[C(O)CH₃]CH₂(D-19a) |
| NO₂ | C(O)N[C(O)Et]CH₂(D-19a) |
| NO₂ | C(O)N[C(O)OCH₃]CH₂(D-19a) |
| NO₂ | C(O)NHCH₂(D-25a) |
| NO₂ | C(O)NHCH₂(D-27a) |
| NO₂ | C(O)NHCH₂(D-28a) |
| NO₂ | C(O)NHCH₂(D-31a) |
| NO₂ | C(O)NHCH₂(D-34a) |
| NO₂ | C(O)NHCH₂(D-36a) |
| NO₂ | C(O)NHCH₂(D-42a) |
| NO₂ | C(O)N(CH₂CN)CH₂(D-42a) |
| NO₂ | C(O)N(CH₂OCH₃)CH₂(D-42a) |
| NO₂ | C(O)N[C(O)CH₃]CH₂(D-42a) |
| NO₂ | C(O)N[C(O)Et]CH₂(D-42a) |
| NO₂ | C(O)N[C(O)OCH₃]CH₂(D-42a) |
| NO₂ | C(O)NHCH₂(D-44a) |
| NO₂ | C(O)NHCH₂(D-45a) |
| NO₂ | C(O)NHCH₂(D-46a) |
| NO₂ | C(O)NHCH₂(D-48a) |
| NO₂ | C(O)NHCH₂(E-1a) |
| NO₂ | C(O)NHCH₂(E-3a) |
| NO₂ | C(O)NHCH₂(E-5a) |
| NO₂ | C(O)NHC(O)OCH₃ |
| NO₂ | C(O)N(CH₃)C(O)OCH₃ |
| NO₂ | C(O)N(Et)C(O)OCH₃ |
| NO₂ | C(O)N(CH₂CN)C(O)OCH₃ |
| NO₂ | C(O)N(CH₂OCH₃)C(O)OCH₃ |
| NO₂ | C(O)N[C(O)Et]C(O)OCH₃ |
| NO₂ | C(O)N[C(O)Pr-n]C(O)OCH₃ |
| NO₂ | C(O)N[C(O)Pr-i]C(O)OCH₃ |
| NO₂ | C(O)N[C(O)OCH₃]C(O)OCH₃ |
| NO₂ | C(O)NHC(O)OEt |
| NO₂ | C(O)N(CH₃)C(O)OEt |
| NO₂ | C(O)N(Et)C(O)OEt |
| NO₂ | C(O)N(CH₂CN)C(O)OEt |
| NO₂ | C(O)N(CH₂OCH₃)C(O)OEt |
| NO₂ | C(O)N[C(O)CH₃]C(O)OEt |
| NO₂ | C(O)N[C(O)Et]C(O)OEt |
| NO₂ | C(O)N[C(O)Pr-n]C(O)OEt |
| NO₂ | C(O)N[C(O)Pr-i]C(O)OEt |
| NO₂ | C(O)N[C(O)OCH₃]C(O)OEt |
| NO₂ | C(O)NHC(O)OPr-i |
| NO₂ | C(O)N(CH₃)C(O)OPr-i |
| NO₂ | C(O)N(Et)C(O)OPr-i |
| NO₂ | C(O)N(CH₂CN)C(O)OPr-i |
| NO₂ | C(O)N(CH₂OCH₃)C(O)OPr-i |
| NO₂ | C(O)N[C(O)CH₃]C(O)OPr-i |
| NO₂ | C(O)N[C(O)Et]C(O)OPr-i |
| NO₂ | C(O)N[C(O)Pr-n]C(O)OPr-i |
| NO₂ | C(O)N[C(O)Pr-i]C(O)OPr-i |
| NO₂ | C(O)N[C(O)OCH₃]C(O)OPr-i |
| NO₂ | C(O)N[C(O)OEt]C(O)OPr-i |
| NO₂ | C(O)NHC(O)NH₂ |
| NO₂ | C(O)NHN(CH₃)Ph |
| NO₂ | C(O)N[C(O)CH₃]N(CH₃)Ph |
| NO₂ | C(O)N[C(O)OCH₃]N(CH₃)Ph |
| NO₂ | C(O)NHN(CH₃)(D-45a) |
| NO₂ | C(O)N[C(O)CH₃]N(CH₃)(D-45a) |
| NO₂ | C(O)N[C(O)OCH₃]N(CH₃)(D-45a) |
| NO₂ | CH₂NH C(O)Pr-i |
| NO₂ | CH₂NH C(O)CF₃ |
| NO₂ | CH₂NH C(O)OEt |
| NO₂ | CH₂NH C(O)(Ph-2-CH₃) |
| NO₂ | CH₂NH C(O)NH(Ph-2-F) |
| NO₂ | CH₂N(CH₃)C(O)Me |
| NO₂ | CH₂N(i-Pr)C(O)Et |
| NO₂ | CH(CH₃)NHC(O) CHF₂ |
| NO₂ | CH₂(T-1) |
| CH₃ | F |
| CH₃ | Cl |
| CH₃ | Br |
| CH₃ | I |
| CH₃ | CN |
| CH₃ | NO₂ |
| CH₃ | NH₂ |
| CH₃ | NHC(O)CH₃ |

TABLE 1-continued

| Y | R² |
|---|---|
| CH₃ | NHC(O)OCH₃ |
| CH₃ | NHC(O)OEt |
| CH₃ | OH |
| CH₃ | OC(O)CH₃ |
| CH₃ | OCH₂Ph |
| CH₃ | OSO₂CH₃ |
| CH₃ | OSO₂CF₃ |
| CH₃ | OSO₂Ph |
| CH₃ | OSO₂(Ph-4-CH₃) |
| CH₃ | SCH₃ |
| CH₃ | S(O)CH₃ |
| CH₃ | SO₂CH₃ |
| CH₃ | SEt |
| CH₃ | S(O)Et |
| CH₃ | SO₂Et |
| CH₃ | SCH₂CF₃ |
| CH₃ | SPh |
| CH₃ | SCH₂(D-42a) |
| CH₃ | D-38a |
| CH₃ | D-11a |
| CH₃ | D-21a |
| CH₃ | D-35a |
| CH₃ | D-36a-H |
| CH₃ | D-36a-Me |
| CH₃ | D-36b-Me |
| CH₃ | D-39a |
| CH₃ | D-40a-H |
| CH₃ | D-40a-Me |
| CH₃ | C(O)OH |
| CH₃ | C(O)OCH₃ |
| CH₃ | C(O)OEt |
| CH₃ | C(O)NH₂ |
| CH₃ | C(O)NHCH₃ |
| CH₃ | C(O)NHEt |
| CH₃ | C(O)NHCH₂Pr-c |
| CH₃ | C(O)N(CH₃)CH₂Pr-c |
| CH₃ | C(O)N[C(O)CH₃]CH₂Pr-c |
| CH₃ | C(O)N[C(O)OCH₃]CH₂Pr-c |
| CH₃ | C(O)NHCH₂CF₃ |
| CH₃ | C(O)N(CH₃)CH₂CF₃ |
| CH₃ | C(O)N(Et)CH₂CF₃ |
| CH₃ | C(O)N(CH₂OCH₃)CH₂CF₃ |
| CH₃ | C(O)N[C(O)CH₃]CH₂CF₃ |
| CH₃ | C(O)N[C(O)OCH₃]CH₂CF₃ |
| CH₃ | C(O)NHCH₂CH=CH₂ |
| CH₃ | C(O)NHCH₂CH=CH |
| CH₃ | C(O)NHCH₂OCH₂CF₃ |
| CH₃ | C(O)NHCH₂CH₂OCH₃ |
| CH₃ | C(O)NHCH₂CH₂OEt |
| CH₃ | C(O)NHCH=NOCH₃ |
| CH₃ | C(O)NHC(CH₃)=NOCH₃ |
| CH₃ | C(O)NHCH=NOEt |
| CH₃ | C(O)NHCH₂CH=NOH |
| CH₃ | C(O)NHCH₂CH=NOCH₃ |
| CH₃ | C(O)NHCH₂C(CH₃)=CNOCH₃ |
| CH₃ | C(O)NHCH₂CN |
| CH₃ | C(O)NHCH(CN)OCH₂CF₃ |
| CH₃ | C(O)NHCH₂C(O)OH |
| CH₃ | C(O)NHCH₂C(O)OCH₃ |
| CH₃ | C(O)NHCH₂C(O)OEt |
| CH₃ | C(O)NHCH₂C(O)OCH₂CF₃ |
| CH₃ | C(O)NHCH₂C(O)NH₂ |
| CH₃ | C(O)NHCH₂C(O)NHCH₃ |
| CH₃ | C(O)NHCH₂C(O)N(CH₃)₂ |
| CH₃ | C(O)NHCH₂C(O)NHEt |
| CH₃ | C(O)NHCH₂C(O)NHCH₂CH₂Cl |
| CH₃ | C(O)NHCH₂C(O)N(CH₃)CH₂CH₂Cl |
| CH₃ | C(O)N(CH₃)CH₂C(O)NHCH₂CH₂Cl |
| CH₃ | C(O)N[C(O)CH₃]CH₂C(O)NHCH₂CH₂Cl |
| CH₃ | C(O)N[C(O)OCH₃]CH₂C(O)NHCH₂CH₂Cl |
| CH₃ | C(O)NHCH₂C(O)NHCH₂CH₂Br |
| CH₃ | C(O)NHCH₂C(O)NHCH₂CF₃ |
| CH₃ | C(O)NHCH₂C(O)N(CH₃)CH₂CF₃ |
| CH₃ | C(O)N(CH₃)CH₂C(O)NHCH₂CF₃ |
| CH₃ | C(O)N[C(O)CH₃]CH₂C(O)NHCH₂CF₃ |
| CH₃ | C(O)N[C(O)OCH₃]CH₂C(O)NHCH₂CF₃ |
| CH₃ | C(O)NHCH₂C(O)NHCH₂CH₂OH |
| CH₃ | C(O)NHCH(CH₃)C(O)OH |
| CH₃ | C(O)NHCH(CH₃)C(O)OCH₃ |
| CH₃ | C(O)NHCH(CH₃)C(O)NHCH₂CH₂Cl |
| CH₃ | C(O)NHCH(CH₃)C(O)NHCH₂CF₃ |
| CH₃ | C(O)NHCH₂(E-1a) |
| CH₃ | C(O)NHCH₂(E-2a) |
| CH₃ | C(O)NHCH₂(E-3a) |
| CH₃ | C(O)NHCH₂(E-5a) |
| CH₃ | C(O)NHCH₂(E-7a) |
| CH₃ | C(O)NHPh |
| CH₃ | C(O)NH(Ph-4-F) |
| CH₃ | C(O)N(CH₃)(Ph-4-F) |
| CH₃ | C(O)N(Et)(Ph-4-F) |
| CH₃ | C(O)N(CH₂CH=CH₂)(Ph-4-F) |
| CH₃ | C(O)N(CH₂CN)(Ph-4-F) |
| CH₃ | C(O)N(CH₂OCH₃)(Ph-4-F) |
| CH₃ | C(O)N[C(O)CH₃](Ph-4-F) |
| CH₃ | C(O)N[C(O)OCH₃](Ph-4-F) |
| CH₃ | C(O)NH(Ph-4-CN) |
| CH₃ | C(O)N(CH₃)(Ph-4-CN) |
| CH₃ | C(O)N[C(O)CH₃](Ph-4-CN) |
| CH₃ | C(O)N[C(O)OCH₃](Ph-4-CN) |
| CH₃ | C(O)NH(Ph-4-NO2) |
| CH₃ | C(O)NH(D-5a) |
| CH₃ | C(O)NH(D-5b)CH₃ |
| CH₃ | C(O)NH(D-10b)CH₃ |
| CH₃ | C(O)NH(D-11a) |
| CH₃ | C(O)N(CH₃)(D-11a) |
| CH₃ | C(O)N[C(O)CH₃](D-11a) |
| CH₃ | C(O)N[C(O)OCH₃](D-11a) |
| CH₃ | C(O)NH(D-12a)CH₃ |
| CH₃ | C(O)NH(D-18a) |
| CH₃ | C(O)NH(D-32a) |
| CH₃ | C(O)NH(D-42a) |
| CH₃ | C(O)N(CH₃)(D-42a) |
| CH₃ | C(O)N[C(O)CH₃](D-42a) |
| CH₃ | C(O)N[C(O)OCH₃](D-42a) |
| CH₃ | C(O)NH(D-42d)Cl |
| CH₃ | C(O)NH(D-43e)Cl |
| CH₃ | C(O)N(CH₃)(D-43e)Cl |
| CH₃ | C(O)N[C(O)CH₃](D-43e)Cl |
| CH₃ | C(O)N[C(O)OCH₃](D-43e)Cl |
| CH₃ | C(O)NH(D-45a) |
| CH₃ | C(O)N(CH₃)(D-45a) |
| CH₃ | C(O)N[C(O)CH₃](D-45a) |
| CH₃ | C(O)N[C(O)OCH₃](D-45a) |
| CH₃ | C(O)NH(D-45b)CH₃ |
| CH₃ | C(O)NH(D-45c)Cl |
| CH₃ | C(O)N(CH₃)(D-45c)Cl |
| CH₃ | C(O)N[C(O)CH₃](D-45c)Cl |
| CH₃ | C(O)N[C(O)OCH₃](D-45c)Cl |
| CH₃ | C(O)NH(D-45c)Br |
| CH₃ | C(O)N[C(O)CH₃](D-45c)Br |
| CH₃ | C(O)N[C(O)OCH₃](D-45c)Br |
| CH₃ | C(O)NH(D-46a) |
| CH₃ | C(O)NH(D-48a) |
| CH₃ | C(O)NH(E-1a) |
| CH₃ | C(O)NHCH₂Ph |
| CH₃ | C(O)NHCH(CH₃)Ph |
| CH₃ | C(O)NHCH(CF₃)Ph |
| CH₃ | C(O)NHCH(CN)Ph |
| CH₃ | C(O)NHCH₂(Ph-4-NO₂) |
| CH₃ | C(O)NHCH₂(D-8a) |
| CH₃ | C(O)NHCH₂(D-11a) |
| CH₃ | C(O)NHCH(CN)(D-11a) |
| CH₃ | C(O)NHCH₂(D-12a)CH₃ |
| CH₃ | C(O)NHCH₂(D-13b)Cl |
| CH₃ | C(O)NHCH₂(D-13c)Cl |
| CH₃ | C(O)NHCH₂(D-14a)CH₃ |
| CH₃ | C(O)NHCH₂(D-14b)Cl |
| CH₃ | C(O)NHCH₂(D-18a) |
| CH₃ | C(O)NHCH₂(D-19a) |
| CH₃ | C(O)N(CH₃)CH₂(D-19a) |
| CH₃ | C(O)N[C(O)CH₃]CH₂(D-19a) |
| CH₃ | C(O)N[C(O)Et]CH₂(D-19a) |
| CH₃ | C(O)N[C(O)OCH₃]CH₂(D-19a) |
| CH₃ | C(O)NHCH₂(D-20a) |
| CH₃ | C(O)NHCH₂(D-22a)CH₃ |
| CH₃ | C(O)NHCH₂(D-24a)CH₃ |

TABLE 1-continued

| Y | R² |
|---|---|
| CH₃ | C(O)NHCH₂(D-25a) |
| CH₃ | C(O)NHCH₂(D-27a) |
| CH₃ | C(O)NHCH₂(D-28a) |
| CH₃ | C(O)NHCH₂(D-31a) |
| CH₃ | C(O)NHCH₂(D-34a) |
| CH₃ | C(O)NHCH₂(D-36a) |
| CH₃ | C(O)NHCH(CN)(D-36a) |
| CH₃ | C(O)NHCH₂(D-42a) |
| CH₃ | C(O)NHCH(CH₃)(D-42a) |
| CH₃ | C(O)NHCH(CF₂)(D-42a) |
| CH₃ | C(O)NHCH(CN)(D-42a) |
| CH₃ | C(O)N(CH₃)CH₂(D-42a) |
| CH₃ | C(O)N(CH₂C≡CH)CH₂(D-42a) |
| CH₃ | C(O)N(CH₂CN)CH₂(D-42a) |
| CH₃ | C(O)N(CH₂OCH₃)CH₂(D-42a) |
| CH₃ | C(O)N[C(O)CH₃]CH₂(D-42a) |
| CH₃ | C(O)N[C(O)Et]CH₂(D-42a) |
| CH₃ | C(O)N[C(O)OCH₃]CH₂(D-42a) |
| CH₃ | C(O)NHCH₂(D-44a) |
| CH₃ | C(O)NHCH₂(D-45a) |
| CH₃ | C(O)NHCH₂(D-46a) |
| CH₃ | C(O)NHCH₂(D-48a) |
| CH₃ | C(O)NHC(O)OCH₃ |
| CH₃ | C(O)N(CH₃)C(O)OCH₃ |
| CH₃ | C(O)N(Et)C(O)OCH₃ |
| CH₃ | C(O)N(CH₂CN)C(O)OCH₃ |
| CH₃ | C(O)N(CH₂OCH₃)C(O)OCH₃ |
| CH₃ | C(O)N[C(O)CH₃]C(O)OCH₃ |
| CH₃ | C(O)N[C(O)Et]C(O)OCH₃ |
| CH₃ | C(O)N[C(O)Pr-n]C(O)OCH₃ |
| CH₃ | C(O)N[C(O)Pr-i]C(O)OCH₃ |
| CH₃ | C(O)N[C(O)OCH₃]C(O)OCH₃ |
| CH₃ | C(O)NHC(O)OEt |
| CH₃ | C(O)N(CH₃)C(O)OEt |
| CH₃ | C(O)N(Et)C(O)OEt |
| CH₃ | C(O)N(CH₂CN)C(O)OEt |
| CH₃ | C(O)N(CH₂OCH₃)C(O)OEt |
| CH₃ | C(O)N[C(O)CH₃]C(O)OEt |
| CH₃ | C(O)N[C(O)Et]C(O)OEt |
| CH₃ | C(O)N[C(O)Pr-n]C(O)OEt |
| CH₃ | C(O)N[C(O)Pr-i]C(O)OEt |
| CH₃ | C(O)N[C(O)OCH₃]C(O)OEt |
| CH₃ | C(O)NHC(O)OPr-i |
| CH₃ | C(O)N(CH₃)C(O)OPr-i |
| CH₃ | C(O)N(Et)C(O)OPr-i |
| CH₃ | C(O)N(CH₂CN)C(O)OPr-i |
| CH₃ | C(O)N(CH₂OCH₃)C(O)OPr-i |
| CH₃ | C(O)N[C(O)CH₃]C(O)OPr-i |
| CH₃ | C(O)N[C(O)Et]C(O)OPr-i |
| CH₃ | C(O)N[C(O)Pr-n]C(O)OPr-i |
| CH₃ | C(O)N[C(O)Pr-i]C(O)OPr-i |
| CH₃ | C(O)N[C(O)OCH₃]C(O)OPr-i |
| CH₃ | C(O)N[C(O)OEt]C(O)OPr-i |
| CH₃ | C(O)NHC(O)NH₂ |
| CH₃ | C(O)NHC(O)NHCH₃ |
| CH₃ | C(O)NHNH₂ |
| CH₃ | C(O)NHNHPh |
| CH₃ | C(O)NHN(CH₃)Ph |
| CH₃ | C(O)N(CH₃)NHPh |
| CH₃ | C(O)N(CH₃)N(CH₃)Ph |
| CH₃ | C(O)N[C(O)CH₃]N(CH₃)Ph |
| CH₃ | C(O)N[C(O)OCH₃]N(CH₃)Ph |
| CH₃ | C(O)NHNH(D-45a) |
| CH₃ | C(O)NHN(CH₃)(D-45a) |
| CH₃ | C(O)N(CH₃)N(CH₃)(D-45a) |
| CH₃ | C(O)N[C(O)CH₃]N(CH₃)(D-45a) |
| CH₃ | C(O)N[C(O)OCH₃]N(CH₃)(D-45a) |
| CH₃ | CH₂NH C(O)Pr-i |
| CH₃ | CH₂NH C(O)CF₃ |
| CH₃ | CH₂NH C(O)OEt |
| CH₃ | CH₂NH C(O)(Ph-2-CH₃) |
| CH₃ | CH₂NH C(O)NH(Ph-2-F) |
| CH₃ | CH₂N(CH₃)C(O)Me |
| CH₃ | CH₂N(i-Pr)C(O)Et |
| CH₃ | CH(CH₃)NHC(O) CHF₂ |
| CH₃ | CH₂(T-1) |
| Et | F |
| Et | Cl |
| Et | Br |
| Et | I |
| Et | NO₂ |
| Et | NH₂ |
| Et | NHC(O)CH₃ |
| Et | NHC(O)OCH₃ |
| Et | NHC(O)OEt |
| Et | OH |
| Et | OC(O)CH₃ |
| Et | OCH₂Ph |
| Et | OSO₂CH₃ |
| Et | OSO₂CF₃ |
| Et | OSO₂Ph |
| Et | OSO₂(Ph-4-CH₃) |
| Et | SCH₃ |
| Et | S(O)CH₃ |
| Et | SO₂CH₃ |
| Et | SEt |
| Et | S(O)Et |
| Et | SO₂Et |
| Et | SCH₂CF₃ |
| Et | SPh |
| Et | SCH₂(D-42a) |
| Et | D-38a |
| Et | D-11a |
| Et | D-21a |
| Et | D-35a |
| Et | D-36a-H |
| Et | D-36a-Me |
| Et | D-36b-Me |
| Et | D-39a |
| Et | D-40a-H |
| Et | D-40a-Me |
| Et | C(O)OH |
| Et | C(O)OCH₃ |
| Et | C(O)OEt |
| Et | C(O)NH₂ |
| Et | C(O)NHCH₂Pr-c |
| Et | C(O)NHCH₂CF₃ |
| Et | C(O)NHCH₂CH═CH₂ |
| Et | C(O)NHCH₂CH═CH |
| Et | C(O)NHCH₂CN |
| Et | C(O)NHCH₂OCH₂CF₃ |
| Et | C(O)NHCH₂CH₂OCH₃ |
| Et | C(O)NHCH₂CH₂OEt |
| Et | C(O)NHCH═NOCH₃ |
| Et | C(O)NHCH═NOEt |
| Et | C(O)NHCH₂CH═NOH |
| Et | C(O)NHCH₂CH═NOCH₃ |
| Et | C(O)NHCH₂C(O)OH |
| Et | C(O)NHCH₂C(O)OCH₃ |
| Et | C(O)NHCH₂C(O)OEt |
| Et | C(O)NHCH₂C(O)NH₂ |
| Et | C(O)NHCH₂C(O)NHCH₂CF₃ |
| Et | C(O)NHCH(CH₃)C(O)OH |
| Et | C(O)NHCH(CH₃)C(O)OCH₃ |
| Et | C(O)NHCH(CH₃)C(O)NHCH₂CF₃ |
| Et | C(O)NH(D-11a) |
| Et | C(O)NH(D-42a) |
| Et | C(O)NH(D-42d)Cl |
| Et | C(O)NH(D-43e)Cl |
| Et | C(O)NH(D-45a) |
| Et | C(O)N[C(O)CH₃](D-45a) |
| Et | C(O)N[C(O)OCH₃](D-45a) |
| Et | C(O)NH(D-45c)Cl |
| Et | C(O)N[C(O)CH₃](D-45c)Cl |
| Et | C(O)N[C(O)OCH₃](D-45c)Cl |
| Et | C(O)NH(D-46a) |
| Et | C(O)NH(D-48a) |
| Et | C(O)NH(E-1a) |
| Et | C(O)NHCH₂(D-11a) |
| Et | C(O)NHCH₂(D-14a)CH₃ |
| Et | C(O)NHCH₂(D-14b)Cl |
| Et | C(O)NHCH₂(D-18a) |
| Et | C(O)NHCH₂(D-19a) |
| Et | C(O)N[C(O)CH₃]CH₂(D-19a) |
| Et | C(O)N[C(O)Et]CH₂(D-19a) |
| Et | C(O)N[C(O)OCH₃]CH₂(D-19a) |

TABLE 1-continued

| Y | R² |
|---|---|
| Et | C(O)NHCH₂(D-25a) |
| Et | C(O)NHCH₂(D-27a) |
| Et | C(O)NHCH₂(D-28a) |
| Et | C(O)NHCH₂(D-31a) |
| Et | C(O)NHCH₂(D-34a) |
| Et | C(O)NHCH₂(D-36a) |
| Et | C(O)NHCH₂(D-42a) |
| Et | C(O)N(CH₂OCH₃)CH₂(D-42a) |
| Et | C(O)N[C(O)CH₃]CH₂(D-42a) |
| Et | C(O)N[C(O)Et]CH₂(D-42a) |
| Et | C(O)N[C(O)OCH₃]CH₂(D-42a) |
| Et | C(O)NHCH₂(D-44a) |
| Et | C(O)NHCH₂(D-45a) |
| Et | C(O)NHCH₂(D-46a) |
| Et | C(O)NHCH₂(D-48a) |
| Et | C(O)NHCH₂(E-1a) |
| Et | C(O)NHCH₂(E-3a) |
| Et | C(O)NHCH₂(E-5a) |
| Et | C(O)NHC(O)OCH₃ |
| Et | C(O)N(CH₃)C(O)OCH₃ |
| Et | C(O)N(Et)C(O)OCH₃ |
| Et | C(O)N(CH₂OCH₃)C(O)OCH₃ |
| Et | C(O)N[C(O)Et]C(O)OCH₃ |
| Et | C(O)N[C(O)Pr-n]C(O)OCH₃ |
| Et | C(O)N[C(O)Pr-i]C(O)OCH₃ |
| Et | C(O)N[C(O)OCH₃]C(O)OCH₃ |
| Et | C(O)NHC(O)OEt |
| Et | C(O)N(CH₃)C(O)OEt |
| Et | C(O)N(Et)C(O)OEt |
| Et | C(O)N(CH₂OCH₃)C(O)OEt |
| Et | C(O)N[C(O)CH₃]C(O)OEt |
| Et | C(O)N[C(O)Et]C(O)OEt |
| Et | C(O)N[C(O)Pr-n]C(O)OEt |
| Et | C(O)N[C(O)Pr-i]C(O)OEt |
| Et | C(O)N[C(O)OCH₃]C(O)OEt |
| Et | C(O)NHC(O)OPr-i |
| Et | C(O)N(CH₃)C(O)OPr-i |
| Et | C(O)N(Et)C(O)OPr-i |
| Et | C(O)N(CH₂OCH₃)C(O)OPr-i |
| Et | C(O)N[C(O)CH₃]C(O)OPr-i |
| Et | C(O)N[C(O)Et]C(O)OPr-i |
| Et | C(O)N[C(O)Pr-n]C(O)OPr-i |
| Et | C(O)N[C(O)Pr-i]C(O)OPr-i |
| Et | C(O)N[C(O)OCH₃]C(O)OPr-i |
| Et | C(O)N[C(O)OEt]C(O)OPr-i |
| Et | C(O)NHC(O)NH₂ |
| Et | C(O)NHN(CH₃)Ph |
| Et | C(O)N[C(O)CH₃]N(CH₃)Ph |
| Et | C(O)N[C(O)OCH₃]N(CH₃)Ph |
| Et | C(O)NHN(CH₃)(D-45a) |
| Et | C(O)N[C(O)CH₃]N(CH₃)(D-45a) |
| Et | C(O)N[C(O)OCH₃]N(CH₃)(D-45a) |
| Et | CH₂NH C(O)Pr-i |
| Et | CH₂NH C(O)CF₃ |
| Et | CH₂NH C(O)OEt |
| Et | CH₂NH C(O)(Ph-2-CH₃) |
| Et | CH₂NH C(O)NH(Ph-2-F) |
| Et | CH₂N(CH₃)C(O)Me |
| Et | CH₂N(i-Pr)C(O)Et |
| Et | CH(CH₃)NHC(O) CHF₂ |
| Et | CH₂(T-1) |
| CF₃ | F |
| CF₃ | Cl |
| CF₃ | Br |
| CF₃ | I |
| CF₃ | NO₂ |
| CF₃ | NH₂ |
| CF₃ | NHC(O)CH₃ |
| CF₃ | NHC(O)OCH₃ |
| CF₃ | NHC(O)OEt |
| CF₃ | OH |
| CF₃ | OC(O)CH₃ |
| CF₃ | OCH₂Ph |
| CF₃ | OSO₂CH₃ |
| CF₃ | OSO₂CF₃ |
| CF₃ | OSO₂Ph |
| CF₃ | OSO₂(Ph-4-CH₃) |
| CF₃ | SCH₃ |
| CF₃ | S(O)CH₃ |
| CF₃ | SO₂CH₃ |
| CF₃ | SEt |
| CF₃ | S(O)Et |
| CF₃ | SO₂Et |
| CF₃ | SCH₂CF₃ |
| CF₃ | SPh |
| CF₃ | SCH₂(D-42a) |
| CF₃ | D-38a |
| CF₃ | D-11a |
| CF₃ | D-21a |
| CF₃ | D-35a |
| CF₃ | D-36a-H |
| CF₃ | D-36a-Me |
| CF₃ | D-36b-Me |
| CF₃ | D-39a |
| CF₃ | D-40a-H |
| CF₃ | D-40a-Me |
| CF₃ | C(O)OH |
| CF₃ | C(O)OCH₃ |
| CF₃ | C(O)OEt |
| CF₃ | C(O)NH₂ |
| CF₃ | C(O)NHCH₂Pr-c |
| CF₃ | C(O)NHCH₂CF₃ |
| CF₃ | C(O)NHCH₂CH=CH₂ |
| CF₃ | C(O)NHCH₂CH=CH |
| CF₃ | C(O)NHCH₂CN |
| CF₃ | C(O)NHCH₂OCH₂CF₃ |
| CF₃ | C(O)NHCH₂CH₂OCH₃ |
| CF₃ | C(O)NHCH₂CH₂OEt |
| CF₃ | C(O)NHCH=NOCH₃ |
| CF₃ | C(O)NHCH=NOEt |
| CF₃ | C(O)NHCH₂CH=NOH |
| CF₃ | C(O)NHCH₂CH=NOCH₃ |
| CF₃ | C(O)NHCH₂C(O)OH |
| CF₃ | C(O)NHCH₂C(O)OCH₃ |
| CF₃ | C(O)NHCH₂C(O)OEt |
| CF₃ | C(O)NHCH₂C(O)NH₂ |
| CF₃ | C(O)NHCH₂C(O)NHCH₂CF₃ |
| CF₃ | C(O)NHCH(CH₃)C(O)OH |
| CF₃ | C(O)NHCH(CH₃)C(O)OCH₃ |
| CF₃ | C(O)NHCH(CH₃)C(O)NHCH₂CF₃ |
| CF₃ | C(O)NH(D-11a) |
| CF₃ | C(O)NH(D-42a) |
| CF₃ | C(O)NH(D-42d)Cl |
| CF₃ | C(O)NH(D-43e)Cl |
| CF₃ | C(O)NH(D-45a) |
| CF₃ | C(O)N[C(O)CH₃](D-45a) |
| CF₃ | C(O)N[C(O)OCH₃](D-45a) |
| CF₃ | C(O)NH(D-45c)Cl |
| CF₃ | C(O)N[C(O)CH₃](D-45c)Cl |
| CF₃ | C(O)N[C(O)OCH₃](D-45c)Cl |
| CF₃ | C(O)NH(D-46a) |
| CF₃ | C(O)NH(D-48a) |
| CF₃ | C(O)NH(E-1a) |
| CF₃ | C(O)NHCH₂(D-11a) |
| CF₃ | C(O)NHCH₂(D-14a)CH₃ |
| CF₃ | C(O)NHCH₂(D-14b)Cl |
| CF₃ | C(O)NHCH₂(D-18a) |
| CF₃ | C(O)NHCH₂(D-19a) |
| CF₃ | C(O)N[C(O)CH₃]CH₂(D-19a) |
| CF₃ | C(O)N[C(O)Et]CH₂(D-19a) |
| CF₃ | C(O)N[C(O)OCH₃]CH₂(D-19a) |
| CF₃ | C(O)NHCH₂(D-25a) |
| CF₃ | C(O)NHCH₂(D-27a) |
| CF₃ | C(O)NHCH₂(D-28a) |
| CF₃ | C(O)NHCH₂(D-31a) |
| CF₃ | C(O)NHCH₂(D-34a) |
| CF₃ | C(O)NHCH₂(D-36a) |
| CF₃ | C(O)NHCH₂(D-42a) |
| CF₃ | C(O)N[C(O)CH₃]CH₂(D-42a) |
| CF₃ | C(O)N[C(O)Et]CH₂(D-42a) |
| CF₃ | C(O)N[C(O)OCH₃]CH₂(D-42a) |
| CF₃ | C(O)NHCH₂(D-44a) |
| CF₃ | C(O)NHCH₂(D-45a) |
| CF₃ | C(O)NHCH₂(D-46a) |
| CF₃ | C(O)NHCH₂(D-48a) |
| CF₃ | C(O)NHCH₂(E-1a) |

TABLE 1-continued

| Y | R² |
|---|---|
| CF₃ | C(O)NHCH₂(E-3a) |
| CF₃ | C(O)NHCH₂(E-5a) |
| CF₃ | C(O)NHC(O)OCH₃ |
| CF₃ | C(O)N(CH₃)C(O)OCH₃ |
| CF₃ | C(O)N(Et)C(O)OCH₃ |
| CF₃ | C(O)N(CH₂CN)C(O)OCH₃ |
| CF₃ | C(O)N(CH₂OCH₃)C(O)OCH₃ |
| CF₃ | C(O)N[C(O)Et]C(O)OCH₃ |
| CF₃ | C(O)N[C(O)Pr-n]C(O)OCH₃ |
| CF₃ | C(O)N[C(O)Pr-i]C(O)OCH₃ |
| CF₃ | C(O)N[C(O)OCH₃]C(O)OCH₃ |
| CF₃ | C(O)NHC(O)OEt |
| CF₃ | C(O)N(CH₃)C(O)OEt |
| CF₃ | C(O)N(Et)C(O)OEt |
| CF₃ | C(O)N(CH₂CN)C(O)OEt |
| CF₃ | C(O)N(CH₂OCH₃)C(O)OEt |
| CF₃ | C(O)N[C(O)CH₃]C(O)OEt |
| CF₃ | C(O)N[C(O)Et]C(O)OEt |
| CF₃ | C(O)N[C(O)Pr-n]C(O)OEt |
| CF₃ | C(O)N[C(O)Pr-i]C(O)OEt |
| CF₃ | C(O)N[C(O)OCH₃]C(O)OEt |
| CF₃ | C(O)NHC(O)OPr-i |
| CF₃ | C(O)N(CH₃)C(O)OPr-i |
| CF₃ | C(O)N(Et)C(O)OPr-i |
| CF₃ | C(O)N(CH₂CN)C(O)OPr-i |
| CF₃ | C(O)N(CH₂OCH₃)C(O)OPr-i |
| CF₃ | C(O)N[C(O)CH₃]C(O)OPr-i |
| CF₃ | C(O)N[C(O)Et]C(O)OPr-i |
| CF₃ | C(O)N[C(O)Pr-n]C(O)OPr-i |
| CF₃ | C(O)N[C(O)Pr-i]C(O)OPr-i |
| CF₃ | C(O)N[C(O)OCH₃]C(O)OPr-i |
| CF₃ | C(O)N[C(O)OEt]C(O)OPr-i |
| CF₃ | C(O)NHC(O)NH₂ |
| CF₃ | C(O)NHN(CH₃)Ph |
| CF₃ | C(O)N[C(O)CH₃]N(CH₃)Ph |
| CF₃ | C(O)N[C(O)OCH₃]N(CH₃)Ph |
| CF₃ | C(O)NHN(CH₃)(D-45a) |
| CF₃ | C(O)N[C(O)CH₃]N(CH₃)(D-45a) |
| CF₃ | C(O)N[C(O)OCH₃]N(CH₃)(D-45a) |
| CF₃ | CH₂NH C(O)Pr-i |
| CF₃ | CH₂NH C(O)CF₃ |
| CF₃ | CH₂NH C(O)OEt |
| CF₃ | CH₂NH C(O)(Ph-2-CH₃) |
| CF₃ | CH₂NH C(O)NH(Ph-2-F) |
| CF₃ | CH₂N(CH₃)C(O)Me |
| CF₃ | CH₂N(i-Pr)C(O)Et |
| CF₃ | CH(CH₃)NHC(O) CHF₂ |
| CF₃ | CH₂(T-1) |
| F | CH₃ |
| F | Cl |
| F | Br |
| F | I |
| F | NO₂ |
| F | NH₂ |
| F | NHC(O)CH₃ |
| F | NHC(O)OCH₃ |
| F | NHC(O)OEt |
| F | OH |
| F | OC(O)CH₃ |
| F | OCH₂Ph |
| F | OSO₂CH₃ |
| F | OSO₂CF₃ |
| F | OSO₂Ph |
| F | OSO₂(Ph-4-CH₃) |
| F | SCH₃ |
| F | S(O)CH₃ |
| F | SO₂CH₃ |
| F | SEt |
| F | S(O)Et |
| F | SO₂Et |
| F | SCH₂CF₃ |
| F | SPh |
| F | SCH₂(D-42a) |
| F | D-38a |
| F | D-11a |
| F | D-21a |
| F | D-35a |
| F | D-36a-H |
| F | D-36a-Me |
| F | D-36b-Me |
| F | D-39a |
| F | D-40a-H |
| F | D-40a-Me |
| F | C(O)OH |
| F | C(O)OCH₃ |
| F | C(O)OEt |
| F | C(O)NH₂ |
| F | C(O)NHCH₂Pr-c |
| F | C(O)NHCH₂CF₃ |
| F | C(O)NHCH₂CH=CH₂ |
| F | C(O)NHCH₂CH=CH |
| F | C(O)NHCH₂CN |
| F | C(O)NHCH₂OCH₂CF₃ |
| F | C(O)NHCH₂CH₂OCH₃ |
| F | C(O)NHCH₂CH₂OEt |
| F | C(O)NHCH=NOCH₃ |
| F | C(O)NHCH=NOEt |
| F | C(O)NHCH₂CH=NOH |
| F | C(O)NHCH₂CH=NOCH₃ |
| F | C(O)NHCH₂C(O)OH |
| F | C(O)NHCH₂C(O)OCH₃ |
| F | C(O)NHCH₂C(O)NHCH₂CF₃ |
| F | C(O)NHCH(CH₃)C(O)OH |
| F | C(O)NHCH(CH₃)C(O)OCH₃ |
| F | C(O)NHCH(CH₃)C(O)NHCH₂CF₃ |
| F | C(O)NH(D-11a) |
| F | C(O)NH(D-42a) |
| F | C(O)NH(D-42d)Cl |
| F | C(O)NH(D-43e)Cl |
| F | C(O)NH(D-45a) |
| F | C(O)N[C(O)CH₃](D-45a) |
| F | C(O)N[C(O)OCH₃](D-45a) |
| F | C(O)NH(D-45c)Cl |
| F | C(O)N[C(O)CH₃](D-45c)Cl |
| F | C(O)N[C(O)OCH₃](D-45c)Cl |
| F | C(O)NH(D-46a) |
| F | C(O)NH(D-48a) |
| F | C(O)NH(E-1a) |
| F | C(O)NHCH₂(D-11a) |
| F | C(O)NHCH₂(D-14a)CH₃ |
| F | C(O)NHCH₂(D-14b)Cl |
| F | C(O)NHCH₂(D-18a) |
| F | C(O)NHCH₂(D-19a) |
| F | C(O)N[C(O)CH₃]CH₂(D-19a) |
| F | C(O)N[C(O)Et]CH₂(D-19a) |
| F | C(O)N[C(O)OCH₃]CH₂(D-19a) |
| F | C(O)NHCH₂(D-25a) |
| F | C(O)NHCH₂(D-27a) |
| F | C(O)NHCH₂(D-28a) |
| F | C(O)NHCH₂(D-31a) |
| F | C(O)NHCH₂(D-34a) |
| F | C(O)NHCH₂(D-36a) |
| F | C(O)NHCH₂(D-42a) |
| F | C(O)N(CH₃)CH₂(D-42a) |
| F | C(O)N(CH₂CN)CH₂(D-42a) |
| F | C(O)N(CH₂OCH₃)CH₂(D-42a) |
| F | C(O)N[C(O)CH₃]CH₂(D-42a) |
| F | C(O)N[C(O)Et]CH₂(D-42a) |
| F | C(O)N[C(O)OCH₃]CH₂(D-42a) |
| F | C(O)NHCH₂(D-44a) |
| F | C(O)NHCH₂(D-45a) |
| F | C(O)NHCH₂(D-46a) |
| F | C(O)NHCH₂(D-48a) |
| F | C(O)NHCH₂(E-1a) |
| F | C(O)NHCH₂(E-3a) |
| F | C(O)NHCH₂(E-5a) |
| F | C(O)NHC(O)OCH₃ |
| F | C(O)N(CH₃)C(O)OCH₃ |
| F | C(O)N(Et)C(O)OCH₃ |
| F | C(O)N(CH₂CN)C(O)OCH₃ |
| F | C(O)N(CH₂OCH₃)C(O)OCH₃ |
| F | C(O)N[C(O)Et]C(O)OCH₃ |
| F | C(O)N[C(O)Pr-n]C(O)OCH₃ |
| F | C(O)N[C(O)Pr-i]C(O)OCH₃ |
| F | C(O)N[C(O)OCH₃]C(O)OCH₃ |
| F | C(O)NHC(O)OEt |

TABLE 1-continued

| Y | R² |
|---|---|
| F | C(O)N(CH₃)C(O)OEt |
| F | C(O)N(Et)C(O)OEt |
| F | C(O)N(CH₂CN)C(O)OEt |
| F | C(O)N(CH₂OCH₃)C(O)OEt |
| F | C(O)N[C(O)CH₃]C(O)OEt |
| F | C(O)N[C(O)Et]C(O)OEt |
| F | C(O)N[C(O)Pr-n]C(O)OEt |
| F | C(O)N[C(O)Pr-i]C(O)OEt |
| F | C(O)N[C(O)OCH₃]C(O)OEt |
| F | C(O)NHC(O)OPr-i |
| F | C(O)N(CH₃)C(O)OPr-i |
| F | C(O)N(Et)C(O)OPr-i |
| F | C(O)N(CH₂CN)C(O)OPr-i |
| F | C(O)N(CH₂OCH₃)C(O)OPr-i |
| F | C(O)N[C(O)CH₃]C(O)OPr-i |
| F | C(O)N[C(O)Et]C(O)OPr-i |
| F | C(O)N[C(O)Pr-n]C(O)OPr-i |
| F | C(O)N[C(O)Pr-i]C(O)OPr-i |
| F | C(O)N[C(O)OCH₃]C(O)OPr-i |
| F | C(O)N[C(O)OEt]C(O)OPr-i |
| F | C(O)NHN(CH₃)Ph |
| F | C(O)N[C(O)CH₃]N(CH₃)Ph |
| F | C(O)N[C(O)OCH₃]N(CH₃)Ph |
| F | C(O)NHN(CH₃)(D-45a) |
| F | C(O)N[C(O)CH₃]N(CH₃)(D-45a) |
| F | C(O)N[C(O)OCH₃]N(CH₃)(D-45a) |
| F | CH₂NH C(O)Pr-i |
| F | CH₂NH C(O)CF₃ |
| F | CH₂NH C(O)OEt |
| F | CH₂NH C(O)(Ph-2-CH₃) |
| F | CH₂NH C(O)NH(Ph-2-F) |
| F | CH₂N(CH₃)C(O)Me |
| F | CH₂N(i-Pr)(C(O)Et |
| F | CH(CH₃)NHC(O) CHF₂ |
| F | CH₂(T-1) |
| Cl | CH₃ |
| Cl | F |
| Cl | Br |
| Cl | I |
| Cl | NO₂ |
| Cl | NH₂ |
| Cl | NHC(O)CH₃ |
| Cl | NHC(O)OCH₃ |
| Cl | NHC(O)OEt |
| Cl | OH |
| Cl | OC(O)CH₃ |
| Cl | OCH₂Ph |
| Cl | OSO₂CH₃ |
| Cl | OSO₂CF₃ |
| Cl | OSO₂Ph |
| Cl | OSO₂(Ph-4-CH₃) |
| Cl | SCH₃ |
| Cl | S(O)CH₃ |
| Cl | SO₂CH₃ |
| Cl | SEt |
| Cl | S(O)Et |
| Cl | SO₂Et |
| Cl | SCH₂CF₃ |
| Cl | SPh |
| Cl | SCH₂(D-42a) |
| Cl | D-38a |
| Cl | D-11a |
| Cl | D-21a |
| Cl | D-35a |
| Cl | D-36a-H |
| Cl | D-36a-Me |
| Cl | D-36b-Me |
| Cl | D-39a |
| Cl | D-40a-H |
| Cl | D-40a-Me |
| Cl | C(O)OH |
| Cl | C(O)OCH₃ |
| Cl | C(O)OEt |
| Cl | C(O)NH₂ |
| Cl | C(O)NHCH₂Pr-c |
| Cl | C(O)NHCH₂CF₃ |
| Cl | C(O)N(CH₂OCH₃)CH₂CF₃ |
| Cl | C(O)N[C(O)CH₃]CH₂CF₃ |

TABLE 1-continued

| Y | R² |
|---|---|
| Cl | C(O)N[C(O)OCH₃]CH₂CF₃ |
| Cl | C(O)NHCH₂CH═CH₂ |
| Cl | C(O)NHCH₂CH═CH |
| Cl | C(O)NHCH₂CN |
| Cl | C(O)NHCH₂OCH₂CF₃ |
| Cl | C(O)NHCH₂CH₂OCH₃ |
| Cl | C(O)NHCH₂CH₂OEt |
| Cl | C(O)NHCH═NOCH₃ |
| Cl | C(O)NHCH═NOEt |
| Cl | C(O)NHCH₂CH═NOH |
| Cl | C(O)NHCH₂CH═NOCH₃ |
| Cl | C(O)NHCH₂C(O)OH |
| Cl | C(O)NHCH₂C(O)OCH₃ |
| Cl | C(O)NHCH₂C(O)NH₂ |
| Cl | C(O)NHCH₂C(O)NHCH₂CH₂Cl |
| Cl | C(O)NHCH₂C(O)NHCH₂CH₂Br |
| Cl | C(O)NHCH₂C(O)NHCH₂CF₃ |
| Cl | C(O)NHCH₂C(O)NHCH₂CH₂OH |
| Cl | C(O)NHCH(CH₃)C(O)OH |
| Cl | C(O)NHCH(CH₃)C(O)OCH₃ |
| Cl | C(O)NHCH(CH₃)C(O)NHCH₂CH₂Cl |
| Cl | C(O)NHCH(CH₃)C(O)NHCH₂CF₃ |
| Cl | C(O)NH(D-11a) |
| Cl | C(O)NH(D-42a) |
| Cl | C(O)NH(D-42d)Cl |
| Cl | C(O)NH(D-43e)Cl |
| Cl | C(O)NH(D-45a) |
| Cl | C(O)N(CH₃)(D-45a) |
| Cl | C(O)N[C(O)CH₃](D-45a) |
| Cl | C(O)N[C(O)OCH₃](D-45a) |
| Cl | C(O)NH(D-45c)Cl |
| Cl | C(O)N(CH₃)(D-45c)Cl |
| Cl | C(O)N[C(O)CH₃](D-45c)Cl |
| Cl | C(O)N[C(O)OCH₃](D-45c)Cl |
| Cl | C(O)NH(D-46a) |
| Cl | C(O)NH(D-48a) |
| Cl | C(O)NH(E-1a) |
| Cl | C(O)NHCH₂(D-11a) |
| Cl | C(O)NHCH₂(D-14a)CH₃ |
| Cl | C(O)NHCH₂(D-14b)Cl |
| Cl | C(O)NHCH₂(D-18a) |
| Cl | C(O)NHCH₂(D-19a) |
| Cl | C(O)N[C(O)CH₃]CH₂(D-19a) |
| Cl | C(O)N[C(O)Et]CH₂(D-19a) |
| Cl | C(O)N[C(O)OCH₃]CH₂(D-19a) |
| Cl | C(O)NHCH₂(D-25a) |
| Cl | C(O)NHCH₂(D-27a) |
| Cl | C(O)NHCH₂(D-28a) |
| Cl | C(O)NHCH₂(D-31a) |
| Cl | C(O)NHCH₂(D-34a) |
| Cl | C(O)NHCH₂(D-36a) |
| Cl | C(O)NHCH₂(D-42a) |
| Cl | C(O)N(CH₂CN)CH₂(D-42a) |
| Cl | C(O)N(CH₂OCH₃)CH₂(D-42a) |
| Cl | C(O)N[C(O)CH₃]CH₂(D-42a) |
| Cl | C(O)N[C(O)Et]CH₂(D-42a) |
| Cl | C(O)N[C(O)OCH₃]CH₂(D-42a) |
| Cl | C(O)NHCH₂(D-44a) |
| Cl | C(O)NHCH₂(D-45a) |
| Cl | C(O)NHCH₂(D-46a) |
| Cl | C(O)NHCH₂(D-48a) |
| Cl | C(O)NHCH₂(E-1a) |
| Cl | C(O)NHCH₂(E-3a) |
| Cl | C(O)NHCH₂(E-5a) |
| Cl | C(O)NHC(O)OCH₃ |
| Cl | C(O)N(CH₃)C(O)OCH₃ |
| Cl | C(O)N(Et)C(O)OCH₃ |
| Cl | C(O)N(CH₂CN)C(O)OCH₃ |
| Cl | C(O)N(CH₂OCH₃)C(O)OCH₃ |
| Cl | C(O)N[C(O)Et]C(O)OCH₃ |
| Cl | C(O)N[C(O)Pr-n]C(O)OCH₃ |
| Cl | C(O)N[C(O)Pr-i]C(O)OCH₃ |
| Cl | C(O)N[C(O)OCH₃]C(O)OCH₃ |
| Cl | C(O)NHC(O)OEt |
| Cl | C(O)N(CH₃)C(O)OEt |
| Cl | C(O)N(Et)C(O)OEt |
| Cl | C(O)N(CH₂CN)C(O)OEt |
| Cl | C(O)N(CH₂OCH₃)C(O)OEt |

TABLE 1-continued

| Y | R² |
|---|---|
| Cl | C(O)N[C(O)CH₃]C(O)OEt |
| Cl | C(O)N[C(O)Et]C(O)OEt |
| Cl | C(O)N[C(O)Pr-n]C(O)OEt |
| Cl | C(O)N[C(O)Pr-i]C(O)OEt |
| Cl | C(O)N[C(O)OCH₃]C(O)OEt |
| Cl | C(O)NHC(O)OPr-i |
| Cl | C(O)N(CH₃)C(O)OPr-i |
| Cl | C(O)N(Et)C(O)OPr-i |
| Cl | C(O)N(CH₂CN)C(O)OPr-i |
| Cl | C(O)N(CH₂OCH₃)C(O)OPr-i |
| Cl | C(O)N[C(O)CH₃]C(O)OPr-i |
| Cl | C(O)N[C(O)Et]C(O)OPr-i |
| Cl | C(O)N[C(O)Pr-n]C(O)OPr-i |
| Cl | C(O)N[C(O)Pr-i]C(O)OPr-i |
| Cl | C(O)N[C(O)OCH₃]C(O)OPr-i |
| Cl | C(O)N[C(O)OEt]C(O)OPr-i |
| Cl | C(O)NHC(O)NH₂ |
| Cl | C(O)NHN(CH₃)Ph |
| Cl | C(O)N[C(O)CH₃]N(CH₃)Ph |
| Cl | C(O)N[C(O)OCH₃]N(CH₃)Ph |
| Cl | C(O)NHN(CH₃)(D-45a) |
| Cl | C(O)N[C(O)CH₃]N(CH₃)(D-45a) |
| Cl | C(O)N[C(O)OCH₃]N(CH₃)(D-45a) |
| Cl | CH₂NH C(O)Pr-i |
| Cl | CH₂NH C(O)CF₃ |
| Cl | CH₂NH C(O)OEt |
| Cl | CH₂NH C(O)(Ph-2-CH₃) |
| Cl | CH₂NH C(O)NH(Ph-2-F) |
| Cl | CH₂N(CH₃)C(O)Me |
| Cl | CH₂N(i-Pr)C(O)Et |
| Cl | CH(CH₃)NHC(O) CHF₂ |
| Cl | CH₂(T-1) |
| Br | CH₃ |
| Br | F |
| Br | I |
| Br | NO₂ |
| Br | NH₂ |
| Br | NHC(O)CH₃ |
| Br | NHC(O)OCH₃ |
| Br | NHC(O)OEt |
| Br | OH |
| Br | OC(O)CH₃ |
| Br | OCH₂Ph |
| Br | OSO₂CH₃ |
| Br | OSO₂CF₃ |
| Br | OSO₂Ph |
| Br | OSO₂(Ph-4-CH₃) |
| Br | SCH₃ |
| Br | S(O)CH₃ |
| Br | SO₂CH₃ |
| Br | SEt |
| Br | S(O)Et |
| Br | SO₂Et |
| Br | SCH₂CF₃ |
| Br | SPh |
| Br | SCH₂(D-42a) |
| Br | D-38a |
| Br | D-11a |
| Br | D-21a |
| Br | D-35a |
| Br | D-36a-H |
| Br | D-36a-Me |
| Br | D-36b-Me |
| Br | D-39a |
| Br | D-40a-H |
| Br | D-40a-Me |
| Br | C(O)OH |
| Br | C(O)OCH₃ |
| Br | C(O)OEt |
| Br | C(O)NH₂ |
| Br | C(O)NHCH₂Pr-c |
| Br | C(O)NHCH₂CF₃ |
| Br | C(O)N(CH₃)CH₂CF₃ |
| Br | C(O)N[C(O)CH₃]CH₂CF₃ |
| Br | C(O)N[C(O)OCH₃]CH₂CF₃ |
| Br | C(O)NHCH₂CH=CH₂ |
| Br | C(O)NHCH₂CH=CH |
| Br | C(O)NHCH₂CN |
| Br | C(O)NHCH₂OCH₂CF₃ |
| Br | C(O)NHCH₂CH₂OCH₃ |
| Br | C(O)NHCH₂CH₂OEt |
| Br | C(O)NHCH=NOCH₃ |
| Br | C(O)NHCH=NOEt |
| Br | C(O)NHCH₂CH=NOH |
| Br | C(O)NHCH₂CH=NOCH₃ |
| Br | C(O)NHCH₂C(O)OH |
| Br | C(O)NHCH₂C(O)OCH₃ |
| Br | C(O)NHCH₂C(O)NH₂ |
| Br | C(O)NHCH₂C(O)NHCH₂CF₃ |
| Br | C(O)NHCH₂C(O)NHCH₂CH₂OH |
| Br | C(O)NHCH(CH₃)C(O)OH |
| Br | C(O)NHCH(CH₃)C(O)OCH₃ |
| Br | C(O)NHCH(CH₃)C(O)NHCH₂CF₃ |
| Br | C(O)NH(D-11a) |
| Br | C(O)NH(D-42a) |
| Br | C(O)NH(D-42d)Cl |
| Br | C(O)NH(D-43e)Cl |
| Br | C(O)NH(D-45a) |
| Br | C(O)N(CH₃)(D-45a) |
| Br | C(O)N[C(O)CH₃](D-45a) |
| Br | C(O)N[C(O)OCH₃](D-45a) |
| Br | C(O)NH(D-45c)Cl |
| Br | C(O)N(CH₃)(D-45c)Cl |
| Br | C(O)N[C(O)CH₃](D-45c)Cl |
| Br | C(O)N[C(O)OCH₃](D-45c)Cl |
| Br | C(O)NH(D-46a) |
| Br | C(O)NH(D-48a) |
| Br | C(O)NH(E-1a) |
| Br | C(O)NHCH₂(D-11a) |
| Br | C(O)NHCH₂(D-14a)CH₃ |
| Br | C(O)NHCH₂(D-14b)Cl |
| Br | C(O)NHCH₂(D-18a) |
| Br | C(O)NHCH₂(D-19a) |
| Br | C(O)N[C(O)CH₃]CH₂(D-19a) |
| Br | C(O)N[C(O)Et]CH₂(D-19a) |
| Br | C(O)N[C(O)OCH₃]CH₂(D-19a) |
| Br | C(O)NHCH₂(D-25a) |
| Br | C(O)NHCH₂(D-27a) |
| Br | C(O)NHCH₂(D-28a) |
| Br | C(O)NHCH₂(D-31a) |
| Br | C(O)NHCH₂(D-34a) |
| Br | C(O)NHCH₂(D-36a) |
| Br | C(O)NHCH₂(D-42a) |
| Br | C(O)N(CH₂CN)CH₂(D-42a) |
| Br | C(O)N(CH₂OCH₃)CH₂(D-42a) |
| Br | C(O)N[C(O)CH₃]CH₂ D-42a) |
| Br | C(O)N[C(O)Et]CH₂(D-42a) |
| Br | C(O)N[C(O)OCH₃]CH₂(D-42a) |
| Br | C(O)NHCH₂(D-44a) |
| Br | C(O)NHCH₂(D-45a) |
| Br | C(O)NHCH₂(D-46a) |
| Br | C(O)NHCH₂(D-48a) |
| Br | C(O)NHCH₂(E-1a) |
| Br | C(O)NHCH₂(E-3a) |
| Br | C(O)NHCH₂(E-5a) |
| Br | C(O)NHC(O)OCH₃ |
| Br | C(O)N(CH₃)C(O)OCH₃ |
| Br | C(O)N(Et)C(O)OCH₃ |
| Br | C(O)N(CH₂CN)C(O)OCH₃ |
| Br | C(O)N(CH₂OCH₃)C(O)OCH₃ |
| Br | C(O)N[C(O)Et]C(O)OCH₃ |
| Br | C(O)N[C(O)Pr-n]C(O)OCH₃ |
| Br | C(O)N[C(O)Pr-i]C(O)OCH₃ |
| Br | C(O)N[C(O)OCH₃]C(O)OCH₃ |
| Br | C(O)NHC(O)OEt |
| Br | C(O)N(CH₃)C(O)OEt |
| Br | C(O)N(Et)C(O)OEt |
| Br | C(O)N(CH₂CN)C(O)OEt |
| Br | C(O)N(CH₂OCH₃)C(O)OEt |
| Br | C(O)N[C(O)CH₃]C(O)OEt |
| Br | C(O)N[C(O)Et]C(O)OEt |
| Br | C(O)N[C(O)Pr-n]C(O)OEt |
| Br | C(O)N[C(O)Pr-i]C(O)OEt |
| Br | C(O)N[C(O)OCH₃]C(O)OEt |
| Br | C(O)NHC(O)OPr-i |
| Br | C(O)N(CH₃)C(O)OPr-i |

TABLE 1-continued

| Y | R² |
|---|---|
| Br | C(O)N(Et)C(O)OPr-i |
| Br | C(O)N(CH₂CN)C(O)OPr-i |
| Br | C(O)N(CH₂OCH₃)C(O)OPr-i |
| Br | C(O)N[C(O)CH₃]C(O)OPr-i |
| Br | C(O)N[C(O)Et]C(O)OPr-i |
| Br | C(O)N[C(O)Pr-n]C(O)OPr-i |
| Br | C(O)N[C(O)Pr-i]C(O)OPr-i |
| Br | C(O)N[C(O)OCH₃]C(O)OPr-i |
| Br | C(O)N[C(O)OEt]C(O)OPr-i |
| Br | C(O)NHC(O)NH₂ |
| Br | C(O)NHN(CH₃)Ph |
| Br | C(O)N[C(O)CH₃]N(CH₃)Ph |
| Br | C(O)N[C(O)OCH₃]N(CH₃)Ph |
| Br | C(O)NHN(CH₃)(D-45a) |
| Br | C(O)N[C(O)CH₃]N(CH₃)(D-45a) |
| Br | C(O)N[C(O)OCH₃]N(CH₃)(D-45a) |
| Br | CH₂NH C(O)Pr-i |
| Br | CH₂NH C(O)CF₃ |
| Br | CH₂NH C(O)OEt |
| Br | CH₂NH C(O)(Ph-2-CH₃) |
| Br | CH₂NH C(O)NH(Ph-2-F) |
| Br | CH₂N(CH₃)C(O)Me |
| Br | CH₂N(i-Pr)C(O)Et |
| Br | CH(CH₃)NHC(O) CHF₂ |
| Br | CH₂(T-1) |
| I | CH₃ |
| I | NO₂ |
| I | NH₂ |
| I | NHC(O)CH₃ |
| I | NHC(O)OCH₃ |
| I | NHC(O)OEt |
| I | OH |
| I | OC(O)CH₃ |
| I | OCH₂Ph |
| I | OSO₂CF₃ |
| I | SCH₃ |
| I | S(O)CH₃ |
| I | SO₂CH₃ |
| I | SEt |
| I | S(O)Et |
| I | SO₂Et |
| I | SCH₂CF₃ |
| I | SPh |
| I | SCH₂(D-42a) |
| I | D-38a |
| I | D-11a |
| I | D-21a |
| I | D-35 |
| I | D-36a-H |
| I | D-36a-Me |
| I | D-36b-Me |
| I | D-39a |
| I | D-40a-H |
| I | D-40a-Me |
| I | C(O)OH |
| I | C(O)OCH₃ |
| I | C(O)OEt |
| I | C(O)NH₂ |
| I | C(O)NHCH₂Pr-c |
| I | C(O)NHCH₂CF₃ |
| I | C(O)NHCH₂CH=CH₂ |
| I | C(O)NHCH₂CH=CH |
| I | C(O)NHCH₂CN |
| I | C(O)NHCH₂OCH₂CF₃ |
| I | C(O)NHCH₂OCH₃ |
| I | C(O)NHCH₂CH₂OEt |
| I | C(O)NHCH=NOCH₃ |
| I | C(O)NHCH=NOEt |
| I | C(O)NHCH₂CH=NOH |
| I | C(O)NHCH₂CH=NOCH₃ |
| I | C(O)NHCH₂C(O)OH |
| I | C(O)NHCH₂C(O)OCH₃ |
| I | C(O)NHCH₂C(O)NHCH₂CF₃ |
| I | C(O)NHCH(CH₃)C(O)OH |
| I | C(O)NHCH(CH₃)C(O)OCH₃ |
| I | C(O)NHCH(CH₃)C(O)NHCH₂CF₃ |
| I | C(O)NH(D-11a) |
| I | C(O)NH(D-42a) |
| I | C(O)NH(D-42d)Cl |
| I | C(O)NH(D-43e)Cl |
| I | C(O)NH(D-45a) |
| I | C(O)N[C(O)CH₃](D-45a) |
| I | C(O)N[C(O)OCH₃](D-45a) |
| I | C(O)NH(D-45c)Cl |
| I | C(O)N[C(O)CH₃](D-45c)Cl |
| I | C(O)N[C(O)OCH₃](D-45c)Cl |
| I | C(O)NH(D-46a) |
| I | C(O)NH(D-48a) |
| I | C(O)NH(E-1a) |
| I | C(O)NHCH₂(D-11a) |
| I | C(O)NHCH₂(D-14a)CH₃ |
| I | C(O)NHCH₂(D-14b)Cl |
| I | C(O)NHCH₂(D-18a) |
| I | C(O)NHCH₂(D-19a) |
| I | C(O)N[C(O)CH₃]CH₂(D-19a) |
| I | C(O)N[C(O)Et]CH₂(D-19a) |
| I | C(O)N[C(O)OCH₃]CH₂(D-19a) |
| I | C(O)NHCH₂(D-25a) |
| I | C(O)NHCH₂(D-27a) |
| I | C(O)NHCH₂(D-28a) |
| I | C(O)NHCH₂(D-31a) |
| I | C(O)NHCH₂(D-34a) |
| I | C(O)NHCH₂(D-36a) |
| I | C(O)NHCH₂(D-42a) |
| I | C(O)N(CH₂CN)CH₂(D-42a) |
| I | C(O)N(CH₂OCH₃)CH₂(D-42a) |
| I | C(O)N[C(O)CH₃]CH₂(D-42a) |
| I | C(O)N[C(O)Et]CH₂(D-42a) |
| I | C(O)N[C(O)OCH₃]CH₂(D-42a) |
| I | C(O)NHCH₂(D-44a) |
| I | C(O)NHCH₂(D-45a) |
| I | C(O)NHCH₂(D-46a) |
| I | C(O)NHCH₂(D-48a) |
| I | C(O)NHCH₂(E-1a) |
| I | C(O)NHCH₂(E-3a) |
| I | C(O)NHCH₂(E-5a) |
| I | C(O)NHC(O)OCH₃ |
| I | C(O)N(CH₃)C(O)OCH₃ |
| I | C(O)N(Et)C(O)OCH₃ |
| I | C(O)N(CH₂CN)C(O)OCH₃ |
| I | C(O)N(CH₂OCH₃)C(O)OCH₃ |
| I | C(O)N[C(O)Et]C(O)OCH₃ |
| I | C(O)N[C(O)Pr-n]C(O)OCH₃ |
| I | C(O)N[C(O)Pr-i]C(O)OCH₃ |
| I | C(O)N[C(O)OCH₃]C(O)OCH₃ |
| I | C(O)NHC(O)OEt |
| I | C(O)N(CH₃)C(O)OEt |
| I | C(O)N(Et)C(O)OEt |
| I | C(O)N(CH₂CN)C(O)OEt |
| I | C(O)N(CH₂OCH₃)C(O)OEt |
| I | C(O)N[C(O)CH₃]C(O)OEt |
| I | C(O)N[C(O)Et]C(O)OEt |
| I | C(O)N[C(O)Pr-n]C(O)OEt |
| I | C(O)N[C(O)Pr-i]C(O)OEt |
| I | C(O)N[C(O)OCH₃]C(O)OEt |
| I | C(O)NHC(O)OPr-i |
| I | C(O)N(CH₃)C(O)OPr-i |
| I | C(O)N(Et)C(O)OPr-i |
| I | C(O)N(CH₂CN)C(O)OPr-i |
| I | C(O)N(CH₂OCH₃)C(O)OPr-i |
| I | C(O)N[C(O)CH₃]C(O)OPr-i |
| I | C(O)N[C(O)Et]C(O)OPr-i |
| I | C(O)N[C(O)Pr-n]C(O)OPr-i |
| I | C(O)N[C(O)Pr-i]C(O)OPr-i |
| I | C(O)N[C(O)OCH₃]C(O)OPr-i |
| I | C(O)N[C(O)OEt]C(O)OPr-i |
| I | C(O)NHC(O)NH₂ |
| I | C(O)NHN(CH₃)Ph |
| I | C(O)N[C(O)CH₃]N(CH₃)Ph |
| I | C(O)N[C(O)OCH₃]N(CH₃)Ph |
| I | C(O)NHN(CH₃)(D-45a) |
| I | C(O)N[C(O)CH₃]N(CH₃)(D-45a) |
| I | C(O)N[C(O)OCH₃]N(CH₃)(D-45a) |
| I | CH₂NH C(O)Pr-i |
| I | CH₂NH C(O)CF₃ |
| I | CH₂NH C(O)OEt |

TABLE 1-continued

| Y | R² |
|---|---|
| I | CH₂NH C(O)(Ph-2-CH₃) |
| I | CH₂NH C(O)NH(Ph-2-F) |
| I | CH₂N(CH₃)C(O)Me |
| I | CH₂N(i-Pr)C(O)Et |
| I | CH(CH₃)NHC(O) CHF₂ |
| I | CH₂(T-1) |
| CN | F |
| CN | Cl |
| CN | Br |
| CN | I |
| CN | NO₂ |
| CN | NH₂ |
| CN | NHC(O)CH₃ |
| CN | NHC(O)OCH₃ |
| CN | NHC(O)OEt |
| CN | OH |
| CN | OC(O)CH₃ |
| CN | OCH₂Ph |
| CN | OSO₂CH₃ |
| CN | OSO₂CF₃ |
| CN | OSO₂Ph |
| CN | OSO₂(Ph-4-CH₃) |
| CN | SCH₃ |
| CN | S(O)CH₃ |
| CN | SO₂CH₃ |
| CN | SEt |
| CN | S(O)Et |
| CN | SO₂Et |
| CN | SCH₂CF₃ |
| CN | SPh |
| CN | SCH₂(D-42a) |
| CN | D-38a |
| CN | D-11a |
| CN | D-21a |
| CN | D-35a |
| CN | D-36a-H |
| CN | D-36a-Me |
| CN | D-36b-Me |
| CN | D-39a |
| CN | D-40a-H |
| CN | D-40a-Me |
| CN | C(O)OH |
| CN | C(O)OCH₃ |
| CN | C(O)OEt |
| CN | C(O)NH₂ |
| CN | C(O)NHCH₂Pr-c |
| CN | C(O)NHCH₂CF₃ |
| CN | C(O)NHCH₂CH=CH₂ |
| CN | C(O)NHCH₂CH≡CH |
| CN | C(O)NHCH₂CN |
| CN | C(O)NHCH₂OCH₂CF₃ |
| CN | C(O)NHCH₂CH₂OCH₃ |
| CN | C(O)NHCH₂CH₂OEt |
| CN | C(O)NHCH=NOCH₃ |
| CN | C(O)NHCH=NOEt |
| CN | C(O)NHCH₂CH=NOH |
| CN | C(O)NHCH₂CH=NOCH₃ |
| CN | C(O)NHCH₂C(O)OH |
| CN | C(O)NHCH₂C(O)OCH₃ |
| CN | C(O)NHCH₂C(O)OEt |
| CN | C(O)NHCH₂C(O)NH₂ |
| CN | C(O)NHCH₂C(O)NHCH₂CF₃ |
| CN | C(O)NHCH(CH₃)C(O)OH |
| CN | C(O)NHCH(CH₃)C(O)OCH₃ |
| CN | C(O)NHCH(CH₃)C(O)NHCH₂CF₃ |
| CN | C(O)NH(D-11a) |
| CN | C(O)NH(D-42a) |
| CN | C(O)NH(D-42d)Cl |
| CN | C(O)NH(D-43e)Cl |
| CN | C(O)NH(D-45a) |
| CN | C(O)N[C(O)CH₃](D-45a) |
| CN | C(O)N[C(O)OCH₃](D-45a) |
| CN | C(O)NH(D-45c)Cl |
| CN | C(O)N[C(O)CH₃](D-45c)Cl |
| CN | C(O)N[C(O)OCH₃](D-45c)Cl |
| CN | C(O)NH(D-46a) |
| CN | C(O)NH(D-48a) |
| CN | C(O)NH(E-1a) |
| CN | C(O)NHCH₂(D-11a) |
| CN | C(O)NHCH₂(D-14a)CH₃ |
| CN | C(O)NHCH₂(D-14b)Cl |
| CN | C(O)NHCH₂(D-18a) |
| CN | C(O)NHCH₂(D-19a) |
| CN | C(O)N[C(O)CH₃]CH₂(D-19a) |
| CN | C(O)N[C(O)Et]CH₂(D-19a) |
| CN | C(O)N[C(O)OCH₃]CH₂(D-19a) |
| CN | C(O)NHCH₂(D-25a) |
| CN | C(O)NHCH₂(D-27a) |
| CN | C(O)NHCH₂(D-28a) |
| CN | C(O)NHCH₂(D-31a) |
| CN | C(O)NHCH₂(D-34a) |
| CN | C(O)NHCH₂(D-36a) |
| CN | C(O)NHCH₂(D-42a) |
| CN | C(O)N(CH₂OCH₃)CH₂(D-42a) |
| CN | C(O)N[C(O)CH₃]CH₂(D-42a) |
| CN | C(O)N[C(O)Et]CH₂(D-42a) |
| CN | C(O)N[C(O)OCH₃]CH₂(D-42a) |
| CN | C(O)NHCH₂(D-44a) |
| CN | C(O)NHCH₂(D-45a) |
| CN | C(O)NHCH₂(D-46a) |
| CN | C(O)NHCH₂(D-48a) |
| CN | C(O)NHCH₂(E-1a) |
| CN | C(O)NHCH₂(E-3a) |
| CN | C(O)NHCH₂(E-5a) |
| CN | C(O)NHC(O)OCH₃ |
| CN | C(O)N(CH₃)C(O)OCH₃ |
| CN | C(O)N(Et)C(O)OCH₃ |
| CN | C(O)N(CH₂OCH₃)C(O)OCH₃ |
| CN | C(O)N[C(O)Et]C(O)OCH₃ |
| CN | C(O)N[C(O)Pr-n]C(O)OCH₃ |
| CN | C(O)N[C(O)Pr-i]C(O)OCH₃ |
| CN | C(O)N[C(O)OCH₃]C(O)OCH₃ |
| CN | C(O)NHC(O)OEt |
| CN | C(O)N(CH₃)C(O)OEt |
| CN | C(O)N(Et)C(O)OEt |
| CN | C(O)N(CH₂OCH₃)C(O)OEt |
| CN | C(O)N[C(O)CH₃]C(O)OEt |
| CN | C(O)N[C(O)Et]C(O)OEt |
| CN | C(O)N[C(O)Pr-n]C(O)OEt |
| CN | C(O)N[C(O)Pr-i]C(O)OEt |
| CN | C(O)N[C(O)OCH₃]C(O)OEt |
| CN | C(O)NHC(O)OPr-i |
| CN | C(O)N(CH₃)C(O)OPr-i |
| CN | C(O)N(Et)C(O)OPr-i |
| CN | C(O)N(CH₂OCH₃)C(O)OPr-i |
| CN | C(O)N[C(O)CH₃]C(O)OPr-i |
| CN | C(O)N[C(O)Et]C(O)OPr-i |
| CN | C(O)N[C(O)Pr-n]C(O)OPr-i |
| CN | C(O)N[C(O)Pr-i]C(O)OPr-i |
| CN | C(O)N[C(O)OCH₃]C(O)OPr-i |
| CN | C(O)N[C(O)OEt]C(O)OPr-i |
| CN | C(O)NHC(O)NH₂ |
| CN | C(O)NHN(CH₃)Ph |
| CN | C(O)N[C(O)CH₃]N(CH₃)Ph |
| CN | C(O)N[C(O)OCH₃]N(CH₃)Ph |
| CN | C(O)NHN(CH₃)(D-45a) |
| CN | C(O)N[C(O)CH₃]N(CH₃)(D-45a) |
| CN | C(O)N[C(O)OCH₃]N(CH₃)(D-45a) |
| CN | CH₂NH C(O)Pr-i |
| CN | CH₂NH C(O)CF₃ |
| CN | CH₂NH C(O)OEt |
| CN | CH₂NH C(O)(Ph-2-CH₃) |
| CN | CH₂NH C(O)NH(Ph-2-F) |
| CN | CH₂N(CH₃)C(O)Me |
| CN | CH₂N(i-Pr)C(O)Et |
| CN | CH(CH₃)NHC(O) CHF₂ |
| CN | CH₂(T-1) |

Specific examples of α,β-unsaturated carbonyl compounds represented by Formula (2) include, besides the above described compounds, 3-penten-2-one, phorone, isophorone, diisopropylidene acetone, benzalacetone, 4-(2-furyl)-3-buten-2-one, 1,3-diphenyl-2-propen-1-one, 1-phenyl-3-(3-nitrophenyl)-2-propen-1-one, 1-(3-chlorophenyl)-3-(4-nitrophenyl)-2-propen-1-one, 1-phenyl-3-(p-biphenyl)-2- propen-1-one, 1-(naphthalen-2-yl)-3-phenyl-2-propen-1-one, 3-(4-(methylsulfonyl)phenyl)-1-phenyl-2-propen-1-one, 4-(3-oxo-3-phenyl-1-propen-1-yl) benzonitrile, 1-(3-fluorophenyl)-3-(furan-2-yl)-2-propen-1-one and methyl 4-(3-oxo-3-phenyl-1-propen-1-yl) benzoate.

EXAMPLES

Examples according to the present invention will be shown below. However, the present invention is not limited to these examples.

Synthesis Example

Synthesis Example of Raw Material 1

Synthesis of 3',5'-dichloro-2,2,2-trifluoroacetophenone

Step 1: Synthesis of methyl 3,5-dichlorobenzoate 10 g of concentrated sulfuric acid was added to a methanol (120 g) solution of 50 g of 3,5-dichlorobenzoic acid, and the mixture was refluxed by heating for 5 hours. After cooling the reaction solution to room temperature, the solvent was distilled off under reduced pressure. The obtained residue was dissolved into 200 g of ethyl acetate, washed with water (200 g×2), then washed with a saturated aqueous solution of sodium bicarbonate, and further washed with water. After drying the organic phase over anhydrous magnesium sulfate, 48.6 g of the target product was obtained as a white solid by removing the solvent by distilling under reduced pressure.

$^1$H-NMR (CDCl$_3$, Me$_4$Si, 300 MHz) δ 7.90 (s, 2H), 7.54 (s, 1H), 3.94 (s, 3H).

Step 2: Synthesis of 3',5'-dichloro-2,2,2-trifluoroacetophenone

After adding 0.37 g of cesium fluoride to dimethoxyethane (300 g) solution of 25 g of methyl 3,5-dichlorobenzoate and 22.5 g of trifluoromethyltrimethylsilane under ice cooling, the mixture was warmed to room temperature and stirred for 4 hours. After confirming disappearance of the raw materials, 200 g of water was added to the reaction solution, and the mixture was extracted with 200 g of ethyl acetate. After dehydration/drying of the organic phase with saturated saline and then over anhydrous magnesium sulfate in this order, the solvent was distilled off under reduced pressure to obtain 35.5 g of 1-(3,5-dichlorophenyl)-2,2,2-trifluoro-1-trimethylsilyloxy-1-methoxyethane as crude yellow liquid. The obtained crude product was dissolved into 100 ml of tetrahydrofuran, and 9.75 ml of 1 M tetrahydrofuran (100 ml) solution of tetrabutylammonium fluoride was added in dropwise at room temperature. The mixture was stirred for 2 hours at the same temperature. After completion of the reaction, the solvent was distilled off under reduced pressure and the obtained residue was dissolved into ethyl acetate. After washing the organic phase with water and drying over anhydrous magnesium sulfate, the solvent was distilled off under reduced pressure. 24.2 g of the target product as colorless liquid was obtained by purifying the obtained residue by distilling under reduced pressure.

Boiling point 87° C. (1.7 kPa) $^1$H-NMR (CDCl$_3$, Me$_4$Si, 300 MHz) δ 7.92-7.93 (m, 2H), 7.70-7.71 (m, 1H).

Synthesis Example of Raw Material 2

Synthesis of 4-acetyl-2-methylbenzoic Acid

Step 1: Synthesis of 4-acetyl-2-methylaniline 41.2 g (398 mmol) of 95% sulfuric acid was added in dropwise to a suspension solution of 38.1 g (199 mmol) of 4'-acetyl-2'-methylacetanilide and 267 g of water at room temperature. After adding in dropwise, the mixture was heated to 85° C. and stirred for 5 hours. After completion of the reaction, the sulfuric acid solution cooled to room temperature was analyzed by a quantitative analysis method using HPLC. A content of 4-acetyl-2-methylaniline was 27.0 g (yield 91%).

Step 2: Synthesis of 4'-bromo-3'-methylacetophenone 27.0 g of acetonitrile was added to a sulfuric acid solution of 27.0 g (181 mmol) of 4-acetyl-2-methylaniline, and the mixture was cooled to 0° C. An aqueous solution in which 13.1 g (190 mmol) of sodium nitrite was dissolved into 26.2 g of water was added in dropwise to the mixture. After reacting the resultant mixture for 1 hour at 0° C., an aqueous solution in which 1.1 g (18 mmol) of urea was dissolved into 2.2 g of water was added in dropwise, and the mixture was further stirred for 30 minutes to obtain an aqueous solution of 4-acetyl-2-methylbenzenediazonium sulfate. 5.18 g (36 mmol) of copper bromide, 62.2 g (362 mmol) of 47% hydrobromic acid and 81.0 g of acetonitrile were fed into another reactor. The aqueous solution of 4-acetyl-2-methylbenzenediazonium sulfate was added to this mixture in dropwise over 1 hour with stirring at 50° C. After adding in dropwise, the mixture was reacted for 1 hour at 50° C. Then, 81 g of toluene was added and the mixture was stirred for 30 minutes, and the water phase was separated. 54 g of toluene was added to the water phase and extracted again. The combined toluene solution was washed twice with 54 g of 14% aqueous ammonia and once with 54 g of water to obtain a toluene solution of 4'-bromo-3'-methylacetophenone. After removing the solvent by distilling under reduced pressure, the residue was distilled under reduced pressure of 1.5 kPa. 32.8 g of the obtained fraction which was collected in the range of outflow gas temperature from 130° C. to 137° C. was analyzed by HPLC. A percentage of relative area of 4'-bromo-3'-methylacetophenone was 99.1% (yield 84%).

Step 3: Synthesis of 4-acetyl-2-methylbenzoic Acid 63.9 g (300 mmol) of 4'-bromo-3'-methylacetophenone, 256 g of toluene, 32 g of water, 45.5 g (330 mmol) of potassium carbonate, 9.66 g (30 mmol) of tetra(n-butyl) ammonium bromide, 1.45 g (water content 55.95% by weight) of activated charcoal supported 5% palladium and 0.372 g (0.90 mmol) of 1,3-bis(diphenylphosphino)propane were fed into a pressure-tight reactor, and reaction was performed at 120° for 7 hours by pressurizing with carbon monoxide at 0.8 MPa. After cooling the reaction solution to room temperature, inside of the reactor was purged with nitrogen, and then the pressure was reduced to atmosphere pressure. 224 g of water was added, and stirred for 30 minutes. Catalyst was filtered with Celite and the organic phase was separated. 43.8 g (420 mmol) of 35% hydrochloric acid was added to the water phase. The obtained slurry was filtered, and then dried under reduced pressure to obtain 48.1 g of 4-acetyl-2-methylbenzoic acid as white crystal (yield 90%).

Synthesis Example of Raw Material 2-2

Synthesis of 4-acetyl-2-methylbenzoic Acid (2nd Method)

16.6 g (120 mmol) of potassium carbonate, 30.1 g (300 mmol) of n-butyl vinyl ether, 44.9 mg (0.2 mmol) of palladium acetate and 0.247 g (0.6 mmol) of 1,3-bis(diphenylphosphino)propane were added to a suspension solution of 21.5 g (100 mmol) of 4-bromo-2-methylbenzoic acid and 64.5 g of n-butanol. After degassing and nitrogen-purging inside of the reactor, the mixture was refluxed for 5 hours.

After cooling the reaction solution to 80° C., n-butanol and n-butyl vinyl ether were distilled off under reduced pressure. After adding 172 g of toluene and 108 g of water, the mixture was neutralized by adding 15.6 g (150 mmol) of concentrated hydrochloric acid, and the water phase was separated. The obtained toluene solution was analyzed by a quantitative analysis method using HPLC. A content of 4-acetyl-2-methylbenzoic acid was 16.9 g (yield 95%).

Synthesis Example of Raw Material 3

Synthesis of 4-acetyl-2-methylbenzoic Acid Amide

Step 1: Synthesis of 4-acetyl-2-methylbenzyl Chloride 28 ml of dichloromethane, 4 ml of oxalyl chloride, and a drop of N,N-dimethylformamide were added to 5.0 g of 4-acetyl-2-methylbenzoic acid, and the mixture was stirred for 3 hours at room temperature. After removing the solvent by distilling under reduced pressure, 5.6 g of crude 4-acetyl-2-methylbenzyl chloride was obtained.

$^1$H-NMR (CDCl$_3$, Me$_4$Si, 400 MHz) δ 8.26 (d, J=8.2 Hz, 1H), 7.82-7.91 (m, 2H), 2.65 (s, 3H), 2.63 (s, 3H).

Step 2: Synthesis of 4-acetyl-2-methylbenzoic Acid Amide 21 ml of dichloromethane was added to 2 g of concentrated aqueous ammonia, and the mixture was cooled with ice. A dichloromethane (3 ml) solution of 1.39 g of crude 4-acetyl-2-methylbenzyl chloride was added slowly to the mixture, and stirred for 2 hours with ice cooling. 24 ml of tetrahydrofuran was added to the reaction solution, and further stirred for 2 hours at room temperature. Then, large part of the solvent was distilled off under reduced pressure, and the slurry-state reaction solution was filtered. The obtained solid was washed with water and toluene. The solid was dried under reduced pressure to obtain 1.03 g of 4-acetyl-2-methylbenzoic acid amide.

$^1$H-NMR (CDCl$_3$, Me$_4$Si, 400 MHz) δ 7.76-7.84 (m, 2H), 7.53 (d, J=7.9 Hz, 1H), 5.87 (br s, 1H), 5.81 (br s, 1H), 2.56 (s, 3H), 2.55 (s, 3H). Melting point 152-154° C.

Example 1-1

Synthesis of 1-(4-bromo-3-methylphenyl)-3-(3,5-dichlorophenyl)-4,4,4-trifluoro-3-hydroxybutan-1-one Example 1-1-1

2.13 g of 4-bromo-3-methylacetophenone which can be synthesized in accordance with the method described in WO 96/19477 pamphlet, 2.43 g of 3',5'-dichloro-2,2,2-trifluoroacetophenone, 4.86 g of n-heptane and 0.20 g of triethylamine were fed and the mixture was stirred for 14 hours at 60° C. The solid generated in the reaction solution was collected by filtration under reduced pressure, and the solid was washed with 1 ml of n-heptane. 4.15 g of 1-(4-bromo-3-methylphenyl)-3-(3,5-dichlorophenyl)-4,4,4-trifluoro-3-hydroxybutan-1-one as a white solid was obtained by drying under reduced pressure.

Example 1-1-2

6.39 g of 4-bromo-3-methylacetophenone, 7.29 g of 3',5'-dichloro-2,2,2-trifluoroacetophenone, 19.2 g of n-heptane and 5.56 g of tributylamine were fed and the mixture was stirred for 9 hours at 60° C. The solid generated in the reaction solution was collected by filtration under reduced pressure, and the solid was washed with 6.4 g of n-heptane. 10.9 g of 1-(4-bromo-3-methylphenyl)-3-(3,5-dichlorophenyl)-4,4,4-trifluoro-3-hydroxybutan-1-one as a white solid was obtained by drying under reduced pressure.

Example 1-1-3

0.26 g of 4-bromo-3-methylacetophenone, 0.30 g of 3',5'-dichloro-2,2,2-trifluoroacetophenone, 0.75 g of chlorobenzene and 0.22 g of tributylamine were fed and the mixture was stirred for 96 hours at room temperature. The solid generated in the reaction solution was collected by filtration under reduced pressure. 0.43 g of 1-(4-bromo-3-methylphenyl)-3-(3,5-dichlorophenyl)-4,4,4-trifluoro-3-hydroxybutan-1-one as a white solid was obtained by drying under reduced pressure.

Example 1-1-4

5.33 g of 4-bromo-3-methylacetophenone, 6.08 g of 3',5'-dichloro-2,2,2-trifluoroacetophenone, 6.08 g of toluene and 1.39 g of tributylamine were fed and the mixture was stirred for 13 hours at 60° C. The solid generated in the reaction solution was collected by filtration under reduced pressure. 10.16 g of 1-(4-bromo-3-methylphenyl)-3-(3,5-dichlorophenyl)-4,4,4-trifluoro-3-hydroxybutan-1-one as a white solid was obtained by drying under reduced pressure.

Example 1-1-5

1.07 g of 4-bromo-3-methylacetophenone, 1.22 g of 3',5'-dichloro-2,2,2-trifluoroacetophenone and 5.0 g of tributylamine were fed and the mixture was stirred for 21 hours at room temperature. The solid generated in the reaction solution was collected by filtration under reduced pressure, and the solid was washed with 1.5 ml of n-heptane. 2.01 g of 1-(4-bromo-3-methylphenyl)-3-(3,5-dichlorophenyl)-4,4,4-trifluoro-3-hydroxybutan-1-one as a white solid was obtained by drying under reduced pressure.

Example 1-1-6

1.07 g of 4-bromo-3-methylacetophenone, 1.22 g of 3',5'-dichloro-2,2,2-trifluoroacetophenone, 3.66 g of distilled water, 0.14 g of potassium carbonate and 33 mg of sodium laurate were fed and the mixture was stirred for 12 hours at 70° C. The solid generated in the reaction solution was collected by filtration under reduced pressure, and the solid was washed with 2 ml of distilled water. 2.10 g of 1-(4-bromo-3-methylphenyl)-3-(3,5-dichlorophenyl)-4,4,4-trifluoro-3-hydroxybutan-1-one as a white solid was obtained by drying under reduced pressure.

Example 1-1-7

1.28 g of 4-bromo-3-methylacetophenone, 1.46 g of 3',5'-dichloro-2,2,2-trifluoroacetophenone, 4.38 g of distilled water, 0.17 g of potassium carbonate and 35 mg of sodium decanoate were fed and the mixture was stirred for 6 hours at 80° C. 8.22 g of toluene and 0.4 ml of concentrated hydrochloric acid were added to the slurry-state reaction solution. A small amount of the organic phase was taken, diluted with acetonitrile, and analyzed by high-performance liquid chromatography. A percentage of the area of 1-(4-bromo-3-methylphenyl)-3-(3,5-dichlorophenyl)-4,4,4-trifluoro-3-hydroxybutan-1-one was 96.1% (detected by UV detector at a wavelength of 220 nm, and calculated with omitting the peak of toluene).

Example 1-1-8

1.07 g of 4-bromo-3-methylacetophenone, 1.2 g of 3',5'-dichloro-2,2,2-trifluoroacetophenone, 3.66 g of distilled water, 0.14 g of potassium carbonate and 33 mg of sodium laurate were fed and the mixture was stirred for 14 hours at 70° C. The slurry-state reaction solution was filtered under reduced pressure, and the solid was washed with distilled water. 2.10 g of 1-(4-bromo-3-methylphenyl)-3-(3,5-dichlorophenyl)-4,4,4-trifluoro-3-hydroxybutan-1-one as a white solid was obtained by drying under reduced pressure.

Example 1-1-9

0.44 g of 4-bromo-3-methylacetophenone, 0.50 g of 3',5'-dichloro-2,2,2-trifluoroacetophenone, 5.0 g of distilled water, 0.14 g of potassium carbonate and 27 mg of sodium dodecane sulfonate were fed and the mixture was stirred for 6 hours at 80° C. A small amount of the slurry-state reaction solution was taken, diluted with acetonitrile, and analyzed by high-performance liquid chromatography. A percentage of the area of 1-(4-bromo-3-methylphenyl)-3-(3,5-dichlorophenyl)-4,4,4-trifluoro-3-hydroxybutan-1-one was 94.5% (detected by UV detector at a wavelength of 220 nm).

Example 1-1-10

0.64 g of 4-bromo-3-methylacetophenone, 0.73 g of 3',5'-dichloro-2,2,2-trifluoroacetophenone, 2.19 g of distilled water, 83 mg of potassium carbonate and 11 mg of sodium dodecylbenzenesulfonate were fed and the mixture was stirred for 5 hours at 80° C. 4.11 g of toluene and 0.3 ml of concentrated hydrochloric acid were added to the slurry-state reaction solution. A small amount of the organic phase was taken, diluted with acetonitrile, and analyzed by high-performance liquid chromatography. A percentage of the area of 1-(4-bromo-3-methylphenyl)-3-(3,5-dichlorophenyl)-4,4,4-trifluoro-3-hydroxybutan-1-one was 95.7% (detected by UV detector at a wavelength of 220 nm, and calculated with omitting the peak of toluene).

Example 1-1-11

4.26 g of 4-bromo-3-methylacetophenone, 4.86 g of 3',5'-dichloro-2,2,2-trifluoroacetophenone, 20.0 g of distilled water, 1.38 g of potassium carbonate and 0.29 g of sodium dodecyl sulfonate were fed and the mixture was stirred for 5 hours at 80° C. 20.0 g of toluene and 0.4 ml of concentrated hydrochloric acid were added to the slurry-state reaction solution. The solution was further stirred for 2 hours at 80° C., and separated. A small amount of the organic phase was taken, diluted with acetonitrile, and analyzed by high-performance liquid chromatography. A percentage of the area of 1-(4-bromo-3-methylphenyl)-3-(3,5-dichlorophenyl)-4,4,4-trifluoro-3-hydroxybutan-1-one was 94.2% (detected by UV detector at a wavelength of 220 nm, and calculated with omitting the peak of toluene).

Example 1-1-12

1.07 g of 4-bromo-3-methylacetophenone, 1.22 g of 3',5'-dichloro-2,2,2-trifluoroacetophenone, 7.32 g of distilled water, 0.35 g of potassium carbonate and 0.72 g of methanol were fed and the mixture was stirred for 8 hours at 70° C. 9.16 g of toluene and 0.5 ml of concentrated hydrochloric acid were added to the slurry-state reaction solution. A small amount of the organic phase was taken, diluted with acetonitrile, and analyzed by high-performance liquid chromatography. A percentage of the area of 1-(4-bromo-3-methylphenyl)-3-(3,5-dichlorophenyl)-4,4,4-trifluoro-3-hydroxybutan-1-one was 91.7% (detected by UV detector at a wavelength of 220 nm, and calculated with omitting the peak of toluene).

Example 1-1-13

0.64 g of 4-bromo-3-methylacetophenone, 0.73 g of 3',5'-dichloro-2,2,2-trifluoroacetophenone, 4.38 g of distilled water, 0.21 g of potassium carbonate and 0.44 g of N,N'-dimethylformamide were fed and the mixture was stirred for 7 hours at 70° C. 4.11 g of toluene and 0.6 ml of concentrated hydrochloric acid were added to the slurry-state reaction solution. A small amount of the organic phase was taken, diluted with acetonitrile, and analyzed by high-performance liquid chromatography. A percentage of the area of 1-(4-bromo-3-methylphenyl)-3-(3,5-dichlorophenyl)-4,4,4-trifluoro-3-hydroxybutan-1-one was 95.0% (detected by UV detector at a wavelength of 220 nm, and calculated with omitting the peak of toluene and N,N'-dimethylformamide).

Example 1-2

Synthesis of 4-(3-(3,5-dichlorophenyl)-4,4,4-trifluoro-3-hydroxybutanoyl)-2-methylbenzoic Acid and the Salt Thereof

Example 1-2-1

0.53 g of 4-acetyl-2-methylbenzoic acid, 0.73 g of 3',5'-dichloro-2,2,2-trifluoroacetophenone, 3.65 g of distilled water, 0.48 g of potassium carbonate and 33 mg of sodium laurate were fed and the mixture was stirred for 9 hours at 60° C. 0.8 ml of concentrated hydrochloric acid was added to the slurry-state reaction solution, and the solid was extracted with 10 ml of ethyl acetate. 1.27 g of a yellow solid was obtained by concentrating the organic phase under reduced pressure. This solid was washed with mixed liquid of 5 ml of n-heptane and 0.5 ml of ethyl acetate to obtain 1.17 g of 4-(3-(3,5-dichlorophenyl)-4,4,4-trifluoro-3-hydroxybutanoyl)-2-methylbenzoic acid as a flesh color solid.

$^1$H-NMR (CDCl$_3$, Me$_4$Si, 400 MHz) δ 8.17 (d, J=8.2 Hz, 1H), 7.79-7.87 (m, 2H), 7.48-7.52 (m, 2H), 7.36 (t, J=1.8 Hz, 1H), 5.61 (br s, 1H), 3.89 (d, J=17.4 Hz, 1H), 3.72 (d, J=17.4 Hz, 1H), 2.74 (s, 3H).

Melting point 171-172° C.

Example 1-2-2

4.46 g of 4-acetyl-2-methylbenzoic acid, 6.08 g of 3',5'-dichloro-2,2,2-trifluoroacetophenone, 18.2 g of toluene and 3.79 g of triethylamine were fed and the mixture was stirred for 13 hours at 60° C. 12.2 g of toluene was added to the slurry-state reaction solution, and the mixture was cooled to room temperature. The reaction solution was filtered under reduced pressure, and the solid was washed with a small amount of toluene. 11.3 g of triethylamine salt of 4-(3-(3,5-dichlorophenyl)-4,4,4-trifluoro-3-hydroxybutanoyl)-2-methylbenzoic acid as a white solid was obtained by drying under reduced pressure.

$^1$H-NMR (CDCl$_3$, Me$_4$Si, 400 MHz) δ 7.67-7.76 (m, 3H), 7.49 (d, J=1.8 Hz, 2H), 7.33 (t, J=1.8 Hz, 1H), 5.98 (br s, 1H), 3.85 (d, J=17.4 Hz, 1H), 3.63 (d, J=17.4 Hz, 1H), 3.12 (q, J=7.1 Hz, 6H), 2.58 (s, 3H), 1.34 (t, J=7.1 Hz, 9H).
Melting point 114-115° C.

Example 1-2-3

0.54 g of 4-acetyl-2-methylbenzoic acid, 0.74 g of 3',5'-dichloro-2,2,2-trifluoroacetophenone, 1.48 g of toluene and 0.34 g of diethylamine were fed and the mixture was stirred for 13 hours at 60° C. 1.48 g of toluene was added to the slurry-state reaction solution, and the mixture was cooled to room temperature. The reaction solution was filtered under reduced pressure, and the solid was washed with a small amount of toluene. 1.42 g of diethylamine salt of 4-(3-(3,5-dichlorophenyl)-4,4,4-trifluoro-3-hydroxybutanoyl)-2-methylbenzoic acid as a white solid was obtained by drying under reduced pressure.
Melting point 112 to 113° C.

Example 1-2-4

0.54 g of 4-acetyl-2-methylbenzoic acid, 0.74 g of 3',5'-dichloro-2,2,2-trifluoroacetophenone, 1.48 g of toluene and 0.46 g of di-n-propylamine were fed and the mixture was stirred for 6 hours at 60° C. 1.48 g of toluene was added to the slurry-state reaction solution, and the mixture was cooled to room temperature. The reaction solution was filtered under reduced pressure, and the solid was washed with a small amount of toluene. 1.48 g of di-n-propylamine salt of 4-(3-(3,5-dichlorophenyl)-4,4,4-trifluoro-3-hydroxybutanoyl)-2-methylbenzoic acid as a white solid was obtained by drying under reduced pressure.
Melting point 133 to 135° C.

Example 1-2-5

0.54 g of 4-acetyl-2-methylbenzoic acid, 0.74 g of 3',5'-dichloro-2,2,2-trifluoroacetophenone, 1.48 g of toluene and 0.46 g of di-i-propylamine were fed and the mixture was stirred for 6 hours at 60° C. 1.48 g of toluene was added to the slurry-state reaction solution, and the mixture was cooled to room temperature. The reaction solution was filtered under reduced pressure, and the solid was washed with a small amount of toluene. 1.39 g of di-i-propylamine salt of 4-(3-(3,5-dichlorophenyl)-4,4,4-trifluoro-3-hydroxybutanoyl)-2-methylbenzoic acid as a white solid was obtained by drying under reduced pressure.
Melting point 135 to 137° C.

Example 1-2-6

0.54 g of 4-acetyl-2-methylbenzoic acid, 0.74 g of 3',5'-dichloro-2,2,2-trifluoroacetophenone, 1.48 g of toluene and 0.46 g of pyrrolidine were fed and the mixture was stirred for 6 hours at 60° C. 1.48 g of toluene was added to the slurry-state reaction solution, and the mixture was cooled to room temperature. The reaction solution was filtered under reduced pressure, and the solid was washed with a small amount of toluene. 1.32 g of pyrrolidine salt of 4-(3-(3,5-dichlorophenyl)-4,4,4-trifluoro-3-hydroxybutanoyl)-2-methylbenzoic acid as a white solid was obtained by drying under reduced pressure.
Melting point 156 to 158° C.

Example 1-2-7

3.0 g of 4-acetyl-2-methylbenzoic acid, 4.5 g of 3',5'-dichloro-2,2,2-trifluoroacetophenone, 15.0 g of ethyl acetate and 1.85 g of diethylamine were fed and the mixture was stirred for 4 hours at 50° C. 9.0 g of toluene was added to the slurry-state reaction solution, and the mixture was cooled to room temperature. Then the mixture was further cooled to 0° C., and stirred for 30 minutes at 0° C. The reaction solution was filtered under reduced pressure, and the solid was washed with a small amount of toluene. 7.63 g of diethylamine salt of 4-(3-(3,5-dichlorophenyl)-4,4,4-trifluoro-3-hydroxybutanoyl)-2-methylbenzoic acid as a white solid was obtained by drying under reduced pressure.

Example 1-3

Synthesis of 4-(3-(3,5-dichlorophenyl)-4,4,4-trifluoro-3-hydroxybutanoyl)-2-methylbenzoic Acid Amide Example 1-3-1

0.35 g of 4-acetyl-2-methylbenzoic acid amide, 0.49 g of 3',5'-dichloro-2,2,2-trifluoroacetophenone, 1.72 g of toluene and 0.19 g of tri-n-butylamine were fed and the mixture was stirred for 25 hours at 60° C. The mixture was left to cool to room temperature and the slurry-state reaction solution was filtered under reduced pressure, and the solid was washed with a small amount of toluene. 0.65 g of 4-(3-(3,5-dichlorophenyl)-4,4,4-trifluoro-3-hydroxybutanoyl)-2-methylbenzoic acid amide as a light yellow solid was obtained by drying under reduced pressure.
$^1$H-NMR (CDCl$_3$, Me$_4$Si, 400 MHz) δ 7.74-7.81 (m, 2H), 7.56 (d, J=8.6 Hz, 1H), 7.47-7.51 (m, 2H), 7.36 (t, J=1.8 Hz, 1H), 5.93 (br s, 1H), 5.79 (br s, 1H), 5.68 (br s, 1H), 3.84 (d, J=17.4 Hz, 1H), 3.68 (d, J=17.6 Hz, 1H), 2.57 (s, 3H).
Melting point 152-154° C.

Example 1-3-2

0.35 g of 4-acetyl-2-methylbenzoic acid amide, 0.49 g of 3',5'-dichloro-2,2,2-trifluoroacetophenone, 2.96 g of distilled water, 83 mg of potassium carbonate and 13 mg of sodium laurate were fed and the mixture was stirred for 5.5 hours at 70° C. The mixture was left to cool to room temperature and the slurry-state reaction solution was filtered under reduced pressure, and the solid was washed with a small amount of distilled water. 0.71 g of 4-(3-(3,5-dichlorophenyl)-4,4,4-trifluoro-3-hydroxybutanoyl)-2-methylbenzoic acid amide as a flesh color solid was obtained by drying under reduced pressure.

Example 1-4

Synthesis of 4-(3-(3,5-dichlorophenyl)-4,4,4-trifluoro-3-hydroxybutanoyl)-2-methyl-N-(pyridin-1-ylmethyl) benzoic Acid Amide 1.52 g of 4-acetyl-2-methyl-N-(pyridin-1-ylmethyl) benzoic acid amide, 1.51 g of 3',5'-dichloro-2,2,2-trifluoroacetophenone, 1.51 g of toluene and 0.52 g of tri-n-butylamine were fed and the mixture was stirred for 10 hours at 60° C. The mixture was left to cool to room temperature and 1 ml of toluene was added to the slurry-state reaction solution. The slurry was filtered under reduced pressure, and the solid was washed with a small amount of toluene. 2.16 g of 4-(3-(3,5-dichlorophenyl)-4,4,4-trifluoro-3-hydroxybutanoyl)-2-methyl-N-(pyridin-2-ylmethyl) benzoic acid amide as a flesh color solid was obtained by drying under reduced pressure.

Example 1-5

Synthesis of ethyl 4-(3-(3,5-dichlorophenyl)-4,4,4-trifluoro-3-hydroxybutanoyl)-2-methylbenzoate 0.63 g of ethyl 4-acetyl-2-methylbenzoate, 0.73 g of 3',5'-dichloro-2,2,2-trifluoroacetophenone, 0.73 g of n-heptane and 0.30 g of triethylamine were fed and the mixture was stirred for 4 hours at 60° C. The mixture was left to cool, and further stirred for one night at room temperature. 0.53 g of n-heptane was added to the slurry-state reaction solution, and the mixture was filtered under reduced pressure. The solid was washed with a small amount of n-heptane, and dried under reduced pressure. 0.97 g of ethyl 4-(3-(3,5-dichlorophenyl)-4,4,4-trifluoro-3-hydroxybutanoyl)-2-methylbenzoate as a light yellow solid was obtained by drying under reduced pressure.

$^1$H-NMR (CDCl$_3$, Me$_4$Si, 400 MHz) δ 7.98 (d, J=8.6 Hz, 1H), 7.75-7.80 (m, 2H), 7.47-7.51 (m, 2H), 7.35 (t, J=1.8 Hz, 1H), 5.64 (br s, 1H), 4.40 (q, J=7.1 Hz, 2H), 3.86 (d, J=17.6 Hz, 1H), 3.69 (d, J=17.6 Hz, 1H), 2.64 (s, 3H), 1.42 (t, J=7.1 Hz, 3H).

Melting point 72-74° C.

Example 1-6

Synthesis of 3-(3,5-bis(trifluoromethyl)phenyl)-1-(3-chloro-4-methylphenyl-4,4,4-trifluoro-3-hydroxybutan-1-one 3.01 g of 3'-chloro-4'-methylacetophenone and 0.99 g of tributylamine was added to a heptane (6 ml) solution of 6.62 g of 3',5'-bis(trifluoromethyl)-2,2,2-trifluoroacetophenone, and the mixture was stirred for 2 hours at 60° C. A small amount of crystal of the target product was added to the reaction mixture. After confirming deposition of the crystal after 1 hour, the reaction mixture was cooled to room temperature. The deposited crystal was collected by filtration and washed with 2 ml of hexane to obtain 7.55 g of the target product (white crystal).

Melting point 81.0 to 84.0° C. $^1$H-NMR (CDCl$_3$, Me$_4$Si, 400 MHz) δ 8.06 (s, 2H), 7.89 (s, 2H), 7.72 (dd, J=7.8, 1.5 Hz, 1H), 7.38 (d, J=7.8 Hz, 1H), 5.90 (s, 1H), 3.85 (d, J=17.4 Hz, 1H), 3.74 (d, J=17.4 Hz, 1H), 2.47 (s, 3H).

Example 1-7

Synthesis of 1-(4-(1H-1,2,4-triazol-1-yl)phenyl)-3-(3,5-dichlorophenyl)-4,4,4-trifluoro-3-hydroxybutan-1-one 2.00 g (10.7 mmol) of 1-(4-(1H-1,2,4-triazol-1-yl)phenyl) ethanone, 2.60 g (10.7 mmol) of 3',5'-dichloro-2,2,2-trifluoroacetophenone, 5.20 g of toluene and 0.59 g (3.2 mmol) of tributylamine were fed and the mixture was stirred for 9 hours at 80° C. After leaving the reaction mixture for one night at room temperature, the deposited solid was filtered under reduced pressure to obtain 3.79 g of 1-(4-(1H-1,2,4-triazol-1-yl)phenyl)-3-(3,5-dichlorophenyl-4,4,4-trifluoro-3-hydroxybutan-1-one as a white solid (yield 82.4%).

Melting point 165 to 166° C.

Example 1-8

Synthesis of 1-(4-(1H-imidazol-1-yl)phenyl)-3-(3,5-dichlorophenyl)-4,4,4-trifluoro-3-hydroxybutan-1-one 0.50 g (2.69 mmol) of 1-(4-(1H-imidazol-1-yl)phenyl) ethanone, 0.65 g (2.69 mmol) of 3',5'-dichloro-2,2,2-trifluoroacetophenone, 1.31 g of toluene and 0.15 g (0.81 mmol) of tributylamine were fed and the mixture was stirred for 8 hours at 60° C. After leaving the reaction mixture for one night at room temperature, the solid was filtered under reduced pressure to obtain 0.94 g of 1-(4-(1H-imidazol-1-yl)phenyl)-3-(3,5-dichlorophenyl)-4,4,4-trifluoro-3-hydroxybutan-1-one as a white solid (yield 85.7%).

Melting point 161 to 162° C.

Example 1-9

Synthesis of 3-(3,5-dichlorophenyl)-4,4,4-trifluoro-3-hydroxy-1-(4-(methylthio)phenyl)butan-1-one 0.50 g (3.01 mmol) of 1-(4-(methylthio)phenyl)ethanone, 0.73 g of (3.01 mmol) of 3',5'-dichloro-2,2,2-trifluoroacetophenone, 1.46 g of toluene and 0.17 g (0.90 mmol) of tributylamine were fed and the mixture was stirred for 15 hours at 60° C. After leaving the reaction mixture for one night at room temperature, separation operation was performed by adding 30 ml of ethyl acetate and 10 ml of water, and the ethyl acetate phase was washed with diluted aqueous solution of hydrochloric acid. After removing the solvent by distilling under reduced pressure, the residue was purified by silica gel column chromatography to obtain 0.56 g of 3-(3,5-dichlorophenyl)-4,4,4-trifluoro-3-hydroxy-1-(4-(methylthio)phenyl)butan-1-one (yield 45.2%).

$^1$H-NMR (CDCl$_3$, Me$_4$Si, 300 MHz) δ 7.84 (d, J=8.7 Hz, 2H), 7.50 (bs, 2H), 7.34 (d, J=1.8 Hz, 1H), 7.29 (d, J=8.7 Hz, 2H), 5.95 (s, 1H), 3.80 (d, J=17.4 Hz, 1H), 3.61 (d, J=17.4 Hz, 1H), 2.54 (s, 3H).

Example 1-10

Synthesis of 1-(6-bromopyridin-3-yl)-3-(3,5-dichlorophenyl)-4,4,4-trifluoro-3-hydroxybutan-1-one 1.00 g (4.99 mmol) of 1-(6-bromopyridin-3-yl)-ethanone, 1.21 g (4.99 mmol) of 3',5'-dichloro-2,2,2-trifluoroacetophenone, 2.42 g of toluene and 0.28 g (1.50 mmol) of tributylamine were fed and the mixture was stirred for 13 hours at 60° C. After cooling the reaction solution to room temperature, the solid was filtered under reduced pressure to obtain 0.85 g of 1-(6-bromopyridin-3-yl)-3-(3,5-dichlorophenyl)-4,4,4-trifluoro-3-hydroxybutan-1-one as a white solid (yield 38.4%) Melting point 102-104° C.

Example 1-11

Synthesis of 1-(6-(1H-1,2,4-triazol-1-yl)pyridin-3-yl)-3-(3,5-dichlorophenyl)-4,4,4-trifluoro-3-hydroxybutan-1-one 1.10 g (5.84 mmol) of 1-(6-(1H-1,2,4-triazol-1-yl)pyridin-3-yl) ethanone, 1.42 g (5.84 mmol) of 3',5'-dichloro-2,2,2-trifluoroacetophenone, 2.84 g of toluene and 0.32 g (1.75 mmol) of tributylamine were fed and the mixture was stirred for 7 hours at 60° C. After leaving the reaction mixture for one night at room temperature, the solid was filtered under reduced pressure to obtain 1.84 g of 1-(6-(1H-

1,2,4-triazol-1-yl)pyridin-3-yl)-3-(3,5-dichlorophenyl)-4,4,4-trifluoro-3-hydroxybutan-1-one as a white solid (yield 73.1%).

Melting point 135 to 136° C.

Example 1-12

Synthesis of 5-(3-(3,5-dichlorophenyl)-4,4,4-trifluoro-3-hydroxybutanoyl)-2-(1H-1,2,4-triazol-1-yl)benzonitrile 1.00 g (4.71 mmol) of 5-acetyl-2-(1H-1,2,4-triazol-1-yl)benzonitrile, 1.15 g (4.71 mmol) of 3',5'-dichloro-2,2,2-trifluoroacetophenone, 2.30 g of toluene and 0.26 g (1.41 mmol) of tributylamine were fed and the mixture was stirred for 24 hours at 60° C. The mixture was cooled to room temperature, and a separation operation was performed by adding 20 ml of toluene and an aqueous solution prepared with 0.15 g (1.41 mmol) of 35% hydrochloric acid and 10 ml of water. The toluene phase was washed with 10 ml of water. After removing the solvent by distilling under reduced pressure, the residue was purified by silica gel column chromatography to obtain 1.20 g of 5-(3-(3,5-dichlorophenyl)-4,4,4-trifluoro-3-hydroxybutanoyl)-2-(1H-1,2,4-triazol-1-yl) benzonitrile (yield 56.0%).

$^1$H-NMR (CDCl$_3$, Me$_4$Si, 300 MHz) δ 9.00 (s, 1H), 8.39 (d, J=2.1 Hz, H), 8.29 (dd, J=9.0 Hz, 2.1 Hz, 1H), 8.24 (s, 1H), 8.06 (d, J=9.0 Hz, 1H), 7.48 (d, J=1.5 Hz, 2H), 7.38 (d, J=1.5 Hz, 1H), 5.28 (s, 1H), 3.80 (dd, J=27.3 Hz, 17.4 Hz, 2H).

Example 1-13

Synthesis of 5-(3-(3,5-dichlorophenyl)-4,4,4-trifluoro-3-hydroxybutanoyl)-2-fluorobenzonitrile 1.01 g (6.19 mmol) of 2-acetyl-2-fluorobenzonitrile, 1.50 g (6.19 mmol) of 3',5'-dichloro-2,2,2-trifluoroacetophenone, 3.00 g of toluene and 0.34 g (1.86 mmol) of tributylamine were fed and the mixture was stirred for 16 hours at 60° C. After cooling the reaction solution to room temperature, the solid was filtered under reduced pressure to obtain 2.06 g of 5-(3-(3,5-dichlorophenyl)-4,4,4-trifluoro-3-hydroxybutanoyl)-2-fluorobenzonitrile as a white solid (yield 82.0%).

Melting point 146 to 147° C.

Example 2-1

Synthesis of 1-(4-bromo-3-methylphenyl)-3-(3,5-dichlorophenyl)-4,4,4-trifluoro-2-buten-1-one Example 2-1-1

1.37 g of 1-(4-bromo-3-methylphenyl)-3-(3,5-dichlorophenyl)-4,4,4-trifluoro-3-hydroxybutan-1-one, 2.74 g of toluene and 0.89 g of thionyl chloride were fed, and the mixture was heated to 80° C. 0.48 g of pyridine was slowly added in dropwise, and the mixture was stirred for 90 minutes at 80° C. The mixture was cooled to room temperature, and separated by adding iced water. The organic phase was washed with a diluted aqueous solution of sodium hydroxide, and the solvent was distilled off under reduced pressure. 1.31 g of 1-(4-bromo-3-methylphenyl)-3-(3,5-dichlorophenyl)-4,4,4-trifluoro-2-buten-1-one was obtained as a yellow solid.

Example 2-1-2

6.84 g of 1-(4-bromo-3-methylphenyl-3-(3,5-dichlorophenyl)-4,4,4-trifluoro-3-hydroxybutan-1-one, 13.7 g of toluene and 4.46 g of thionyl chloride were fed, and the mixture was heated to 70° C. 3.64 g of 2-methyl-5-ethylpyridine was slowly added in dropwise, and the mixture was stirred for 70 minutes at 70° C. The mixture was cooled to room temperature, and separated by adding 6.84 g of water. The organic phase was washed with a diluted aqueous solution of sodium hydroxide, and the solvent was distilled off under reduced pressure. 6.60 g of 1-(4-bromo-3-methylphenyl)-3-(3,5-dichlorophenyl)-4,4,4-trifluoro-2-buten-1-one was obtained as a yellow solid.

Example 2-1-3

0.91 g of 1-(4-bromo-3-methylphenyl-3-(3,5-dichlorophenyl)-4,4,4-trifluoro-3-hydroxybutan-1-one, 1.82 g of toluene and 0.36 g of thionyl chloride were fed, and the mixture was heated to 30° C. 0.56 g of n-tributylamine was slowly added in dropwise. The mixture was heated to 70° C., and stirred for 7 hours. The mixture was cooled to room temperature, and separated by adding iced water. The organic phase was washed with water, and the solvent was distilled off under reduced pressure. 0.86 g of 1-(4-bromo-3-methylphenyl)-3-(3,5-dichlorophenyl)-4,4,4-trifluoro-2-buten-1-one was obtained as a yellow solid.

Example 2-1-4

2.28 g of 1-(4-bromo-3-methylphenyl-3-(3,5-dichlorophenyl)-4,4,4-trifluoro-3-hydroxybutan-1-one, 4 g of toluene and 1.02 g of acetic anhydride were fed, and the mixture was heated to 70° C. A toluene (0.56 g) solution of 61 mg of 4-dimethylaminopyridine, and then 0.59 g of pyridine were slowly added in dropwise, and the mixture was stirred for 19 hours to heat to 80° C. The mixture was cooled to room temperature and separated by adding water, and the solvent was distilled off under reduced pressure. 2.20 g of 1-(4-bromo-3-methylphenyl)-3-(3,5-dichlorophenyl)-4,4,4-trifluoro-2-buten-1-one was obtained as a yellow solid.

Example 2-1-5

0.91 g of 1-(4-bromo-3-methylphenyl)-3-(3,5-dichlorophenyl)-4,4,4-trifluoro-3-hydroxybutan-1-one, 1.82 g of toluene, 0.41 g of acetic anhydride, 24 mg of 4-dimethylaminopyridine and 0.14 g of triethylamine were fed, and stirred for 20 hours at room temperature. 1 ml of water and 0.3 ml of concentrated hydrochloric acid were added and separated. The organic phase was washed with saturated aqueous solution of sodium bicarbonate, and the solvent was distilled off under reduced pressure. 0.89 g of 1-(4-bromo-3-methylphenyl)-3-(3,5-dichlorophenyl)-4,4,4-trifluoro-2-buten-1-one was obtained as a yellow solid.

Example 2-2

Synthesis of 4-(3-(3,5-dichlorophenyl)-4,4,4-trifluoro-2-butenoyl)-2-methylbenzoic Acid Example 2-2-1

1.04 g of triethylamine salt of 4-(3-(3,5-dichlorophenyl)-4,4,4-trifluoro-3-hydroxybutanoyl-2-methylbenzoic acid, 1.7 g of toluene and 24 mg of 4-dimethylaminopyridine were fed, and the mixture was heated to 60° C. Then, 0.41 g of acetic anhydride was added, and the mixture was stirred for 9 hours at 60° C. The reaction solution was left to cool to room temperature and 3.4 g of toluene, 2.5 g of water and 0.3 ml of concentrated hydrochloric acid were added and separated. The organic phase was washed with water, and the solvent was distilled off under reduced pressure. 0.80 g of 4-(3-(3,5-dichlorophenyl)-4,4,4-trifluoro-2-butenoyl)-2-methylbenzoic acid was obtained as a yellow solid.

Here, the target compound obtained in this Synthesis Example is a mixture of geometric isomers whose ratio determined by $^1$H-NMR was about 8.6 to 1. $^1$H-NMR of mainly produced isomer is shown below.

$^1$H-NMR (CDCl$_3$, Me$_4$Si, 400 MHz) δ 8.11 (d, J=8.6 Hz, 1H), 7.67-7.73 (m, 2H), 7.37-7.39 (m, 1H), 7.33 (t, J=1.8 Hz, 1H), 7.16 (br d, J=1.8 Hz, 2H), 2.68 (s, 3H). Melting point 128 to 131° C.

Example 2-2-2

3.0 g of 4-(3-(3,5-dichlorophenyl)-4,4,4-trifluoro-3-hydroxybutanoyl-2-methylbenzoic acid, 7.5 g of toluene and 87 mg of 4-dimethylaminopyridine were fed, and the mixture was heated to 80° C. Then, 1.16 g of acetic anhydride was added in dropwise, and 0.86 g of triethylamine was further added in dropwise. After adding in dropwise, the mixture was stirred for 4 hours at 80° C. 7.5 g of toluene was added to the reaction solution, and the solution was cooled to room temperature. A water (8.1 g) solution of 0.77 g of sodium hydroxide was added in dropwise to the reaction solution, and the mixture was separated. The organic phase was analyzed by high-performance liquid chromatography (wavelength 254 nm). Two geometric isomers derived from 4-(3-(3,5-dichlorophenyl)-4,4,4-trifluoro-2-butenoyl)-2-methylbenzoic acid were produced and each value of area was 82.8% and 16.9%.

Example 2-3

Synthesis of 4-(3-(3,5-dichlorophenyl)-4,4,4-trifluoro-2-butenoyl)-2-methylbenzoic Acid Amide 0.48 g of 4-(3-(3,5-dichlorophenyl)-4,4,4-trifluoro-3-hydroxybutanoyl)-2-methylbenzoic acid amide, 1.5 g of toluene, 0.23 g of acetic anhydride, 27 mg of 4-dimethylaminopyridine and 0.23 g of triethylamine were fed and the mixture was stirred for 2.5 hours at 30° C. 2 ml of iced water and 2 drops of concentrated hydrochloric acid were added to the reaction solution, and the deposited solid was collected by filtration. The solid was washed with a small amount of toluene and distilled water, and dried under reduced pressure. 0.32 g of 4-(3-(3,5-dichlorophenyl)-4,4,4-trifluoro-2-butenoyl)-2-methylbenzoic acid amide was obtained as a flesh color solid.

Here, the target compound obtained in this Synthesis Example is only a single geometric isomer.

$^1$H-NMR (CDCl$_3$, Me$_4$Si, 400 MHz) δ 7.63-7.70 (m, 2H), 7.51 (d, J=7.7 Hz, 1H), 7.36-7.39 (m, 1H), 7.34 (t, J=1.8 Hz, 1H), 7.15 (br d, J=1.8 Hz, 2H), 5.84 (br s, 1H), 5.74 (br s, 1H), 2.52 (s, 3H). Melting point 113 to 115° C.

Example 2-4

Synthesis of ethyl 4-(3-(3,5-dichlorophenyl)-4,4,4-trifluoro-2-butenoyl)-2-methylbenzoate 0.96 g of ethyl 4-(3-(3,5-dichlorophenyl)-4,4,4-trifluoro-3-hydroxybutanoyl)-2-methylbenzoate, 2.0 g of toluene, 0.43 g of acetic anhydride, 26 mg of 4-dimethylaminopyridine and 0.43 g of triethylamine were fed and the mixture was stirred for 3 hours at 30° C. 2 ml of iced water, 2 drops of concentrated hydrochloric acid and 5 ml of toluene were added to the reaction solution, and separated. The organic phase was washed with water, and the solvent was distilled off under reduced pressure to obtain 0.94 g of ethyl 4-(3-(3,5-dichlorophenyl)-4,4,4-trifluoro-2-butenoyl)-2-methylbenzoate as a red solid.

Here, the target compound obtained in this Synthesis Example is a mixture of geometric isomers whose ratio determined by $^1$H-NMR was about 15 to 1. $^1$H-NMR data of mainly produced geometric isomer are shown below.

$^1$H-NMR (CDCl$_3$, Me$_4$Si, 400 MHz) δ 7.93 (d, J=8.6 Hz, 1H), 7.63-7.69 (m, 2H), 7.37-7.40 (m, 1H), 7.33 (t, J=1.8 Hz, 1H), 7.13-7.16 (m, 2H), 4.38 (q, J=7.1 Hz, 2H), 2.62 (s, 3H), 1.41 (t, J=7.1 Hz, 3H). Melting point 36 to 38° C.

Example 2-5

Synthesis of 4-(3-(3,5-dichlorophenyl)-4,4,4-trifluoro-2-butenoyl)-2-methyl-N-(pyridin-2-ylmethyl) benzoic Acid Amide 0.78 g of 4-(3-(3,5-dichlorophenyl)-4,4,4-trifluoro-3-hydroxybutanoyl)-2-methyl-N-(pyridin-2-ylmethyl) benzoic acid amide, 4.3 g of toluene, 0.58 g of acetic anhydride, 20 mg of 4-dimethylaminopyridine, 0.40 g of tri-n-butylamine were fed and the mixture was stirred for 2.5 hours at 30° C. 2 ml of iced water was added to the reaction solution, and the reaction solution was concentrated under reduced pressure. The residue was passed through a column filled with silica gel, and the silica gel was washed with a small amount of 1:1 mixed solution of n-hexane:ethyl acetate. The organic phases were combined and the solvent was distilled off under reduced pressure to obtain 0.64 g of 4-(3-(3,5-dichlorophenyl)-4,4,4-trifluoro-2-butenoyl)-2-methyl-N-(pyridin-2-ylmethyl) benzoic acid amide as a yellow solid.

Here, the target compound obtained in this Synthesis Example is a mixture of geometric isomers whose ratio determined by $^1$H-NMR was 40 to 1.

Example 2-6

Synthesis of 3-(3,5-bis(trifluoromethyl)phenyl)-1-(3-chloro-4-methylphenyl)-4,4,4-trifluoro-2-buten-1-one Example 2-6-1

3-(3,5-bis(trifluoromethyl)phenyl)-1-(3-chloro-4-methylphenyl)-4,4,4-trifluoro-2-buten-1-one 1.15 g of 3-(3,5-bis(trifluoromethyl)phenyl)-1-(3-chloro-4-methylphenyl)-4,4,4-trifluoro-3-hydroxybutan-1-one, 2.3 g of toluene, 0.49 g of acetic anhydride, 29 mg of 4-dimethylaminopyridine and 0.38 g of pyridine were fed, and stirred for 9 hours at 70° C. The mixture was cooled to room temperature, and separated by adding 5 ml of toluene, iced water and 0.6 ml of concentrated hydrochloric acid. The organic phase was washed with water, and the solvent was distilled off under reduced pressure. The obtained residue was roughly purified by using a small amount of silica gel to obtain 1.09 g of 3-(3,5-bis(trifluoromethyl)phenyl)-1-(3-chloro-4-methylphenyl)-4,4,4-trifluoro-2-buten-1-one as yellow liquid.

Here, the target compound obtained in this Synthesis Example is a mixture of geometric isomers whose ratio determined by $^1$H-NMR was about 10 to 1. $^1$H-NMR of mainly produced isomer is shown below.

¹H-NMR (CDCl₃, Me₄Si, 300 MHz) δ 7.87 (s, 1H), 7.77 (d, J=2.1 Hz, 1H), 7.73 (s, 2H), 7.61 (dd, J=8.1, 2.1 Hz, 1H), 7.50 (q, J=1.2 Hz, 1H), 7.32 (d, J=8.1 Hz, 1H), 2.44 (s, 3H).

Example 2-6-2

3-(3,5-bis(trifluoromethyl)phenyl)-1-(3-chloro-4-methylphenyl)-4,4,4-trifluoro-2-buten-1-one 0.96 g of 3-(3,5-bis(trifluoromethyl)phenyl)-1-(3-chloro-4-methylphenyl)-4,4,4-trifluoro-3-hydroxybutan-1-one, 1.92 g of toluene, 0.48 g of thionyl chloride and 0.32 g of pyridine were fed, and stirred for 6 hours at 70° C. The mixture was cooled to room temperature, and separated by adding 10 ml of toluene and iced water. The organic phase was washed with water, and the solvent was distilled off under reduced pressure. The obtained residue was roughly purified by using a small amount of silica gel to obtain 0.92 g of 3-(3,5-bis(trifluoromethyl)phenyl)-1-(3-chloro-4-methylphenyl)-4,4,4-trifluoro-2-buten-1-one as yellow liquid.

Example 2-7

Synthesis of 1-(4-(1H-1,2,4-triazol-1-yl)phenyl)-3-(3,5-dichlorophenyl)-4,4,4-trifluoro-2-buten-1-one After adding 6.00 g of toluene to 2.00 g (4.65 mmol) of 1-(4-(1H-1,2,4-triazol-1-yl)phenyl)-3-(3,5-dichlorophenyl)-4,4,4-trifluoro-3-hydroxybutan-1-one, 1.11 g (9.30 mmol) of thionyl chloride and 0.74 g (9.30 mmol) of pyridine were added at 80° C., and stirred for 3 hours. The reaction solution was cooled to room temperature, and separated by adding 50 ml of chloroform and 20 ml of water. After washing the organic phase with an aqueous solution of 0.37 g of sodium hydroxide dissolved into 2.0 g of water, then the phase was washed with water. The solvent was distilled off under reduced pressure to obtain 1.58 g of 1-(4-(1H-1,2,4-triazol-1-yl)phenyl)-3-(3,5-dichlorophenyl)-4,4,4-trifluoro-2-buten-1-one (Yield 82.4%). Here, the target compound obtained in this Synthesis Example is a mixture of geometric isomers whose ratio determined by ¹H-NMR was 4 to 1. ¹H-NMR data of mainly produced geometric isomer are shown below.

¹H-NMR (CDCl₃, Me₄Si, 300 MHz) δ 8.67 (s, 1H), 8.15 (m, 1H), 7.96 (dd, J=6.9 Hz, 2.1 Hz, 2H), 7.82 (dd, J=6.9 Hz, 2.1 Hz, 2H), 7.40 (d, J=1.5 Hz, 1H), 7.30 (d, J=1.5 Hz, 1H), 7.17 (d, J=1.5 Hz, 2H)

Example 2-8

Synthesis of 1-(4-(1H-imidazol-1-yl)phenyl)-3-(3,5-dichlorophenyl)-4,4,4-trifluoro-2-buten-1-one After adding 2.69 g of toluene to 0.90 g (2.09 mmol) of 1-(4-(1H-imidazol-1-yl)phenyl)-3-(3,5-dichlorophenyl)-4,4,4-trifluoro-3-hydroxybutan-1-one, 0.50 g (4.19 mmol) of thionyl chloride and 0.33 g (4.19 mmol) of pyridine were added at 80° C., and stirred for 1 hour. The reaction solution was cooled to room temperature, and separated by adding 35 ml of chloroform and 20 ml of water. After washing the organic phase with an aqueous solution of 0.37 g of sodium hydroxide dissolved into 2.0 g of water, the organic phase was washed with an aqueous solution prepared by 0.44 g (4.19 mmol) of 35% hydrochloric acid and 20 ml of water, and then washed with water. The solvent was distilled off under reduced pressure to obtain 0.70 g of 1-(4-(1H-imidazol-1-yl)phenyl)-3-(3,5-dichlorophenyl)-4,4,4-trifluoro-2-buten-1-one (yield 81.7%).

Here, the target compound obtained in this Synthesis Example is a mixture of geometric isomers whose ratio determined by ¹H-NMR was 6 to 1. ¹H-NMR data of mainly produced geometric isomer are shown below.

¹H-NMR (CDCl₃, Me₄Si, 300 MHz) δ 7.95 (m, 4H), 7.49 (m, 2H), 7.39 (d, J=1.5 Hz, 1H), 7.34 (m, 2H), 7.17 (d, J=1.8 Hz, 2H)

Example 2-9

Synthesis of 3-(3,5-dichlorophenyl)-4,4,4-trifluoro-1-(4-(methylthio)phenyl)2-buten-1-one After adding 1.44 g of toluene to 0.48 g (1.17 mmol) of 3-(3,5-dichlorophenyl)-4,4,4-trifluoro-3-hydroxy-1-(4-(methylthio)phenyl) butan-1-one, 0.28 g (2.34 mmol) of thionyl chloride and 0.19 g (2.34 mmol) of pyridine were added at 80° C., and stirred for 3 hours. The reaction was traced by high-performance liquid chromatography. Since the raw materials did not disappear, 0.14 g (1.17 mmol) of thionyl chloride and 0.09 g (1.17 mmol) of pyridine were added and stirred for 1 hour. The reaction solution was cooled to room temperature, and separated by adding 20 ml of ethyl acetate and 10 ml of water. After washing the ethyl acetate phase with an aqueous solution of 0.14 g of sodium hydroxide dissolved into 10 ml of water, the phase was washed with water. The solvent was distilled off under reduced pressure to obtain 0.37 g of 3-(3,5-dichlorophenyl)-4,4,4-trifluoro-1-(4-(methylthio)phenyl)-2-buten-1-one (yield 81.8%).

Here, the target compound obtained in this Synthesis Example is a mixture of geometric isomers whose ratio determined by ¹H-NMR was 5 to 1. ¹H-NMR data of mainly produced geometric isomer are shown below.

¹H-NMR (CDCl₃, Me₄Si, 300 MHz) δ 7.73 (dd, J=6.9 Hz, 1.8 Hz, 2H), 7.37 (m, 1H), 7.32 (m, 1H), 7.24 (dd, J=6.9 Hz, 1.8 Hz, 2H), 7.16 (d, J=1.8 Hz, 2H), 2.52 (s, 3H)

Example 2-10

Synthesis of 1-(6-bromopyridin-3-yl)-3-(3,5-dichlorophenyl)-4,4,4-trifluoro-2-buten-1-one After adding 2.42 g of toluene to 0.81 g (1.82 mmol) of 1-(6-bromopyridin-3-yl)-3-(3,5-dichlorophenyl)-4,4,4-trifluoro-3-hydroxybutan-1-one, 0.44 g (3.64 mmol) of thionyl chloride and 0.29 g (3.64 mmol) of pyridine were added at 80° C., and stirred for 3 hours. The reaction solution was cooled to room temperature, and separated by adding 15 ml of ethyl acetate and 10 ml of water. After washing the ethyl acetate phase with an aqueous solution of 0.15 g of sodium hydroxide dissolved into 10 ml of water, the phase was washed with water. The solvent was distilled off under reduced pressure to obtain 0.63 g of 1-(6-bromopyridin-3-yl)-3-(3,5-dichlorophenyl)-4,4,4-trifluoro-2-buten-1-one (yield 81.4%).

Here, the target compound obtained in this Synthesis Example is a mixture of geometric isomers whose ratio determined by ¹H-NMR was 4 to 1. ¹H-NMR data of mainly produced geometric isomer are shown below.

¹H-NMR (CDCl₃, Me₄Si, 300 MHz) δ 8.80 (d, J=2.4 Hz, 1H), 8.04 (dd, J=8.1 Hz, 2.4 Hz, 1H), 7.42 (bs, 1H), 7.37 (d, J=2.4 Hz, 1H), 7.32 (d, J=1.8 Hz, 1H), 7.15 (d, J=1.8 Hz, 2H)

Example 2-11

Synthesis of 1-(6-(1H-1,2,4-triazol-1-yl)pyridin-3-yl)-3-(3,5-dichlorophenyl)-4,4,4-trifluoro-2-buten-1-one After adding 5.34 g of toluene to 1.78 g (4.12 mmol) of 1-(6-(1H-1,2,4-triazol-1-yl)pyridin-3-yl)-3-(3,5-dichlorophenyl)-4,4,4-trifluoro-3-hydroxybutan-1-one, 0.98 g (8.25 mmol) of thionyl chloride and 0.65 g (8.25 mmol) of pyridine were added at 80° C., and stirred for 3 hours. The reaction solution was cooled to room temperature, and separated by adding 20 ml of ethyl acetate and 10 ml of water. After washing the ethyl acetate phase with an aqueous solution of 0.33 g of sodium hydroxide dissolved into 10 ml of water, the phase was washed with water. The solvent was distilled off under reduced pressure to obtain 1.69 g of 1-(6-(1H-1,2,4-triazol-1-yl)pyridin-3-yl)-3-(3,5-dichlorophenyl)-4,4,4-trifluoro-2-buten-1-one (yield 99.4%).

Here, the target compound obtained in this Synthesis Example is a mixture of geometric isomers whose ratio determined by $^1$H-NMR was 13 to 2. $^1$H-NMR data of mainly produced geometric isomer are shown below.

$^1$H-NMR (CDCl$_3$, Me$_4$Si, 300 MHz) δ 9.22 (s, 1H), 8.88 (d, J=2.4 Hz, 1H), 8.29 (dd, J=8.7 Hz, 2.4 Hz, 1H), 8.13 (s, 1H), 8.00 (d, J=8.7 Hz, 1H), 7.36 (m, 2H), 7.18 (m, 2H)

Example 2-12

Synthesis of 5-(3-(3,5-dichlorophenyl)-4,4,4-trifluoro-2-butenoyl)-2-(1H-1,2,4-triazol-1-yl) benzonitrile After adding 3.00 g of toluene to 1.00 g (2.19 mmol) of 5-(3-(3,5-dichlorophenyl)-4,4,4-trifluoro-3-hydroxybutanoyl)-2-(1H-1,2,4-triazol-1-yl) benzonitrile, 0.52 g (4.39 mmol) of thionyl chloride and 0.35 g (4.39 mmol) of pyridine were added at 80° C., and stirred for 2 hours. The reaction solution was cooled to room temperature, and separated by adding 20 ml of ethyl acetate and 10 ml of water. After washing the ethyl acetate phase with an aqueous solution of 0.18 g of sodium hydroxide dissolved into 10 ml of water, the phase was washed with water. The solvent was distilled off under reduced pressure to obtain 0.92 g of 5-(3-(3,5-dichlorophenyl)-4,4,4-trifluoro-2-butenoyl)-2-(1H-1,2,4-triazol-1-yl) benzonitrile (yield 99.4%).

Here, the target compound obtained in this Synthesis Example is a mixture of geometric isomers whose ratio determined by $^1$H-NMR was 6 to 1. $^1$H-NMR data of mainly produced geometric isomer are shown below.

$^1$H-NMR (CDCl$_3$, Me$_4$Si, 300 MHz) δ 8.97 (s, 1H), 8.27 (d, J=2.1 Hz, 1H), 8.23 (s, 1H), 8.18 (dd, J=8.4 Hz, 2.1 Hz, 1H), 8.00 (d, J=8.4 Hz, 1H), 7.38 (m, 2H), 7.17 (m, 2H)

Example 2-13

Synthesis of 5-(3-(3,5-dichlorophenyl)-4,4,4-trifluoro-2-butenoyl)-2-fluorobenzonitrile After adding 5.85 g of toluene to 1.95 g (4.81 mmol) of 5-(3-(3,5-dichlorophenyl)-4,4,4-trifluoro-3-hydroxybutanoyl)-2-fluorobenzonitrile, 1.14 g (9.62 mmol) of thionyl chloride and 0.76 g (9.62 mmol) of pyridine were added at 80° C., and stirred for 2 hours. The reaction solution was cooled to room temperature, and separated by adding 20 ml of toluene and 10 ml of water. After washing the toluene phase with an aqueous solution of 0.39 g of sodium hydroxide dissolved into 10 ml of water, the phase was washed with water. The solvent was distilled off under reduced pressure to obtain 1.59 g of 5-(3-(3,5-dichlorophenyl)-4,4,4-trifluoro-2-butenoyl)-2-fluorobenzonitrile (yield 85.2%).

Here, the target compound obtained in this Synthesis Example is a mixture of geometric isomers whose ratio determined by $^1$H-NMR was 5 to 1. $^1$H-NMR data of mainly produced geometric isomer are shown below.

$^1$H-NMR (CDCl$_3$, Me$_4$Si, 300 MHz) δ 8.10 (m, 2H), 7.42 (m, 1H), 7.33 (m, 2H), 7.15 (m, 2H)

Example 3-1

One-Pot Synthesis of 1-(4-bromo-3-methylphenyl)-3-(3,5-dichlorophenyl)-4,4,4-trifluoro-2-buten-1-one

Example 3-1-1

1.07 g of 4-bromo-3-methylacetophenone, 1.22 g of 3',5'-dichloro-2,2,2-trifluoroacetophenone, 5 ml of toluene and 0.69 g of potassium carbonate were fed and the mixture was refluxed by heating for 21 hours. The mixture was cooled to room temperature, and separated by adding iced water. The solvent was distilled off under reduced pressure, and the residue was purified by silica gel column chromatography (eluent is a mixed liquid of hexane:ethyl acetate=10:1) to obtain 1.72 g of 1-(4-bromo-3-methylphenyl)-3-(3,5-dichlorophenyl)-4,4,4-trifluoro-2-buten-1-one as a red solid.

Example 3-1-2

3.0 g of 4-chloro-3-methylacetophenone, 4.35 g of 3',5'-dichloro-2,2,2-trifluoroacetophenone, 30 ml of 1,2-dichloroethane, 2.46 g of potassium carbonate and 0.18 g of triethylamine were fed and the mixture was refluxed by heating for 16 hours. The reaction solution was cooled to room temperature, and separated by adding 200 ml of ethyl acetate and iced water. The organic phase was washed with diluted hydrochloric acid and saturated saline, and dried over anhydrous sodium sulfate. The solvent was distilled off under reduced pressure. The residue was purified by silica gel column chromatography (eluent is a mixed liquid of hexane:ethyl acetate=9:1) to obtain 6.2 g of 1-(4-chloro-3-methylphenyl)-3-(3,5-dichlorophenyl)-4,4,4-trifluoro-2-buten-1-one as brown liquid.

Example 3-1-3

2.13 g of 4-bromo-3-methylacetophenone, 2.43 g of 3',5'-dichloro-2,2,2-trifluoroacetophenone, 2.43 g of toluene and 0.15 g of 1,8-diazabicyclo (5,4,0)-7-undecene were fed and the mixture was refluxed by heating for 10 hours. The mixture was cooled to room temperature, and separated by adding 20 ml of toluene, iced water and 0.3 ml of concentrated hydrochloric acid. The solvent was distilled off under reduced pressure, and the residue was purified by silica gel column chromatography (eluent is a mixed liquid of hexane:ethyl acetate=10:1) to obtain 3.95 g of 1-(4-bromo-3-methylphenyl)-3-(3,5-dichlorophenyl)-4,4,4-trifluoro-2-buten-1-one as a brown solid.

Example 3-1-4

0.46 g of 4-bromo-3-methylacetophenone, 0.49 g of 3',5'-dichloro-2,2,2-trifluoroacetophenone, 1.85 g of toluene, 1.85 g of n-tributylamine and 24 mg of 4-dimethylaminopyridine were fed and the mixture was stirred for 10 hours at 30° C. Then, 0.68 g of benzoic anhydride was added, and the mixture was stirred for 36 hours at room temperature. 0.11 g of benzoic anhydride was added, and further stirred for 16 hours. 2.7 g of iced water and 0.3 g of sodium hydroxide were added, and separated. The water phase was extracted twice with 3 ml of toluene. The resultant solution was combined with an organic phase and was washed with water and the solvent was distilled off under reduced pressure. 0.91 g of 1-(4-bromo-3-methylphenyl)-3-(3,5-dichlorophenyl)-4,4,4-trifluoro-2-buten-1-one was obtained as a yellow solid.

Example 3-2

One-Pot Synthesis of 1-(4-chloro-3-methylphenyl)-3-(3,5-dichlorophenyl)-4,4,4-trifluoro-2-buten-1-one 3.0 g of 4-chloro-3-methylacetophenone, 4.35 g of 3',5'-dichloro-2,2,2-trifluoroacetophenone, 30 ml of 1,2-dichloroethane, 2.46 g of potassium carbonate and 0.18 g of triethylamine were fed and the mixture was refluxed by heating for 16 hours. The reaction solution was cooled to room temperature, and separated by adding 200 ml of ethyl acetate and iced water. The organic phase was washed with diluted hydrochloric acid and saturated saline, and dried over anhydrous sodium sulfate. The solvent was distilled off under reduced pressure. The residue was purified by silica gel column chromatography (eluent is a mixed liquid of hexane:ethyl acetate=9:1) to obtain 6.2 g of 1-(4-chloro-3-methylphenyl)-3-(3,5-dichlorophenyl)-4,4,4-trifluoro-2-buten-1-one as brown liquid.

Synthesis Example of Raw Material 4

1-(4-bromo-3-methylphenyl)-3-(3,5-dichlorophenyl)-3-hydroxy-4,4,4-trifluorobutan-1-one Step 1: Synthesis of methyl 3,5-dichlorobenzoate 10 g of concentrated sulfuric acid was added to a methanol (120 g) solution of 50 g of 3,5-dichlorobenzoic acid, and the mixture was refluxed by heating for 5 hours. After cooling the reaction solution to room temperature, the solvent was distilled off under reduced pressure. The obtained residue was dissolved into 200 g of ethyl acetate, washed with water (200 g×2), then washed with a saturated aqueous solution of sodium bicarbonate, and further washed with water. After drying the organic phase over anhydrous magnesium sulfate, 48.6 g of the target product was obtained as a white solid by removing the solvent by distilling under reduced pressure.

$^1$H-NMR (CDCl$_3$, Me$_4$Si, 300 MHz) δ 7.90 (s, 2H), 7.54 (s, 1H), 3.94 (s, 3H).

Step 2: Synthesis of 3',5'-dichloro-2,2,2-trifluoroacetophenone

After adding 0.37 g of cesium fluoride to dimethoxyethane (300 g) solution of 25 g of methyl 3,5-dichlorobenzoate and 22.5 g of trifluoromethyltrimethylsilane under ice cooling, the mixture was warmed to room temperature and stirred for 4 hours. After confirming disappearance of the raw materials, 200 g of water was added to the reaction solution, and the mixture was extracted with 200 g of ethyl acetate. After dehydration/drying of the organic phase with saturated saline and then over anhydrous magnesium sulfate in this order, the solvent was distilled off under reduced pressure to obtain 35.5 g of 1-(3,5-dichlorophenyl)-2,2,2-trifluoro-1-trimethylsilyloxy-1-methoxyethane as crude yellow liquid. The obtained crude product was dissolved into 100 ml of tetrahydrofuran, and 9.75 ml of 1 M tetrahydrofuran solution of tetrabutylammonium fluoride was added in dropwise at room temperature. The mixture was stirred for 2 hours at the same temperature. After completion of the reaction, the solvent was distilled off under reduced pressure and the obtained residue was dissolved into ethyl acetate. After washing the organic phase with water and drying over anhydrous magnesium sulfate, the solvent was distilled off under reduced pressure. 24.2 g of the target product as colorless liquid was obtained by purifying the obtained residue by distilling under reduced pressure.

Boiling point 87° C. (1.7 kPa) $^1$H-NMR (CDCl$_3$, Me$_4$Si, 300 MHz) δ 7.92-7.93 (m, 2H), 7.70-7.71 (m, 1H).

Step 3: Synthesis of 1-(4-bromo-3-methylphenyl)-3-(3,5-dichlorophenyl)-3-hydroxy-4,4,4-trifluorobutan-1-one Tetrahydrofuran (40 ml) solution of 7.0 g of 4-bromo-3-methylacetophenone which can be synthesized in accordance with the method described in WO 96/19477 pamphlet, was cooled with dry ice-acetone to −60° C., and 32.8 ml of 1 M tetrahydrofuran solution of lithium bis(trimethylsilyl)amide was added in dropwise over 30 minutes. After adding in dropwise, the mixture was stirred for 1 hour at the same temperature. Then, tetrahydrofuran (15 ml) solution of 7.98 g of 3',5'-dichloro-2,2,2-trifluoroacetophenone was added in dropwise. The reaction solution was slowly warmed to room temperature, and stirred for 3 hours at room temperature. After completion of the reaction, 2N hydrochloric acid was added to the reaction solution, and the solvent was distilled off under reduced pressure. The obtained residue was dissolved into ethyl acetate and the solution was washed with water. After drying the organic phase over anhydrous magnesium sulfate, the solvent was distilled off under reduced pressure. 9.19 g of the target product was obtained as a white solid by washing the obtained solid with diisopropyl ether.

Melting point 141 to 142° C. $^1$H-NMR (CDCl$_3$, Me$_4$Si, 300 MHz) δ 7.77 (d, J=2.1 Hz, 1H), 7.68 (d, J=8.4 Hz, 1H), 7.48 (dd, J=8.4, 2.1 Hz, 1H), 7.49 (brs, 2H), 7.34 (brs, 1H), 5.72 (s, 1H), 3.81 (d, J=17.4 Hz, 1H), 3.63 (d, J=17.4 Hz, 1H), 2.48 (s, 3H).

Step 4: Synthesis of 1-(4-bromo-3-methylphenyl)-3-(3,5-dichlorophenyl)-4,4,4-trifluoro-2-buten-1-one 0.391 g of thionyl chloride and 0.104 g of pyridine were added to toluene (3 g) solution of 0.3 g of 1-(4-bromo-3-methylphenyl)-3-(3,5-dichlorophenyl)-3-hydroxy-4,4,4-trifluorobutan-1-one synthesized in Step 3 at room temperature and stirred for 1 hour at 80° C. After completion of the reaction, the reaction solution was cooled to room temperature, and separated by adding toluene and 2N hydrochloric acid. The organic phase was washed with water, and dried over anhydrous magnesium sulfate. The solvent was distilled off under reduced pressure. Although the obtained residue includes a mixture of geometric isomers, this residue was purified by silica gel column chromatography which eluted the residue with ethyl acetate-hexane (1:10) to obtain 0.244 g of the target product as a yellow solid.

Synthesis Example of Raw Material 5

Methyl 4-(3-(3,5-dichlorophenyl)-4,4,4-trifluoro-2-butenoyl) benzoate 1.98 g of bromine was added to chloroform (50 ml) solution of 2.0 g of methyl 4-acetyl-2-benzoate at room temperature, and stirred for 30 minutes. Then, the solvent was distilled off under reduced pressure. The obtained residue was dissolved into 40 ml of tetrahydrofuran, and 2.94 g of triphenylphosphine was added to the solution.

After stirring the solution for 30 minutes at 50° C., the solvent was distilled off under reduced pressure. The obtained residue was dissolved into 50 ml of chloroform, and 2.72 g of 3',5'-dichloro-2,2,2-trifluoroacetophenone which was synthesized in Step 2 in Synthesis Example 1, and 1.4 g of triethylamine were added to the solution. The solution was stirred for 4 hours at room temperature. Then, the reaction solution was washed with water (50 ml), and the organic phase was dried over anhydrous sodium sulfate. The solvent was distilled off under reduced pressure. The obtained residue was purified by silica gel column chromatography which eluted the residue with ethyl acetate-hexane (1:9), to obtain 1.0 g of the target product as a light yellow solid.

Here, the target product isolated in this Synthesis Example is a mixture of geometric isomers whose ratio determined by $^1$H-NMR was 19 to 1.

Melting point 65.5 to 67.5° C. $^1$H-NMR (CDCl$_3$, Me$_4$Si, 300 MHz) only main component δ 8.11 (d, J=8.4 Hz, 2H), 7.87 (d, J=8.4 Hz, 2H), 7.30-7.42 (m, 2H), 7.15 (d, J=1.8 Hz, 2H), 3.95 (s, 3H).

Synthesis Example of Raw Material 6

4-(3-(3,5-dichlorophenyl)-4,4,4-trifluoro-2-butenoyl) benzoic Acid

After adding 51 mg of 1,1'-bis(diphenylphosphino)ferrocene and 10 mg of palladium (II) acetate to tertiary-butyl alcohol (10 ml), dioxane (10 ml) and water (5 ml) solution of 1.95 g of 1-(4-bromophenyl)-3-(3,5-dichlorophenyl)-4,4,4-trifluoro-2-buten-1-one which was synthesized in accordance with Synthesis Example of Raw Material 5, and 0.56 g of triethylamine in an autoclave, and stirring for 4 hours at 110° C. under 0.5 MPa of carbon monoxide atmosphere, the mixture was left to cool to room temperature. 10 mg of palladium (II) acetate was further added and the mixture was stirred for 4 hours at 110° C. under 0.5 MPa of carbon monoxide atmosphere. Then, the mixture was left to cool to room temperature, and the solid was filtered. Diluted hydrochloric acid was added, and the mixture was extracted with ethyl acetate. The organic phase was dried over anhydrous sodium sulfate, and the solvent was distilled off under reduced pressure. The obtained residue was purified by silica gel column chromatography which eluted the residue with ethyl acetate-hexane (1:8), to obtain 1.56 g of the target product as a resinous solid.

$^1$H-NMR (CDCl$_3$, Me$_4$Si, 300 MHz) δ 8.18 (d, J=8.5 Hz, 2H), 7.91 (d, J=8.5 Hz, 2H), 7.40 (s, 1H), 7.34 (s, 1H), 7.16 (s, 2H).

Synthesis Example of Raw Material 7

4-(3-(3,5-dichlorophenyl)-4,4,4-trifluoro-2-butenoyl)-2-methylbenzoic Acid 0.25 g of 1,1'-bis(diphenylphosphino)ferrocene and 50 mg of palladium (II) acetate were added to 1,2-dimethoxyethene (20 ml) and water (20 ml) solution of 4.85 g of 1-(4-bromo-3-methylphenyl)-3-(3,5-dichlorophenyl)-4,4,4-trifluoro-2-buten-1-one which was synthesized in accordance with Step 4 in Synthesis Example of Raw Material 5, and 1.36 g of sodium acetate in an autoclave, and stirred for 5.5 hours at 110° C. under 1.0 MPa of carbon monoxide atmosphere. Then, the mixture was left to cool to room temperature, and the solid was filtered. Diluted hydrochloric acid was added to the solid, and the mixture was extracted with ethyl acetate. The organic phase was dehydrated/dried with saturated saline and then over anhydrous magnesium sulfate in this order, and the solvent was distilled off under reduced pressure. The obtained residue was purified by silica gel column chromatography which eluted the residue with ethyl acetate-hexane (1:5), and then crystallized from mixed solvent of hexane and small amount of ethyl acetate to obtain 2.6 g of the target product as a white solid.

Here, the target product isolated in this Synthesis Example is a mixture of geometric isomers whose ratio determined by $^1$H-NMR was 10 to 1.

Melting point 123.0 to 126.5° C. $^1$H-NMR (CDCl$_3$, Me$_4$Si, 300 MHz) only main component δ 8.11 (d, J=8.7 Hz, 1H), 7.65-7.70 (m, 2H), 7.30-7.40 (m, 2H), 7.16 (d, J=1.8 Hz, 2H), 2.69 (s, 3H).

Example 4-1

Synthesis of 3-(4-bromo-3-methylphenyl)-5-(3,5-dichlorophenyl)-5-trifluoromethyl-4,5-dihydroisoxazole Example 4-1-1

0.43 g (1.0 mmol) of 1-(4-bromo-3-methylphenyl)-3-(3,5-dichlorophenyl)-4,4,4-trifluoro-2-buten-1-one was dissolved into 2.2 g of toluene, and 1.0 g of dimethylsulfoxide was added. The mixture was stirred at 20° C. A solution which was prepared separately by mixing 0.16 g (4.0 mmol) of sodium hydroxide, 0.5 g of purified water and 0.164 g (1.0 mmol) of sulfuric acid salt of hydroxylamine was added in dropwise to this mixture.

Several drops of the reaction solution were poured into 0.5 mL of purified water. The mixture was diluted with 2 mL of acetonitrile, and analyzed by high-performance liquid chromatography. A percentage of the area of 3-(4-bromo-3-methylphenyl)-5-(3,5-dichlorophenyl)-5-trifluoromethyl-4,5-dihydroisoxazole determined by high-performance liquid chromatography after 1 hour was 95.6% (detected by UV detector at a wavelength of 220 nm, and calculated with omitting the peak of toluene).

Example 4-1-2

0.43 g (1.0 mmol) of 1-(4-bromo-3-methylphenyl)-3-(3,5-dichlorophenyl)-4,4,4-trifluoro-2-buten-1-one was dissolved into 2.2 g of toluene, and 1.0 g of methanol was added. The mixture was stirred at 20° C. A solution which was prepared separately by mixing 0.16 g (4.0 mmol) of sodium hydroxide, 0.5 g of purified water and 0.164 g (1.0 mmol) of sulfuric acid salt of hydroxylamine was added in dropwise to this mixture.

Several drops of the reaction solution were poured into 0.5 mL of purified water. The mixture was diluted with 2 mL of acetonitrile, and analyzed by high-performance liquid chromatography. A percentage of the area of 3-(4-bromo-3-methylphenyl)-5-(3,5-dichlorophenyl)-5-trifluoromethyl-4,5-dihydroisoxazole determined by high-performance liquid chromatography after 6 hours was 87.7% (detected by UV detector at a wavelength of 220 nm, and calculated with omitting the peak of toluene).

Example 4-1-3

0.43 g (1.0 mmol) of 1-(4-bromo-3-methylphenyl)-3-(3,5-dichlorophenyl)-4,4,4-trifluoro-2-buten-1-one was dissolved into 2.2 g of toluene, and the mixture was stirred at 15° C. 0.88 g (2.2 mmol of NaOH) of methanol solution of 10% sodium hydroxide and 0.132 g (2.0 mmol) of 50% aqueous solution of hydroxylamine which were prepared separately, were added in dropwise to this mixture.

Several drops of the reaction solution were poured into 0.5 mL of purified water. The mixture was diluted with 2 mL of acetonitrile, and analyzed by high-performance liquid chromatography. A percentage of the area of 3-(4-bromo-3-methylphenyl)-5-(3,5-dichlorophenyl)-5-trifluoromethyl-4,5-dihydroisoxazole determined by high-performance liquid chromatography after 1 hour was 90.8% (detected by UV detector at a wavelength of 220 nm, and calculated with omitting the peak of toluene).

Example 4-1-4

0.43 g (1.0 mmol) of 1-(4-bromo-3-methylphenyl)-3-(3,5-dichlorophenyl)-4,4,4-trifluoro-2-buten-1-one was dissolved into 2.2 g of toluene, and the mixture was stirred at 15° C. A solution which was diluted separately by adding 0.5 g of methanol to 0.3857 g (2.0 mmol of NaOMe) of 28% methanol solution of sodium methoxide and 0.132 g (2.0 mmol) of 50% aqueous solution of hydroxylamine were added in dropwise to this mixture.

Several drops of the reaction solution were poured into 0.5 mL of purified water. The mixture was diluted with 2 mL of acetonitrile, and analyzed by high-performance liquid chromatography. A percentage of the area of 3-(4-bromo-3-methylphenyl)-5-(3,5-dichlorophenyl)-5-trifluoromethyl-4,5-dihydroisoxazole determined by high-performance liquid chromatography after 1 hour was 92.3% (detected by UV detector at a wavelength of 220 nm, and calculated with omitting the peak of toluene).

Example 4-1-5

0.43 g (1.0 mmol) of 1-(4-bromo-3-methylphenyl)-3-(3,5-dichlorophenyl)-4,4,4-trifluoro-2-buten-1-one was dissolved into 2.2 g of toluene, and 0.0966 g (0.3 mmol) of tetrabutylammonium bromide was added. The mixture was stirred at 0° C. A solution which was prepared separately by mixing 0.088 g (2.2 mmol) of sodium hydroxide, 0.5 g of purified water and 0.132 g (2.0 mmol) of 50% aqueous solution of hydroxylamine was added in dropwise to this mixture.

Several drops of the reaction solution were poured into 0.5 mL of purified water. The mixture was diluted with 2 mL of acetonitrile, and analyzed by high-performance liquid chromatography. A percentage of the area of 3-(4-bromo-3-methylphenyl)-5-(3,5-dichlorophenyl)-5-trifluoromethyl-4,5-dihydroisoxazole determined by high-performance liquid chromatography after 3 hours was 98.6% (detected by UV detector at a wavelength of 220 nm, and calculated with omitting the peak of toluene). In addition, whole reaction solution after 4 hours was analyzed by high performance liquid chromatography using an internal standard method. The yield of 3-(4-bromo-3-methylphenyl)-5-(3,5-dichlorophenyl)-5-trifluoromethyl-4,5-dihydroisoxazole was 99.3%. (Internal standard method: Solutions varying compositions of the previously isolated target product and a standard substance being standard for peak area are prepared. The analytical curve is prepared from peak area ratios and weight ratios of the target product and the standard substance by measuring detection intensity of liquid chromatography analysis. Then, a constant amount of the standard substance is precisely added to a constant amount or a whole amount of the reaction solution after completion of the reaction, and liquid chromatography analysis is performed. This method is a method of calculating a concentration of the target product form the obtained area ratio of peak of the target product and peak of the standard substance by using the analytical curve. Here, p-Terphenyl was used as the standard substance.)

Example 4-1-6

2.190 g (5.0 mmol) of 1-(4-bromo-3-methylphenyl)-3-(3,5-dichlorophenyl)-4,4,4-trifluoro-2-buten-1-one was dissolved into 10.95 g of toluene, and 4.38 g of dimethylsulfoxide was added. The mixture was stirred at 15° C. A solution which was prepared separately by mixing 0.80 g (20.0 mmol) of sodium hydroxide, 2.5 g of purified water and 0.82 g (5.0 mmol) of sulfuric acid salt of hydroxylamine was added in dropwise to this mixture.

6 hours later, a diluted aqueous solution of hydrochloric acid prepared by mixing 1.5 mL of 35% hydrochloric acid and 8.76 g of purified water was added to the reaction solution, and 11 mL of toluene was added to separate. 7 g of purified water was added to the organic phase. The mixture was separated and the organic phase was dried over anhydrous sodium sulfate. Toluene was distilled off under reduced pressure. 2.264 g of a solid was obtained. The solid was identified as 3-(4-bromo-3-methylphenyl)-5-(3,5-dichlorophenyl)-5-trifluoromethyl-4,5-dihydroisoxazole by $^1$H-NMR, and the yield was 99%.

Example 4-1-7

2.1941 g (5.0 mmol) of 1-(4-bromo-3-methylphenyl)-3-(3,5-dichlorophenyl)-4,4,4-trifluoro-2-buten-1-one was dissolved into 10.95 g of toluene, and 0.32 g (1.0 mmol) of tetrabutylammonium bromide was added. The mixture was stirred under cooling with ice. A solution which was prepared separately by mixing 0.44 g (11.0 mmol) of sodium hydroxide, 2.2 g of purified water and 0.672 g (10.0 mmol) of 50% aqueous solution of hydroxylamine was added in dropwise to this mixture. 7 hours later, 0.15 g (0.5 mmol) of tetrabutylammonium bromide was further added, and then stirred for 14 hours at room temperature.

22 hours later in total, diluted aqueous solution of hydrochloric acid prepared by mixing 2.5 mL of 35% hydrochloric acid and 7.5 g of purified water was added to the reaction solution, and 4 mL toluene was added to separate. 4 g of purified water was added to the organic phase, and the mixture was separated. Two water phases were combined, and extracted again with 5 mL of toluene. The organic phase was combined with the previously obtained organic phase, and dried over anhydrous sodium sulfate. Toluene was distilled off under reduced pressure. 2.262 g of a solid was obtained. The solid was identified as 3-(4-bromo-3-methylphenyl)-5-(3,5-dichlorophenyl)-5-trifluoromethyl-4,5-dihydroisoxazole by $^1$H-NMR, and the yield was 99.8%. The melting point was 108 to 110° C.

Example 4-2

Synthesis of 3-(4-chloro-3-methylphenyl)-5-(3,5-dichlorophenyl)-5-trifluoromethyl-4,5-dihydroisoxazole 0.55 g of toluene and 0.027 g (0.085 mmol) of tetrabutylammonium bromide were added to 0.110 g (0.28 mmol) of 1-(4-chloro-3-methylphenyl)-3-(3,5-dichlorophenyl)-4,4,4-trifluoro-2-buten-1-one, and the mixture was stirred at 0°

C. A solution which was prepared separately by mixing 0.025 g (0.61 mmol) of sodium hydroxide, 0.17 g of purified water and 0.037 g (0.56 mmol) of 50% aqueous solution of hydroxylamine was added in dropwise to this mixture.

A small amount of the reaction solution was taken, diluted to 1 mL with acetonitrile, and analyzed by high-performance liquid chromatography. A percentage of the area of 3-(4-chloro-3-methylphenyl)-5-(3,5-dichlorophenyl)-5-trifluoromethyl-4,5-dihydroisoxazole determined by high-performance liquid chromatography after 7.5 hours was 88.4% (detected by UV detector at a wavelength of 225 nm, and calculated with omitting the peak of toluene). The reaction temperature was set back to room temperature again, and the reaction was performed for 15 hours. The reaction was traced by high-performance liquid chromatography in the same method as described above, and disappearance of the raw materials was confirmed. 0.70 g (1.68 mmol) of 8.8% hydrochloric acid and 5 mL of toluene were added to the reaction solution and separation operation was performed. The toluene phase was washed with 1 mL of purified water, and the water phase was extracted again with 5 mL of toluene. After combining toluene phases and drying over sodium sulfate, the solvent was distilled off using a rotary evaporator to obtain 0.108 g of 3-(4-chloro-3-methylphenyl)-5-(3,5-dichlorophenyl)-5-trifluoromethyl-4,5-dihydroisoxazole (yield 95%). The melting point was 110 to 111° C.

Example 4-3

Synthesis of 4-(5-(3,5-dichlorophenyl)-5-trifluoromethyl-4,5-dihydroisoxazol-3-yl)-2-methylbenzoic Acid Example 4-3-1

0.55 g of toluene and 0.026 g (0.082 mmol) of tetrabutylammonium bromide were added to 0.110 g (0.27 mmol) of 4-(3-(3,5-dichlorophenyl)-4,4,4-trifluoro-2-butenoyl)-2-methylbenzoic acid, and the mixture was stirred at 0° C. A solution which was prepared separately by mixing 0.024 g (0.60 mmol) of sodium hydroxide, 0.17 g of purified water and 0.036 g (0.55 mmol) of 50% aqueous solution of hydroxylamine was added in dropwise to this mixture.

A small amount of the reaction solution was taken, diluted to 1 mL with acetonitrile, and analyzed by high-performance liquid chromatography. Disappearance of the raw materials was confirmed by high-performance liquid chromatography analysis after 2.5 hours. 0.68 g (1.64 mmol) of 8.8% hydrochloric acid and 5 mL of ethyl acetate were added to the reaction solution and separation operation was performed. The ethyl acetate phase was washed with 1 mL of purified water, and the water phase was extracted again with 5 mL of ethyl acetate. After combining ethyl acetate phases and drying over sodium sulfate, the solvent was distilled off using a rotary evaporator to obtain 0.111 g of 4-(5-(3,5-dichlorophenyl)-5-trifluoromethyl-4,5-dihydroisoxazol-3-yl)-2-methylbenzoic acid (yield 97%).

Example 4-3-2

3.2 g of dimethylformamide was added to solution in which 1.61 g of 4-(3-(3,5-dichlorophenyl)-4,4,4-trifluoro-2-butenoyl)-2-methylbenzoic acid was dissolved into 8.51 g of toluene, and the mixture was cooled to 0° C. A solution in which 0.64 g of sodium hydroxide was dissolved into 1.6 g of water was added to the mixture, and a solution in which 0.46 g of hydroxylamine sulfate dissolved into 1.11 g of water was slowly added in dropwise with care not to generate heat. After reacting the mixture for 3 hours with stirring while keeping the reaction temperature at 0° C., the resultant solution was analyzed by high-performance liquid chromatography (wavelength 254 nm). The target product of 4-(5-(3,5-dichlorophenyl)-5-trifluoromethyl-4,5-dihydroisoxazol-3-yl)-2-methylbenzoic acid was produced in 90.49% of relative area.

Example 4-3-3

6.27 g of dimethylsulfoxide was added to solution in which 1.61 g of 4-(3-(3,5-dichlorophenyl)-4,4,4-trifluoro-2-butenoyl)-2-methylbenzoic acid was dissolved into 10.5 g of toluene, and the mixture was cooled to 0° C. A solution in which 0.64 g of sodium hydroxide was dissolved into 1.6 g of water was carefully added to the mixtures so that the temperature of the reaction solution did not exceed 5° C. Moreover, a solution in which 0.46 g of hydroxylamine sulfate was dissolved into 2.24 g of water was carefully added to the mixtures so that the temperature of the reaction solution did not exceed 5° C. The reaction was performed for 1 hour with stirring while keeping the reaction temperature at 0° C. The reaction solution was analyzed by high-performance liquid chromatography (detected by UV detector at a wavelength of 254 nm, and calculated with omitting the peak of toluene). The target product of 4-(5-(3,5-dichlorophenyl)-5-trifluoromethyl-4,5-dihydroisoxazol-3-yl)-2-methylbenzoic acid was produced in 85.0% of relative area.

Example 4-3-4

6.27 g of N-methylpyrrolidone was added to solution in which 1.61 g of 4-(3-(3,5-dichlorophenyl)-4,4,4-trifluoro-2-butenoyl)-2-methylbenzoic acid was dissolved into 10.5 g of toluene, and the mixture was cooled to −25° C. A solution in which 0.64 g of sodium hydroxide was dissolved into 1.6 g of water was carefully added to the mixtures so that the temperature of the reaction solution did not exceed −20° C. Moreover, a solution in which 0.46 g of hydroxylamine sulfate was dissolved into 2.24 g of water was carefully added to the mixtures so that the temperature of the reaction solution did not exceed −20° C. The reaction was performed for 3 hours with stirring while keeping the reaction temperature at −25° C. 10.4 g of toluene and 1.9 ml of 35% hydrochloric acid was added to the reaction solution in dropwise at −25 to −10° C., and further stirred for 1 hour at room temperature. The reaction solution was separated and the water phase was extracted with 10.4 g of toluene. The organic phases were combined and washed with 5 ml of water. The obtained toluene was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 95.8%.

Example 4-3-5

6.27 g of 1,2-dimethoxyethane was added to solution in which 1.61 g of 4-(3-(3,5-dichlorophenyl)-4,4,4-trifluoro-2-butenoyl)-2-methylbenzoic acid was dissolved into 10.5 g of toluene, and the mixture was cooled to 0° C. A solution in which 0.64 g of sodium hydroxide was dissolved into 1.6 g of water was carefully added to the mixture so that the temperature of the reaction solution did not exceed 5° C. Moreover, a solution in which 0.46 g of hydroxylamine sulfate was dissolved into 2.24 g of water was carefully added to the mixture so that the temperature of the reaction solution did not exceed 5° C. The reaction was performed for 3 hours with stirring while keeping the reaction temperature at 0° C. The reaction solution was analyzed by high-performance liquid chromatography (detected by UV detector at a wavelength of 254 nm, and calculated with omitting the peak of toluene). The target product of 4-(5-(3,5-dichlorophenyl)-5-trifluoromethyl-4,5-dihydroisoxazol-3-yl)-2-methylbenzoic acid was produced in 88.4% of relative area.

Example 4-3-6

3.2 g of diglyme was added to a solution in which 1.61 g of 4-(3-(3,5-dichlorophenyl)-4,4,4-trifluoro-2-butenoyl)-2-methylbenzoic acid was dissolved into 8.51 g of toluene, and the mixture was cooled to 0° C. A solution in which 0.64 g of sodium hydroxide was dissolved into 1.6 g of water was added to the mixture, and a solution in which 0.46 g of hydroxylamine sulfate was dissolved into 1.11 g of water was slowly added in dropwise with care not to generate heat. After reacting the mixture for 1 hour with stirring while keeping the reaction temperature at 0° C., the resultant solution was analyzed by high-performance liquid chromatography (wavelength 254 nm). The target product of 4-(5-(3,5-dichlorophenyl)-5-trifluoromethyl-4,5-dihydroisoxazol-3-yl)-2-methylbenzoic acid was produced in 88.32% of relative area.

Example 4-3-7

3.2 g of methyl alcohol was added to a solution in which 1.61 g of 4-(3-(3,5-dichlorophenyl)-4,4,4-trifluoro-2-butenoyl)-2-methylbenzoic acid was dissolved into 8.51 g of toluene, and the mixture was cooled to 0° C. A solution in which 0.64 g of sodium hydroxide was dissolved into 1.6 g of water was added to the mixture, and a solution in which 0.46 g of hydroxylamine sulfate was dissolved into 1.11 g of water was slowly added in dropwise with care not to generate heat. After reacting the mixture for 3 hours with stirring while keeping the reaction temperature at 0° C., the resultant solution was analyzed by high-performance liquid chromatography (wavelength 254 nm). The target product of 4-(5-(3,5-dichlorophenyl)-5-trifluoromethyl-4,5-dihydroisoxazol-3-yl)-2-methylbenzoic acid was produced in 85.49% of relative area.

Example 4-3-8

6.72 g of N-methylpyrrolidone was added to a solution in which 1.73 g of 4-(3-(3,5-dichlorophenyl)-4,4,4-trifluoro-2-butenoyl)-2-methylbenzoic acid was dissolved into 11.2 g of toluene, and the mixture was cooled to 0° C. A solution in which 0.97 g of potassium hydroxide was dissolved into 1.7 g of water was carefully added to the mixture so that the temperature of the reaction solution did not exceed 5° C. Moreover, a solution in which 0.49 g of hydroxylamine sulfate was dissolved into 2.40 g of water was carefully added to the mixtures so that the temperature of the reaction solution did not exceed 5° C. The reaction was performed for 3 hours with stirring while keeping the reaction temperature at 0° C. 11.2 g of toluene and 2.1 ml of 35% hydrochloric acid was added to the reaction solution in dropwise at 0 to 5° C., and further stirred for 30 minutes at room temperature. The reaction solution was separate and the water phase was extracted with 12 g of toluene. The organic phases were combined and washed twice with 5 ml of water. The obtained toluene was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 88.2%.

Example 4-3-9

6.27 g of N-methyl-2-pyrrolidone was added to 11.85 g of toluene solution which dissolved 1.61 g (4.0 mmol) of 4-(3-(3,5-dichlorophenyl)-4,4,4-trifluoro-2-butenoyl)-2-methylbenzoic acid, and the mixture was cooled to −7° C. After adding 2.24 g (16 mmol) of an aqueous solution of sodium hydroxide prepared in 10 M in dropwise, and then adding an aqueous solution in which 0.306 g (4.4 mmol) of hydroxylamine hydrochloride was dissolved into 0.65 g of water in dropwise, the mixture was reacted at −7° C. A small amount of the reaction solution was taken, diluted to 1 mL with acetonitrile, and analyzed by high-performance liquid chromatography. A percentage of the area of 4-(5-(3,5-dichlorophenyl)-5-trifluoromethyl-4,5-dihydroisoxazol-3-yl)-2-methylbenzoic acid determined by high-performance liquid chromatography after 3 hours was 98.0% (detected by UV detector at a wavelength of 254 nm, and calculated with omitting the peak of toluene). 10.4 g of toluene was added to the reaction solution after 5 hours, and 1.9 mL of 35% hydrochloric acid was added in dropwise at 0° C., and further stirred for 1 hour. After stopping stirring, the water phase was removed. The obtained toluene solution was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 90.2%.

Example 4-3-10

6.27 g of N-methyl-2-pyrrolidone was added to 11.85 g of toluene solution which dissolved 1.61 g (4.0 mmol) of 4-(3-(3,5-dichlorophenyl)-4,4,4-trifluoro-2-butenoyl)-2-methylbenzoic acid, and the mixture was cooled to 0° C. After adding in dropwise a solution prepared by adding 1.6 g of water to 2.44 g (16 mmol) of 1,8-diazabicyclo (5,4,0)-7-undecene, and then adding an aqueous solution in which 0.306 g (4.4 mmol) of hydroxylamine hydrochloride was dissolved into 0.65 g of water in dropwise, the mixture was reacted at 0° C. A small amount of the reaction solution was taken, diluted to 1 mL with acetonitrile, and analyzed by high-performance liquid chromatography. A percentage of the area of 4-(5-(3,5-dichlorophenyl)-5-trifluoromethyl-4,5-dihydroisoxazol-3-yl)-2-methylbenzoic acid determined by high-performance liquid chromatography after 3 hours was 94.9% (detected by UV detector at a wavelength of 254 nm, and calculated with omitting the peak of toluene). 1.9 mL of 35% hydrochloric acid was added to the reaction solution after 3 hours in dropwise at 0° C., and stirred for 1 hour. After stopping stirring, the water phase was removed. The obtained toluene solution was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 92.2%.

Example 4-3-11

6.27 g of ethanol was added to 11.89 g of toluene solution which dissolved 1.61 g (4.0 mmol) of 4-(3-(3,5-dichlorophenyl)-4,4,4-trifluoro-2-butenoyl)-2-methylbenzoic acid, and the mixture was cooled to 0° C. After adding in dropwise a solution which was prepared by adding 1.6 g of water to 2.44 g (16 mmol) of 1,8-diazabicyclo (5,4,0)-7-undecene, then adding an aqueous solution in which 0.306 g (4.4 mmol) of hydroxylamine hydrochloride was dissolved into 0.65 g of water in dropwise, the mixture was reacted at 0° C. A small amount of the reaction solution was taken, diluted to 1 mL with acetonitrile, and analyzed by high-performance liquid chromatography. A percentage of the area of 4-(5-(3,5-dichlorophenyl)-5-trifluoromethyl-4,5-dihydroisoxazol-3-yl)-2-methylbenzoic acid determined by high-performance liquid chromatography after 1 hour was 94.5% (detected by UV detector at a wavelength of 254 nm, and calculated with omitting the peak of toluene). 1.9 mL of 35% hydrochloric acid was added to the reaction solution after 3 hours in dropwise at 0° C., and stirred for 1 hour. After stopping stirring, the water phase was removed. The obtained toluene solution was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 90.4%.

Example 4-3-12

6.27 g of tetrahydrofuran was added to 11.89 g of toluene solution which dissolved 1.61 g (4.0 mmol) of 4-(3-(3,5-dichlorophenyl)-4,4,4-trifluoro-2-butenoyl)-2-methylbenzoic acid, and the mixture was cooled to 0° C. After adding in dropwise a solution which was prepared by adding 1.6 g of water to 2.44 g (16 mmol) of 1,8-diazabicyclo (5,4,0)-7-undecene, then adding an aqueous solution in which 0.306 g (4.4 mmol) of hydroxylamine hydrochloride was dissolved into 0.65 g of water in dropwise, the mixture was reacted at 0° C. A small amount of the reaction solution was taken, diluted to 1 mL with acetonitrile, and analyzed by high-performance liquid chromatography. A percentage of the area of 4-(5-(3,5-dichlorophenyl)-5-trifluoromethyl-4,5-dihydroisoxazol-3-yl)-2-methylbenzoic acid determined by high-performance liquid chromatography after 3-hour-reaction was 94.0% (detected by UV detector at a wavelength of 254 nm, and calculated with omitting the peak of toluene). 1.9 mL of 35% hydrochloric acid was added to the reaction solution after 3 hours in dropwise at 0° C., and stirred for 1 hour. After stopping stirring, the water phase was removed. The obtained toluene solution was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 95.2%.

Example 4-3-13

A solution in which 2.02 g of 4-(3-(3,5-dichlorophenyl)-4,4,4-trifluoro-2-butenoyl)-2-methylbenzoic acid was dissolved into 10.1 g of toluene was cooled to 0° C. 2.28 g of 1,8-diazabicyclo (5,4,0)-7-undecene was carefully added to the solution so that the temperature of the reaction solution did not exceed 5° C. Moreover, a solution in which 0.38 g of hydroxylamine hydrochloride was dissolved into 0.81 g of water was carefully added to the mixture so that the temperature of the reaction solution did not exceed 5° C. The reaction was performed for 2 hours with stirring while keeping the reaction temperature at 0° C. 2.0 ml of 35% hydrochloric acid was added to the reaction solution in dropwise at 10° C. or lower, and 10 g of toluene was further added and stirred at room temperature. The reaction solution was separated and the organic phase was washed twice with 5 ml of water. The obtained toluene was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 90.4%.

Example 4-3-14

The solution in which 2.02 g of 4-(3-(3,5-dichlorophenyl)-4,4,4-trifluoro-2-butenoyl)-2-methylbenzoic acid was dissolved into 10.1 g of toluene was cooled to 0° C. 1.52 g of 1,8-diazabicyclo (5,4,0)-7-undecene was carefully added to the solution so that the temperature of the reaction solution did not exceed 5° C. Moreover, the solution in which 0.20 g of sodium hydroxide was dissolved into 1.0 g of water was carefully added to the mixture so that the temperature of the reaction solution did not exceed 5° C. Then, the solution in which 0.38 g of hydroxylamine hydrochloride was dissolved into 0.81 g of water was carefully added to the mixture so that the temperature of the reaction solution did not exceed 5° C. The reaction was performed for 2 hours with stirring while keeping the reaction temperature at 0° C. 2.0 ml of 35% hydrochloric acid was added to the reaction solution in dropwise at 10° C. or lower, and 10 g of toluene was further added and stirred at room temperature. The reaction solution was separated and the organic phase was washed twice with 5 ml of water. The obtained toluene was analyzed by high-performance liquid chromatography using the internal standard method. The yield of 4-(5-(3,5-dichlorophenyl)-5-trifluoromethyl-4,5-dihydroisoxazol-3-yl)-2-methylbenzoic acid was 92.8%.

Example 4-4

Synthesis of methyl 4-(5-(3,5-dichlorophenyl)-5-trifluoromethyl-4,5-dihydroisoxazol-3-yl) benzoate 0.55 g of toluene and 0.026 g (0.082 mmol) of tetrabutylammonium bromide was added to 0.110 g (0.27 mmol) of methyl 4-(3-(3,5-dichlorophenyl)-4,4,4-trifluoro-2-butenoyl) benzoate, and the mixture was stirred at 0° C. A solution which was prepared separately by mixing 0.024 g (0.60 mmol) of sodium hydroxide, 0.17 g of purified water and 0.036 g (0.55 mmol) of 50% aqueous solution of hydroxylamine was added in dropwise to this mixture.

A small amount of the reaction solution was taken, diluted to 1 mL with acetonitrile, and analyzed by high-performance liquid chromatography. Disappearance of the raw materials was confirmed by high-performance liquid chromatography analysis after 5.5 hours. 0.68 g (1.64 mmol) of 8.8% hydrochloric acid and 5 mL of toluene were added to the reaction solution and separation operation was performed. The toluene phase was washed with 1 mL of purified water, and the water phase was extracted again with 5 mL of toluene. After combining toluene phases and drying over sodium sulfate, the solvent was distilled off using a rotary evaporator to obtain 0.109 g of methyl 4-(5-(3,5-dichlorophenyl)-5-trifluoromethyl-4,5-dihydroisoxazol-3-yl) benzoate (yield 96%).

Example 4-5

Synthesis of N-(2-pyridylmethyl)-4-(5-(3,5-dichlorophenyl)-5-trifluoromethyl-4,5-dihydroisoxazol-3-yl)-2-methylbenzoic Acid Amide 0.55 g of toluene and 0.022 g (0.067 mmol) of tetrabutylammonium bromide were added to 0.110 g (0.22 mmol)

of N-(2-pyridylmethyl)-4-(3-(3,5-dichlorophenyl)-4,4,4-trifluoro-2-butenoyl)-2-methylbenzoic acid amide, and the mixture was stirred at 0° C. A solution which was prepared separately by mixing 0.020 g (0.49 mmol) of sodium hydroxide, 0.17 g of purified water and 0.029 g (0.45 mmol) of 50% aqueous solution of hydroxylamine was added in dropwise to this mixture.

A small amount of the reaction solution was taken, diluted to 1 mL with acetonitrile, and analyzed by high-performance liquid chromatography. A percentage of the area of N-(2-pyridylmethyl)-4-(5-(3,5-dichlorophenyl)-5-trifluoromethyl-4,5-dihydroisoxazol-3-yl)-2-methylbenzoic acid amide determined by high-performance liquid chromatography after 23 hours was 87.0% (detected by UV detector at a wavelength of 225 nm, and calculated with omitting the peak of toluene). The reaction temperature was set back to room temperature again, and the reaction was performed for 6 hours. The reaction was traced by high-performance liquid chromatography in the same method as described above, and disappearance of the raw materials was confirmed. 0.56 g (1.34 mmol) of 8.8% hydrochloric acid and 5 mL of chloroform were added to the reaction solution and separation operation was performed. The chloroform phase was washed with 1 mL of purified water, and the water phase was extracted again with 5 mL of chloroform. After combining chloroform phases and drying over sodium sulfate, the solvent was distilled off using a rotary evaporator to obtain 0.0836 g of N-(2-pyridylmethyl)-4-(5-(3,5-dichlorophenyl)-5-trifluoromethyl-4,5-dihydroisoxazol-3-yl)-2-methylbenzoic acid amide (yield 74%).

Example 4-6

Synthesis of 3-(4-bromo-3-methylphenyl)-5-(3,4,5-trichlorophenyl)-5-trifluoromethyl-4,5-dihydroisoxazole 0.29 g of toluene and 0.012 g (0.036 mmol) of tetrabutylammonium bromide were added to 0.057 g (0.12 mmol) of 1-(4-bromo-3-methylphenyl)-3-(3,4,5-trichlorophenyl)-4,4,4-trifluoro-2-buten-1-one, and the mixture was stirred at 0° C. A solution which was prepared separately by mixing 0.011 g (0.27 mmol) of sodium hydroxide, 0.09 g of purified water and 0.016 g (0.24 mmol) of 50% aqueous solution of hydroxylamine was added in dropwise to this mixture.

A small amount of the reaction solution was taken, diluted to 1 mL with acetonitrile, and analyzed by high-performance liquid chromatography. Disappearance of the raw materials was confirmed by high-performance liquid chromatography analysis after 23 hours. 0.30 g (0.73 mmol) of 8.8% hydrochloric acid and 5 mL of toluene were added to the reaction solution and separation operation was performed. The toluene phase was washed with 1 mL of purified water, and the water phase was extracted again with 5 mL of toluene. After combining toluene phases and drying over sodium sulfate, the solvent was distilled off using a rotary evaporator to obtain 0.061 g of 3-(4-bromo-3-methylphenyl)-5-(3,4,5-dichlorophenyl)-5-trifluoromethyl-4,5-dihydroisoxazole (yield 100%).
$^1$H-NMR (CDCl$_3$, Me$_4$Si, 300 MHz) δ 7.64 (s, 2H), 7.59 (d, 1=8.1 Hz, 1H), 7.53 (d, J=2.1 Hz, 1H), 7.32 (dd, J=8.1, 2.1 Hz, 1H), 4.07 (d, J=17.4 Hz, 1H), 3.66 (d, J=17.4 Hz, 1H), 2.43 (s, 3H).

Example 4-7

Synthesis of 4-(5-(3,5-dichlorophenyl)-5-trifluoromethyl-4,5-dihydroisoxazol-3-yl) benzoic Acid 1.0 g of toluene and 0.050 g (0.15 mmol) of tetrabutylammonium bromide were added to 0.200 g (0.51 mmol) of methyl 4-(3-(3,5-dichlorophenyl)-4,4,4-trifluoro-2-butenoyl) benzoic acid, and the mixture was stirred at 0° C. A solution which was prepared separately by mixing 0.045 g (1.13 mmol) of sodium hydroxide, 0.30 g of purified water and 0.068 g (1.03 mmol) of 50% aqueous solution of hydroxylamine was added in dropwise to this mixture.

A small amount of the reaction solution was taken, diluted to 1 mL with acetonitrile, and analyzed by high-performance liquid chromatography. Disappearance of the raw materials was confirmed by high-performance liquid chromatography analysis after 6.5 hours. 1.29 g (3.09 mmol) of 8.8% hydrochloric acid and 5 mL of ethyl acetate were added to the reaction solution and separation operation was performed. The ethyl acetate phase was washed with 1 mL of purified water, and the water phase was extracted again with 5 mL of ethyl acetate. After combining ethyl acetate phases and drying over sodium sulfate, the solvent was distilled off using a rotary evaporator to obtain 0.210 g of 4-(5-(3,5-dichlorophenyl)-5-trifluoromethyl-4,5-dihydroisoxazol-3-yl) benzoic acid (yield 100%).

Example 4-8

Synthesis of 3-(4-bromo-3-methylphenyl)-5-(3-trifluoromethylphenyl)-5-trifluoromethyl-4,5-dihydroisoxazole 0.67 g of toluene and 0.030 g (0.092 mmol) of tetrabutylammonium bromide were added to 0.134 g (0.31 mmol) of 1-(4-bromo-3-methylphenyl)-3-(3-trifluoromethylphenyl)-4,4,4-trifluoro-2-buten-1-one, and the mixture was stirred at 0° C. A solution which was prepared separately by mixing 0.027 g (0.68 mmol) of sodium hydroxide, 0.20 g of purified water and 0.041 g (0.61 mmol) of 50% aqueous solution of hydroxylamine was added in dropwise to this mixture.

A small amount of the reaction solution was taken, diluted to 1 mL with acetonitrile, and analyzed by high-performance liquid chromatography. A percentage of the area of 3-(4-bromo-3-methylphenyl)-5-(3-trifluoromethylphenyl)-5-trifluoromethyl-4,5-dihydroisoxazole determined by high-performance liquid chromatography after 22 hours was 86.3% (detected by UV detector at a wavelength of 225 nm, and calculated with omitting the peak of toluene). The reaction temperature was set back to room temperature again, and the reaction was performed for 5.5 hours. The reaction was traced by high-performance liquid chromatography in the same method as described above, and disappearance of the raw materials was confirmed. 0.77 g (1.84 mmol) of 8.8% hydrochloric acid and 5 mL of ethyl acetate were added to the reaction solution and separation operation was performed. The ethyl acetate phase was washed with 1 mL of purified water, and the water phase was extracted again with 5 mL of ethyl acetate. After combining ethyl acetate phases and drying over sodium sulfate, the solvent was distilled off using a rotary evaporator to obtain 0.134 g of 3-(4-bromo-3-methylphenyl)-5-(3-trifluoromethylphenyl)-5-trifluoromethyl-4,5-dihydroisoxazole (yield 97%). The melting point was 84 to 85° C.

Example 4-9

Synthesis of 5-(3,5-bis(trifluoromethyl)phenyl)-3-(4-bromo-3-methylphenyl)-5-trifluoromethyl-4,5-dihydroisoxazole 0.38 g of toluene and 0.015 g (0.045 mmol) of tetrabutylammonium bromide were added to 0.075 g (0.15 mmol)

of 3-(3,5-bis(trifluoromethyl)phenyl-1-(4-bromo-3-methylphenyl)-4,4,4-trifluoro-2-buten-1-one, and the mixture was stirred at 0° C. A solution which was prepared separately by mixing 0.013 g (0.33 mmol) of sodium hydroxide, 0.11 g of purified water and 0.020 g (0.30 mmol) of 50% aqueous solution of hydroxylamine was added in dropwise to this mixture.

A small amount of the reaction solution was taken, diluted to 1 mL with acetonitrile, and analyzed by high-performance liquid chromatography. A percentage of the area of 5-(3,5-bis(trifluoromethyl)phenyl)-3-(4-bromo-3-methylphenyl)-5-trifluoromethyl-4,5-dihydroisoxazole determined by high-performance liquid chromatography after 22 hours was 94.8% (detected by UV detector at a wavelength of 225 nm, and calculated with omitting the peak of toluene). The reaction temperature was set back to room temperature again, and the reaction was performed for 5.5 hours. The reaction was traced by high-performance liquid chromatography in the same method as described above, and disappearance of the raw materials was confirmed. 0.38 g (0.90 mmol) of 8.8% hydrochloric acid and 5 mL of ethyl acetate were added to the reaction solution and separation operation was performed. The ethyl acetate phase was washed with 1 mL of purified water, and the water phase was extracted again with 5 mL of ethyl acetate. After combining ethyl acetate phases and drying over sodium sulfate, the solvent was distilled off using a rotary evaporator to obtain 0.074 g of 5-(3,5-bis(trifluoromethyl)phenyl)-3-(4-bromo-3-methylphenyl)-5-trifluoromethyl-4,5-dihydroisoxazole (yield 95%). The melting point was 108 to 110° C.

Example 4-10

Synthesis of 3-(4-bromo-3-methylphenyl)-5-(3,5-dichlorophenyl)-5-chlorodifluoromethyl-4,5-dihydroisoxazole 0.52 g of toluene and 0.022 g (0.068 mmol) of tetrabutylammonium bromide were added to 0.103 g (0.23 mmol) of 1-(4-chloro-3-methylphenyl)-3-(3,5-dichlorophenyl)-4-chloro-4,4-difluoro-2-buten-1-one, and the mixture was stirred at 0° C. A solution which was prepared separately by mixing 0.020 g (0.50 mmol) of sodium hydroxide, 0.16 g of purified water and 0.030 g (0.45 mmol) of 50% aqueous solution of hydroxylamine was added in dropwise to this mixture.

A small amount of the reaction solution was taken, diluted to 1 mL with acetonitrile, and analyzed by high-performance liquid chromatography. A percentage of the area of 3-(4-bromo-3-methylphenyl)-5-(3,5-dichlorophenyl)-5-chlorodifluoromethyl-4,5-dihydroisoxazole determined by high-performance liquid chromatography after 22 hours was 57.3% (detected by UV detector at a wavelength of 225 nm, and calculated with omitting the peak of toluene). The reaction temperature was set back to room temperature again, and the reaction was performed for 24 hours. The reaction was traced by high-performance liquid chromatography in the same method as described above. As a result, a percentage of the area of 3-(4-bromo-3-methylphenyl)-5-(3,5-dichlorophenyl)-5-chlorodifluoromethyl-4,5-dihydroisoxazole was 84.7% (detected by UV detector at a wavelength of 225 nm, and calculated with omitting the peak of toluene). Although the reaction solution was further stirred for 24 hours at room temperature, the percentage of the area was not changed. Therefore, the reaction was terminated, and 0.57 g (1.36 mmol) of 8.8% hydrochloric acid and 5 mL of toluene were added to the reaction solution and separation operation was performed. The toluene phase was washed with 1 mL of purified water, and the water phase was extracted again with 5 mL of toluene. After combining toluene phases and drying over sodium sulfate, the solvent was distilled off using a rotary evaporator. The residue was purified by column chromatography to obtain 0.223 g of 3-(4-bromo-3-methylphenyl)-5-(3,5-dichlorophenyl)-5-chlorodifluoromethyl-4,5-dihydroisoxazole (yield 21%).

$^1$H-NMR (CDCl$_3$, Me$_4$Si, 300 MHz) δ 7.58 (d, J=8.1 Hz, 1H), 7.52 (bs, 3H), 7.41 (m, 1H), 7.32 (dd, J=8.1, 2.1 Hz, 1H), 4.11 (d, J=17.4 Hz, 1H), 3.70 (d, J=17.4 Hz, 1H), 2.44 (s, 3H).

Example 4-11

Synthesis of 5-(3,5-bis(trifluoromethyl)phenyl)-3-(3-chloro-4-methylphenyl)-5-(trifluoromethyl)-4,5-dihydroisoxazole 0.550 g of toluene and 0.330 g of N-methyl-2-pyrrolidone were added to 0.110 g (0.24 mmol) of 3-(3,5-bis(trifluoromethyl)phenyl)-1-(3-chloro-4-methylphenyl)-4,4,4-trifluoro-2-buten-1-one, and the mixture was cooled to 0° C. After adding 0.134 g (0.96 mmol) of an aqueous solution of sodium hydroxide prepared in 10 M in dropwise, and then adding aqueous solution in which 0.018 g (0.26 mmol) of hydroxylamine hydrochloride was dissolved into 0.039 g of water in dropwise, the mixture was reacted at 0° C. A small amount of the reaction solution was taken, diluted to 1 mL with acetonitrile, and analyzed by high-performance liquid chromatography. A percentage of the area of 5-(3,5-bis(trifluoromethyl)phenyl)-3-(3-chloro-4-methylphenyl)-5-(trifluoromethyl)-4,5-dihydroisoxazole determined by high-performance liquid chromatography after 4 hours was 96.6% (detected by UV detector at a wavelength of 254 nm, and calculated with omitting the peak of toluene). The reaction temperature was set back to room temperature again, and the reaction was performed for 2 hours. The reaction was traced by high-performance liquid chromatography in the same method as described above, and disappearance of the raw materials was confirmed. 0.60 g (1.43 mmol) of 8.8% hydrochloric acid and 5 mL of toluene were added to the reaction solution and separation operation was performed. After washing the toluene phase thrice with 4 ml of purified water and drying over sodium sulfate, the solvent was distilled off using a rotary evaporator to obtain 0.109 g of 5-(3,5-bis(trifluoromethyl)phenyl)-3-(3-chloro-4-methylphenyl)-5-(trifluoromethyl)-4,5-dihydroisoxazole (yield 99%).

Example 4-12

Synthesis of 3-(4-(1H-1,2,4-triazol-1-yl)phenyl)-5-(3,5-dichlorophenyl)-5-(trifluoromethyl)-4,5-dihydroisoxazole 2.50 g of toluene and 1.50 g of N-methyl-2-pyrrolidone was added to 0.50 g (1.21 mmol) of 3-(4-(1H-1,2,4-triazol-1-yl)phenyl)-3-(3,5-dichlorophenyl)-4,4,4-trifluoro-2-buten-1-one, and the mixture was cooled to 0° C. After adding in dropwise to this mixture the solution which was prepared by adding 0.20 g of water to 0.19 g (4.84 mmol) of sodium hydroxide, and then adding the solution in which 0.093 g (1.33 mmol) of hydroxylamine hydrochloride was dissolved into 0.48 g of water in dropwise, the mixture was reacted for 2 hours. The aqueous solution which was prepared from 0.76 g (7.26 mmol) of 35% hydrochloric acid and 2.27 g of water was added in dropwise to the reaction solution, and the mixture was stirred for 1 hour. Separation operation was performed by adding 10 ml of ethyl acetate, and the ethyl acetate was washed twice with 5 ml of water.

The solvent was distilled off under reduced pressure to obtain 0.49 g of 3-(4-(1H-1,2,4-triazol-1-yl)phenyl)-5-(3,5-dichlorophenyl)-5-(trifluoromethyl)-4,5-dihydroisoxazole (yield 94.7%).

Melting point 179 to 181° C.

Example 4-13

Synthesis of 1-(4-(1H-imidazol-1-yl)phenyl)-5-(3,5-dichlorophenyl)-5-(trifluoromethyl)-4,5-dihydroisoxazole 2.00 g of toluene and 1.22 g of N-methyl-2-pyrrolidone was added to 0.41 g (0.99 mmol) of 3-(4-(1H-imidazol-1-yl)phenyl)-3-(3,5-dichlorophenyl)-4,4,4-trifluoro-2-buten-1-one, and the mixture was cooled to 0° C. After adding in dropwise to this mixture the solution which was prepared by adding 0.39 g of water to 0.16 g (3.94 mmol) of sodium hydroxide, and then adding the solution in which 0.075 g (1.08 mmol) of hydroxylamine hydrochloride was dissolved into 0.16 g of water in dropwise, the mixture was reacted for 3 hours at 0° C. The aqueous solution which was prepared from 0.62 g (5.91 mmol) of 35% hydrochloric acid and 1.85 g of water was added in dropwise to the reaction solution, and the mixture was stirred for 1 hour. Separation operation was performed by adding 30 ml of ethyl acetate, and the ethyl acetate phase was washed twice with 20 ml of water. The solvent was distilled off under reduced pressure to obtain 0.41 g of 3-(4-(1H-imidazol-1-yl)phenyl)-5-(3,5-dichlorophenyl)-5-(trifluoromethyl)-4,5-dihydroisoxazole (yield 97.6%).

Melting point 193 to 195° C.

Example 4-14

Synthesis of 5-(3,5-dichlorophenyl)-3-(4-(methylthio)phenyl)-5-(trifluoromethyl)-4,5-dihydroisoxazole 0.55 g of toluene and 0.33 g of N-methyl-2-pyrrolidone were added to 0.11 g (0.28 mmol) of 3-(3,5-dichlorophenyl)-4,4,4-trifluoro-1-(4-(methylthio)phenyl)-2-buten-1-one, and the mixture was cooled to 0° C. After adding in dropwise to this mixture the solution which was prepared by adding 0.11 g of water to 0.045 g (1.12 mmol) of sodium hydroxide, and then adding the solution in which 0.022 g (0.31 mmol) of hydroxylamine hydrochloride was dissolved into 0.046 g of water in dropwise, the mixture was stirred for one night at room temperature. The reaction was traced by high-performance liquid chromatography. Since the raw materials did not disappear, the solution in which 0.018 g (0.25 mmol) of hydroxylamine hydrochloride was dissolved into 0.038 g of water was added and stirred for 1 hour at room temperature. The aqueous solution which was prepared from 0.18 g (1.69 mmol) of 35% hydrochloric acid and 0.53 g of water was added in dropwise to the reaction solution, and the mixture was stirred for 1 hour. 5 ml of toluene was added and separation operation was performed. The toluene phase was washed twice with 3 ml of water. The solvent was distilled off under reduced pressure to obtain 0.093 g of 5-(3,5-dichlorophenyl)-3-(4-(methylthio)phenyl)-5-(trifluoromethyl)-4,5-dihydroisoxazole (yield 81.3%).

Melting point 114 to 116° C.

Example 4-15

Synthesis of 3-(6-bromopyridin-3-yl)-5-(3,5-dichlorophenyl)-5-(trifluoromethyl)-4,5-dihydroisoxazole 1.00 g of toluene and 0.60 g of N-methyl-2-pyrrolidone was added to 0.20 g (0.47 mmol) of 1-(6-bromopyridin-3-yl)-3-(3,5-dichlorophenyl)-4,4,4-trifluoro-2-buten-1-one, and the mixture was cooled to 0° C. After adding in dropwise to this mixture the solution which was prepared by adding 0.19 g of water to 0.075 g (1.88 mmol) of sodium hydroxide, and then adding the solution in which 0.036 g (0.52 mmol) of hydroxylamine hydrochloride was dissolved into 0.077 g of water in dropwise, the mixture was stirred for 2 hours at 0° C. The aqueous solution which was prepared from 0.30 g (2.83 mmol) of 35% hydrochloric acid and 0.88 g of water was added in dropwise to the reaction solution, and the mixture was stirred for 1 hour. 5 ml of toluene was added to the reaction solution and separation operation was performed. The toluene phase was washed twice with 3 ml of water. The solvent was distilled off under reduced pressure to obtain 0.18 g of 3-(6-bromopyridin-3-yl)-5-(3,5-dichlorophenyl)-5-(trifluoromethyl)-4,5-dihydroisoxazole (yield 86.8%).

Melting point 147 to 148° C.

Example 4-16

Synthesis of 3-(6-(1H-1,2,4-triazol-1-yl)pyridin-3-yl)-5-(3,5-dichlorophenyl)-5-(trifluoromethyl)-4,5-dihydroisoxazole 2.50 g of toluene and 1.50 g of N-methyl-2-pyrrolidone were added to 0.50 g (1.21 mmol) of 1-(6-(1H-1,2,4-triazol-1-yl)pyridin-3-yl)-3-(3,5-dichlorophenyl)-4,4,4-trifluoro-2-buten-1-one, and the mixture was cooled to 0° C. After adding in dropwise to this mixture the solution which was prepared by adding 0.49 g of water to 0.20 g (4.92 mmol) of sodium hydroxide, and then adding the solution in which 0.094 g (1.35 mmol) of hydroxylamine hydrochloride was dissolved into 0.20 g of water in dropwise, the mixture was stirred for 2 hours at 0° C. The aqueous solution which was prepared from 0.77 g (7.38 mmol) of 35% hydrochloric acid and 2.31 g of water was added in dropwise to the reaction solution, and the mixture was stirred for 1 hour. The reaction solution was cooled to room temperature, and separated by adding 20 ml of ethyl acetate and the ethyl acetate phase was washed twice with 10 ml of water. The solvent was distilled off under reduced pressure to obtain 0.45 g of 3-(6-(1H-1,2,4-triazol-1-yl)pyridin-3-yl)-5-(3,5-dichlorophenyl)-5-(trifluoromethyl)-4,5-dihydroisoxazole (yield 87.3%).

Melting point 170 to 172° C.

Example 4-17

Synthesis of 5-(5-(3,5-dichlorophenyl)-5-(trifluoromethyl)-4,5-dihydroisoxazol-3-yl)-2-(1H-1,2,4-triazol-1-yl) benzonitrile 1.52 g of toluene and 0.91 g of N-methyl-2-pyrrolidone were added to 0.30 g (0.96 mmol) of 5-(3-(3,5-dichlorophenyl)-4,4,4-trifluoro-2-butenoyl)-2-(1H-1,2,4-triazol-1-yl) benzonitrile, and the mixture was cooled to 0° C. After adding in dropwise to this mixture the aqueous solution which was prepared by adding 0.28 g of water to 0.11 g (2.77 mmol) of sodium hydroxide, and then adding the solution in which 0.053 g (0.76 mmol) of hydroxylamine hydrochloride was dissolved into 0.11 g of water in dropwise, the mixture was stirred for 2 hours at 0° C. The aqueous solution which was prepared from 0.43 g (4.16 mmol) of 35% hydrochloric acid and 1.30 g of water was added in dropwise to the reaction solution, and the mixture was stirred for 1 hour. 5 ml of toluene was added and separation operation was performed. The toluene phase was washed twice with 3 ml of water. The solvent was distilled off under reduced pressure to obtain 0.30 g of 5-(5-(3,5-dichlorophenyl)-5-trifluoromethyl-4,5-dihydroisoxazol-3-yl)-2-(1H-1,2,4-triazol-1-yl) benzonitrile (yield 94.5%).

$^1$H-NMR (CDCl$_3$, Me$_4$Si, 300 MHz) δ 8.89 (s, 1H), 8.22 (s, 1H), 8.10 (d, J=8.4 Hz, 2H), 7.93 (d, J=8.4 Hz, 1H), 7.51 (bs, 2H), 7.46 (d, J=1.7 Hz, 1H), 4.12 (d, J=17.4 Hz, 1H), 3.76 (d, J=17.4 Hz, 1H).

Example 4-18

Synthesis of 5-(5-(3,5-dichlorophenyl)-5-(trifluoromethyl)-4,5-dihydroisoxazol-3-yl)-2-fluorobenzonitrile 2.50 g of toluene and 1.50 g of N-methyl-2-pyrrolidone were added to 0.50 g (1.29 mmol) of 5-(3-(3,5-dichlorophenyl)-4,4,4-trifluoro-2-butenoyl)-2-fluorobenzonitrile, and the mixture was cooled to 0° C. After adding in dropwise to this mixture the solution which was prepared by adding 0.52 g of water to 0.21 g (5.16 mmol) of sodium hydroxide, and then adding the solution in which 0.099 g (1.42 mmol) of hydroxylamine hydrochloride was dissolved into 0.21 g of water in dropwise, the mixture was stirred for 2 hours at 0° C. The aqueous solution which was prepared from 0.81 g (7.74 mmol) of 35% hydrochloric acid and 2.42 g of water was added in dropwise to the reaction solution, and the mixture was stirred for 1 hour. 10 ml of toluene was added and separation operation was performed. The toluene phase was washed twice with 5 ml of water. The solvent was distilled off under reduced pressure to obtain 0.48 g of 5-(5-(3,5-dichlorophenyl)-5-(trifluoromethyl)-4,5-dihydroisoxazol-3-yl)-2-fluorobenzonitrile (yield 92.9%).

Melting point 136 to 139° C.

INDUSTRIAL APPLICABILITY

The methods for producing according to the present invention are useful production methods for isoxazoline compounds and intermediates thereof useful for production intermediates for agricultural chemicals, medical drugs and functional materials.

The invention claimed is:
1. A method for producing a 1,3-bis(substituted phenyl)-3-substituted-3-hydroxypropan-1-one compound represented by Formula (3):

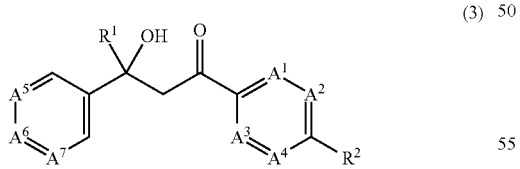

(3)

wherein R$^1$ represents a trifluoromethyl group;
each of A$^1$, A$^2$, A$^3$ and A$^4$ independently represents C—Y;
A$^6$ represents C—H
each of A$^5$ and A$^7$ independently represents C—X;
X represents a halogen atom or a C$_1$-C$_6$ haloalkyl, and each X is optionally the same as or different from each other;
R$^2$ represents a halogen atom, cyano, —C(O)OH, —C(O)OR$^3$, —C(O)NH$_2$, —C(O)N(R$^{1b}$)R$^{1a}$, or a substituent selected from D-21 to D-36;

R$^3$ represents a C$_1$-C$_6$ alkyl, C$_1$-C$_4$ alkoxy (C$_1$-C$_4$) alkyl, or C$_1$-C$_6$ haloalkyl;
Y represents a hydrogen atom, cyano, or C$_1$-C$_4$ alkyl, and each Y is optionally the same as or different from each other;
two adjacent Ys optionally form A$^8$=A$^9$–A$^{10}$=A$^{11}$ together;
each of A$^8$, A$^9$, A$^{10}$ and A$^{11}$ independently represents C—Y$^1$;
Y$^1$ represents a hydrogen atom;
R$^{1a}$ represents a C$_1$-C$_6$ alkyl optionally substituted by R$^8$, —N(R$^{11}$)R$^{10}$, —C(O)OR$^9$, —C(O)NH$_2$, —C(O)NHR$^9$, —C(R$^7$)=NOR$^6$, phenyl, phenyl substituted by (Z)$_{p1}$, D-5, D-7, D-10, D-11, D-12, D-14, D-15, D-18, D-31, D-32, D-42, D-43, D-45, D-46, D-48, E-1, or E-7;
R$^{1b}$ represents a hydrogen atom, C$_1$-C$_6$ alkyl, C$_1$-C$_4$ alkoxy (C$_1$-C$_4$) alkyl, cyano (C$_1$-C$_6$) alkyl, C$_3$-C$_6$ alkynyl, —C(O)R$^9$ or —C(O)OR$^9$,
or represents that R$^{1b}$ optionally forms a 3-7 membered ring with a nitrogen atom to be bonded, by forming a C$_2$-C$_6$ alkylene chain together with R$^{1a}$, and this alkylene chain optionally contains one oxygen atom, sulfur atom or nitrogen atom in this case;
R$^6$ represents a C$_1$-C$_6$ alkyl;
R$^7$ represents a hydrogen atom or C$_1$-C$_6$ alkyl;
R$^8$ represents a halogen atom, cyano, C$_3$-C$_6$ cycloalkyl, C$_1$-C$_6$ alkoxy, C$_1$-C$_6$ haloalkoxy —C(O)N(R$^{15}$)R$^{14}$, —C(R$^7$)=NOR$^6$, phenyl, phenyl substituted by (Z)$_{p1}$, D-11 to D-14, D-18, D-19, D-25, D-26, D-31, D-32, D-36, D-42, D-45, D-48, D-49, E-1, E-2, or E-5;
D-3 to D-5, D-7, D-9 to D-15, D-18 to D-36, and D-42 to D-49 represent aromatic heterocyclic rings represented by the following structural formulae:

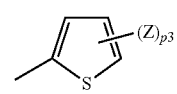

D-3

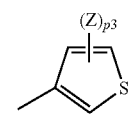

D-4

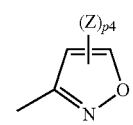

D-5

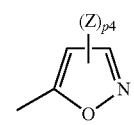

D-7

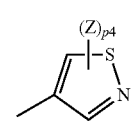

D-9

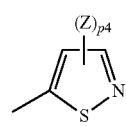

D-10

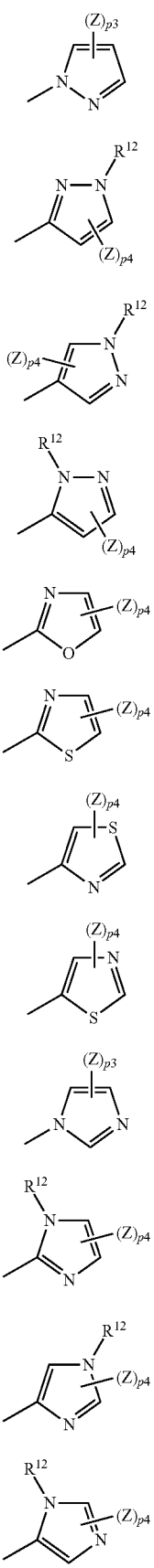
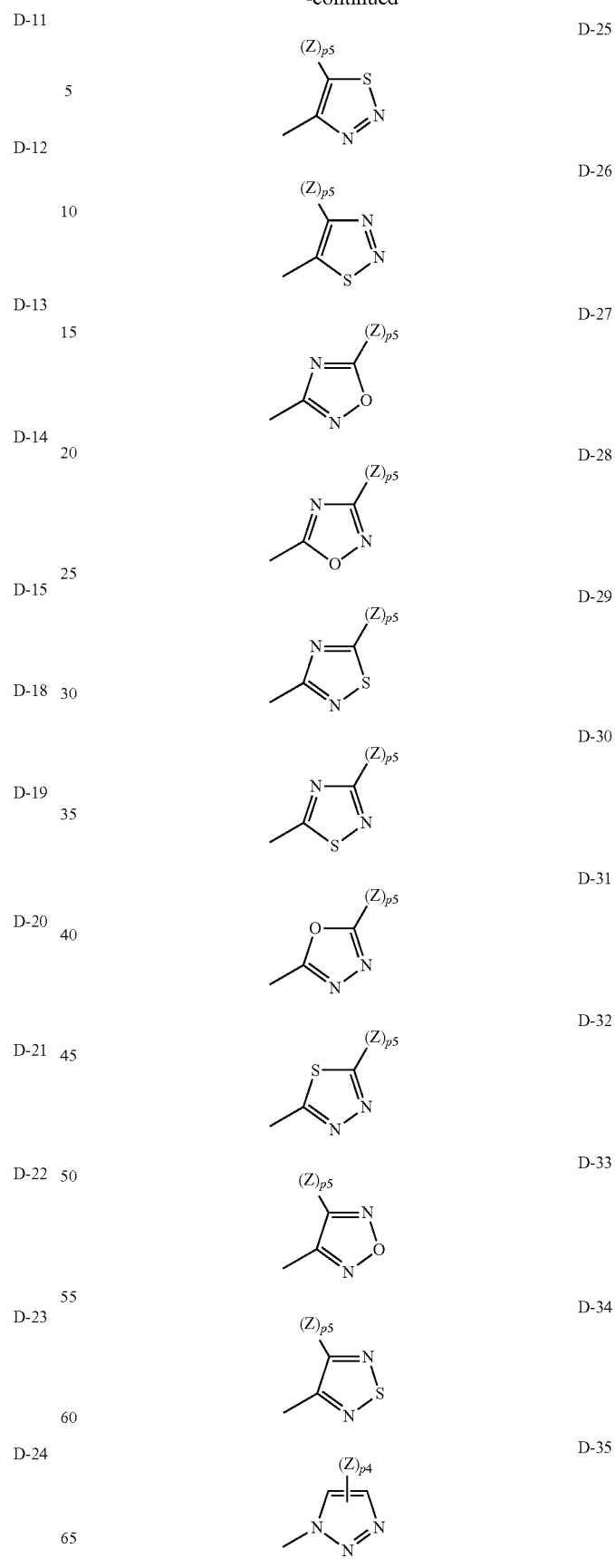

-continued

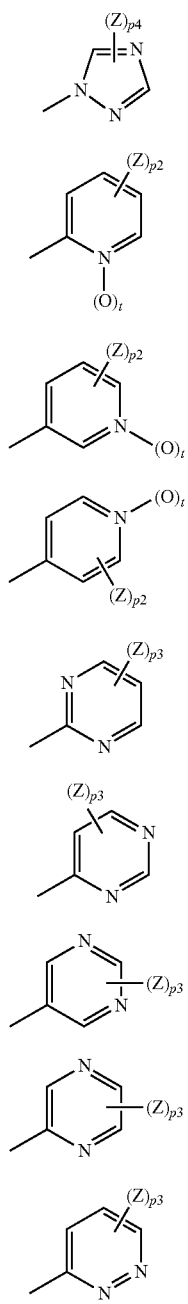

D-36

D-42

D-43

D-44

D-45

D-46

D-47

D-48

D-49

Z represents a halogen atom, cyano, nitro, $C_1$-$C_6$ alkyl, $C_1$-$C_6$ haloalkyl, $C_1$-$C_6$ haloalkoxy, and each Z is optionally the same as or different from each other when p1, p2, p3 or p4 represents an integer of 2 or more;

E-1, E-2, E-5, and E-7 represent saturated heterocycles represented by the following structural formulae:

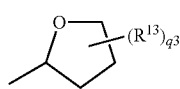

E-1

-continued

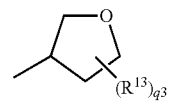

E-2

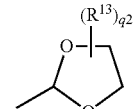

E-5

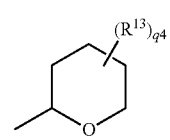

E-7

$R^9$ represents a $C_1$-$C_6$ alkyl, $C_1$-$C_6$ haloalkyl, $C_1$-$C_6$ alkoxy ($C_1$-$C_4$) alkyl, $C_1$-$C_6$ alkylthio ($C_1$-$C_4$) alkyl, $C_3$-$C_8$ cycloalkyl, $C_3$-$C_6$ alkenyl or $C_3$-$C_6$ alkynyl;

$R^{10}$ represents a $C_1$-$C_6$ haloalkyl, —C(O)$R^{14}$, —C(O)OR$^{14}$, phenyl, phenyl substituted by (Z)$_{p1}$, D-3, D-4, D-18, D-42, D-45, D-46, D-48 or D-49;

$R^{11}$ represents a hydrogen atom, $C_1$-$C_6$ alkyl or $C_3$-$C_6$ alkynyl;

$R^{12}$ represents a $C_1$-$C_6$ alkyl;

$R^{13}$ represents a $C_1$-$C_4$ alkyl, and each $R^{13}$ is optionally the same as or different from each other when q2, q3 or q4 represents an integer of 2 or more, wherein two $R^{13}$s optionally form oxo together when two $R^{13}$s are bonded to the same carbon atom;

$R^{14}$ represents a $C_1$-$C_6$ alkyl, $C_1$-$C_6$ haloalkyl, $C_3$-$C_6$ cycloalkyl ($C_1$-$C_4$) alkyl, $C_3$-$C_6$ cycloalkyl, $C_3$-$C_6$ alkenyl or $C_3$-$C_6$ alkynyl;

$R^{15}$ represents a hydrogen atom or $C_1$-$C_6$ alkyl;

$R^{16}$ represents a —OH, $C_1$-$C_4$ alkoxy or $C_1$-$C_4$ alkylthio;

$R^{17}$ represents a hydrogen atom, $C_1$-$C_6$ alkyl, $C_3$-$C_6$ cycloalkyl, $C_3$-$C_6$ alkenyl, $C_3$-$C_6$ haloalkenyl, $C_3$-$C_6$ alkynyl, —C($R^5$)=NOR$^{19}$, —C(O)OR$^{19}$, —C(O)NH$_2$, —C(O)N($R^5$)$R^{19}$, —C(O)NHC(O)$R^{19}$, —C(O)N($R^5$)C(O)OR$^{19}$, —N($R^{21}$)$R^{20}$, phenyl substituted by (Z)$_{p1}$, D-9 to D-11, D-18 to D-20, D-42 to D-47 or D-48;

$R^{18}$ represents a hydrogen atom, $C_1$-$C_6$ alkyl, $C_3$-$C_6$ alkynyl, —C(O)$R^{19a}$, —C(O)OR$^{19a}$ or $C_1$-$C_6$ haloalkylthio;

$R^{19}$ represents a $C_1$-$C_6$ alkyl, $C_1$-$C_6$ haloalkyl or $C_2$-$C_6$ alkenyl;

$R^{19a}$ represents a $C_1$-$C_6$ alkyl, $C_1$-$C_6$ haloalkyl, $C_1$-$C_4$ alkoxy ($C_1$-$C_4$) alkyl, $C_1$-$C_4$ alkylthio ($C_1$-$C_4$) alkyl, $C_1$-$C_4$ alkylsulfinyl ($C_1$-$C_4$) alkyl, $C_1$-$C_4$ alkylsulfonyl ($C_1$-$C_4$) alkyl, $C_3$-$C_6$ cycloalkyl, $C_2$-$C_6$ alkenyl, $C_1$-$C_6$ alkoxycarbonyl, phenyl, phenyl substituted by (Z)$_{p1}$, D42, D43 or D44;

$R^{20}$ represents a $C_1$-$C_6$ haloalkyl, $C_1$-$C_6$ alkoxycarbonyl, phenyl, phenyl substituted by (Z)$_{p1}$, D42 to D46 or D47;

$R^{21}$ represents a hydrogen atom, $C_1$-$C_6$ alkyl, $C_3$-$C_6$ alkenyl or $C_3$-$C_6$ alkynyl;

p1 represents an integer of 1 to 2;
p2 represents an integer of 0 to 1;
p3 represents an integer of 0 to 1;
p4 represents an integer of 0 to 1;
p5 represents an integer of 0 or 1;
q2 represents an integer of 0 to 2;

q3 represents an integer of 0 to 2;
q4 represents an integer of 0 to 2;
r represents an integer of 0 to 2;
t represents an integer of 0 or 1,
the method consisting of
reacting an aromatic ketone compound represented by Formula (4)

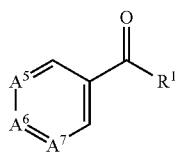

(4)

wherein $R^1$, $A^5$, $A^6$ and $A^7$ represent the same meaning as described above,
and a substituted acetophenone compound represented by Formula (5)

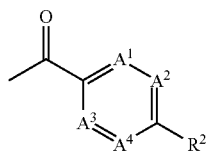

(5)

wherein $R^2$, $A^1$, $A^2$, $A^3$ and $A^4$ represent the same meaning as described above,
in a suspended state in the presence or absence of an additive and in the presence of a base in a solvent, wherein
the base is selected from the group consisting of sodium acetate, potassium acetate, methylamine, ethylamine, n-propylamine, i-propylamine, n-butylamine, i-butylamine, t-butylamine, n-pentylamine, i-pentylamine, benzylamine, aniline, dimethylamine, diethylamine, di-n-propylamine, di-i-propylamine, di-n-butylamine, di-i-butylamine, di-n-pentylamine, di-i-pentylamine, pyrrolidine, piperidine, piperazine, morpholine, dibenzylamine, trimethylamine, triethylamine, tri-n-propylamine, tri-n-butylamine, tripentylamine, tribenzylamine, diisopropylethylamine, N-methylmorpholine, and combinations thereof, and
the additive is selected from the group consisting of a $C_1$-$C_6$ alcohol, an aprotic polar solvent, a surfactant, a water soluble organic solvent, and combinations thereof.

2. The method according to claim 1, wherein the solvent is an organic solvent and the reaction is conducted in the absence of the additive.

3. The method according to claim 1, wherein the solvent is water and the reaction is conducted in the presence of a water-soluble organic solvent as the additive.

4. The method according to claim 1, wherein the solvent is water and the reaction is conducted in the presence of a surfactant as the additive.

5. The method according to claim 1, wherein $R^2$ represents a halogen atom, —C(O)OH, —C(O)OR$^3$, —C(O)NH$_2$, —C(O)N(R$^{1b}$)R$^{1a}$, or a substituent selected from D-21 and D-36.

6. The method according to claim 5, wherein $R^{1a}$ represents a $C_1$-$C_6$ alkyl optionally substituted by $R^8$—N(R$^{11}$)R$^{10}$, —C(O)OR$^9$, —C(O)NH$_2$, —C(O)NHR$^9$, or —C(R$^7$)=NOR$^6$; and
$R^{1b}$ represents a hydrogen atom, $C_1$-$C_6$ alkyl, $C_1$-$C_4$ alkoxy ($C_1$-$C_4$) alkyl, cyano ($C_1$-$C_6$) alkyl, $C_3$-$C_6$ alkynyl, —C(O)R$^9$ or —C(O)OR$^9$.

7. The method according to claim 6, wherein $R^{1a}$ represents a $C_1$-$C_6$ alkyl optionally substituted by $R^8$; and
$R^{1b}$ represents a hydrogen atom, $C_1$-$C_6$ alkyl, $C_1$-$C_4$ alkoxy ($C_1$-$C_4$) alkyl, cyano ($C_1$-$C_6$) alkyl, $C_3$-$C_6$ alkynyl.

8. The method according to claim 7, wherein
$R^{1b}$ represents a hydrogen atom;
$R^3$ represents a $C_1$-$C_6$ alkyl; and
when present, $R^8$ represents D-42.

9. The method according to claim 8, wherein Y represents a hydrogen atom, cyano, or $C_1$-$C_4$ alkyl, and each Y is optionally the same as or different from each other.

10. The method according to claim 1, wherein the base is selected from the group consisting of diethylamine, di-i-propylamine, di-n-propylamine, di-n-butylamine, pyrrolidine, triethylamine, tri-n-butylamine, and combinations thereof.

11. The method according to claim 1, wherein the base is selected from the group consisting of methylamine, ethylamine, n-propylamine, i-propylamine, n-butylamine, i-butylamine, t-butylamine, n-pentylamine, i-pentylamine, and combinations thereof.

* * * * *